US008962598B2

(12) United States Patent
Pettersson

(10) Patent No.: US 8,962,598 B2
(45) Date of Patent: Feb. 24, 2015

(54) 1,2-DIHYDRO-4-HYDROXY-2-OXO-QUINOLINE-3-CARBOXANILIDES AS AHR ACTIVATORS

(75) Inventor: Lars Pettersson, Lund (SE)

(73) Assignee: Immunahr AB, Lund (SE)

( * ) Notice: Subject to any disclaimer, the term of this patent is extended or adjusted under 35 U.S.C. 154(b) by 0 days.

(21) Appl. No.: 13/824,256

(22) PCT Filed: Oct. 11, 2011

(86) PCT No.: PCT/SE2011/000179
§ 371 (c)(1),
(2), (4) Date: Apr. 19, 2013

(87) PCT Pub. No.: WO2012/050500
PCT Pub. Date: Apr. 19, 2012

(65) Prior Publication Data
US 2013/0203703 A1 Aug. 8, 2013

(30) Foreign Application Priority Data
Oct. 14, 2010 (SE) ..................... 1001012

(51) Int. Cl.
A61K 31/675 (2006.01)
C07D 513/02 (2006.01)
C07D 215/00 (2006.01)
C07D 215/56 (2006.01)
C07D 495/04 (2006.01)
C07F 9/60 (2006.01)

(52) U.S. Cl.
CPC ............ C07D 215/56 (2013.01); C07D 495/04 (2013.01); C07F 9/60 (2013.01)
USPC .............................. 514/82; 546/114; 546/155

(58) Field of Classification Search
None
See application file for complete search history.

(56) References Cited

U.S. PATENT DOCUMENTS

| 3,960,868 | A | 6/1976 | Ferrini et al. |
| 4,107,310 | A | 8/1978 | Allais et al. |
| 4,547,511 | A * | 10/1985 | Eriksoo et al. ............... 514/312 |
| 4,738,971 | A | 4/1988 | Eriksoo et al. |
| 5,219,864 | A | 6/1993 | Suzuki et al. |
| 5,310,913 | A | 5/1994 | Gunnarsson et al. |
| 5,580,882 | A | 12/1996 | Abramsky et al. |
| 5,583,135 | A | 12/1996 | Matsuo et al. |
| 5,594,005 | A | 1/1997 | Slavin et al. |
| 5,728,713 | A | 3/1998 | Nilsson et al. |
| 5,739,130 | A | 4/1998 | Matsuo et al. |
| 6,077,851 | A | 6/2000 | Björk et al. |
| 6,395,759 | B1 | 5/2002 | Thompson et al. |
| 6,509,352 | B1 | 1/2003 | Inaba et al. |
| 6,806,276 | B2 | 10/2004 | Inaba et al. |
| 7,105,647 | B1 | 9/2006 | Bradfield et al. |
| 7,279,487 | B2 | 10/2007 | Egbertson et al. |
| 7,553,849 | B2 * | 6/2009 | Bjork et al. .................. 514/301 |
| 7,728,130 | B2 | 6/2010 | Allen et al. |
| 8,012,968 | B2 | 9/2011 | Allen et al. |
| 8,017,626 | B2 | 9/2011 | Allen et al. |
| 8,030,346 | B2 | 10/2011 | Allen et al. |
| 8,048,892 | B2 | 11/2011 | Allen et al. |
| 8,048,894 | B2 | 11/2011 | Allen et al. |
| 8,097,620 | B2 | 1/2012 | Allen et al. |
| 8,349,868 | B2 | 1/2013 | Allen et al. |
| 8,865,742 | B2 | 10/2014 | Marom et al. |
| 2002/0173519 | A1 | 11/2002 | Bjork et al. |
| 2003/0191069 | A1 | 10/2003 | Inaba et al. |

(Continued)

FOREIGN PATENT DOCUMENTS

| EP | 0059698 A1 | 9/1982 |
| EP | 1095021 B1 | 9/2003 |

(Continued)

OTHER PUBLICATIONS

Abd El-Nabi et al., "Synthesis and Reactions of Furo[3,2-c]Quinolines and Furo[3,2-c]Coumarins," Organic Preparations and Procedures Int., vol. 35, No. 5, 2003, pp. 509-514.

Benson et al., "Aryl Hydrocarbon Receptor Activation by TCDD Reduces Inflammation Associated with Crohn's Disease," Toxicological Sciences, vol. 120, No. 1, 2010 (Advance Access Publication Dec. 3, 2010), pp. 68-78.

Björk et al., "Identification of Human S100A9 as a Novel Target for Treatment of Autoimmune Disease via Binding to Quinoline-3-Carboxamides," PLoS Biology, vol. 7, Issue 4, Apr. 28, 2009, pp. 0800-0812.

(Continued)

Primary Examiner — Heidi Reese
(74) Attorney, Agent, or Firm — Birch, Stewart, Kolasch & Birch, LLP

(57) ABSTRACT

The present invention relates to compounds which are 1,2-dihydro-4-hydroxy-2-oxo-quinoline-3-carboxanilides, their thieno-pyridone analogs, and prodrugs thereof. This invention specifically relates to such derivatives containing an N-hydrogen in the carboxanilide moiety and which exhibit modulating activity towards the aromatic hydrocarbon receptor (AhR), and, specifically, also to prodrugs thereof. The present invention also relates to use of said compounds as a medicament, and for the treatment of cancer, autoimmune disorders and other disorders with an immunological component, and a pharmaceutical composition comprising one or more of said compounds and a method of treatment.

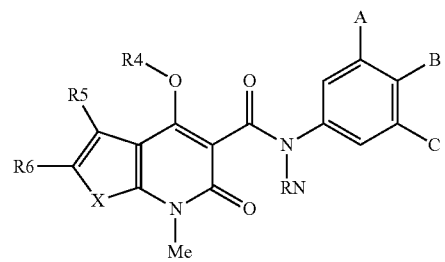

18 Claims, 1 Drawing Sheet

(56) References Cited

U.S. PATENT DOCUMENTS

| | | |
|---|---|---|
| 2005/0119482 A1 | 6/2005 | Egbertson et al. |
| 2005/0192315 A1 | 9/2005 | Jansson et al. |
| 2005/0215586 A1 | 9/2005 | Jansson |
| 2005/0256153 A1 | 11/2005 | Dhanoa et al. |
| 2006/0004038 A1 | 1/2006 | Bjork et al. |
| 2006/0148799 A1 | 7/2006 | De Jong et al. |
| 2007/0124152 A1 | 5/2007 | Johns et al. |
| 2007/0249605 A1 | 10/2007 | Allen et al. |
| 2009/0099171 A1 | 4/2009 | Allen et al. |
| 2009/0111806 A1 | 4/2009 | Allen et al. |
| 2009/0156605 A1 | 6/2009 | Allen et al. |
| 2009/0156633 A1 | 6/2009 | Allen et al. |
| 2009/0163545 A1 | 6/2009 | Goldfarb |
| 2009/0170840 A1 | 7/2009 | Roth et al. |
| 2009/0325948 A1 | 12/2009 | Hurley et al. |
| 2010/0184763 A1 | 7/2010 | Allen et al. |
| 2010/0240610 A1 | 9/2010 | Allen et al. |
| 2011/0224248 A1 | 9/2011 | Allen et al. |

FOREIGN PATENT DOCUMENTS

| | | |
|---|---|---|
| JP | 2-152966 A | 6/1990 |
| WO | WO 92/18483 A1 | 10/1992 |
| WO | WO 9218483 A1 * | 10/1992 |
| WO | WO 94/29295 A1 | 12/1994 |
| WO | WO 00/03991 A1 | 1/2000 |
| WO | WO 00/03992 A1 | 1/2000 |
| WO | WO 01/30758 A1 | 5/2001 |
| WO | WO 03/000681 A1 | 1/2003 |
| WO | WO 2005/123744 A1 | 12/2005 |
| WO | WO 2007/038571 A2 | 4/2007 |

OTHER PUBLICATIONS

Boros et al., "Synthesis and HIV-integrase strand transfer inhibition activity of 7-hydroxy[1,3]thiazolo[5,4-b]pyridin-5(4H)-ones," Bioorganic & Medicinal Chemistry Letters, vol. 16, 2006, pp. 5668-5672.

CAS Registry, RN 1257535-80-0, CA Index Name: 3-Quinolinecarboxamide, N[3,5-dichlorophenyl)-1,2-dihydro-4-hydroxy-1-methyl-2-oxo-, Entered STN Dec. 27, 2010.

CAS Registry, RN 1257537-64-6, CA Index Name: 3-Quinolinecarboxamide, N-[3-chloro-4-(trifluoromethyl)phenyl]-1,2-dihydro-4-hydroxy-1-methyl-2-oxo-, Entered STN Dec. 27, 2010.

CAS Registry, RN 303100-72-3, CA Index Name: 3-Quinolinecarboxamide, 1,2-dihydro-4-hydroxy-1-methyl-N-(3-methylphenyl)-2-oxo-, Entered STN Nov. 17, 2000.

CAS Registry, RN 305868-90-0, CA Index Name: 3-Quinolinecarboxamide, N-(3-chlorophenyl)-1,2-dihydro-4-hydroxy-1-methyl-2-oxo-, Entered STN Dec. 1, 2000.

CAS Registry, RN 312742-66-8, CA Index Name: 3-Quinolinecarboxamide, N-(3,4-dichlorophenyl)-1,2-dihydro-4-hydroxy-1-methyl-2-oxo-, Entered STN Jan. 4, 2001.

CAS Registry, RN 372171-88-5, CA Index Name: 3-Quinolinecarboxamide, N-3,5-dimethylphenyl)-1,2-dihydro-4-hydroxy-1-methyl-2-oxo-, Entered STN Nov. 29, 2001.

CAS Registry, RN 372171-92-1, CA Index Name: 3-Quinolinecarboxamide, N-(4-ethoxyphenyl)-1,2-dihydro-4-hydroxy-1-methyl-2-oxo-, Entered STN Nov. 29, 2001.

CAS Registry, RN 376618-80-3, CA Index Name: 3-Quinolinecarboxamide, N-(2,5-dimethhylphenyl)-1,2-dihydro-4-hydroxy-1-methyl-2-oxo-, Entered STN Dec. 19, 2001.

Collin et al., "Synthesis of N-Pyridinyl(methyl)-1,2-dihydro-4-hydroxy-2-oxoquinoline-3-carboxamides and analogues and their anti-inflammatory activity in mice and rats," Journal of Pharmacy and Pharmacology, vol. 53, 2001, pp. 417-423.

Dabir et al., "Aryl Hydrocarbon Receptor (AhR) is Activated by Glucose and Regulates the Thrombospondin-1 Gene Promoter in Endothelial Cells," Circ. Res., vol. 102, No. 12, Jun. 20, 2008, pp. 1558-1565 (18 pages total).

Dayam et al., "Discovery and Structure-Activity Relationship Studies of a Unique Class of HIV-1 Integrase Inhibitors," Chem. Med. Chem, vol. 1, 2006, pp. 238-244.

Detsi et al., "Design and Synthesis of Novel Quinolinone-3-aminoamides and Their α-Lipoic Acid Adducts as Antioxidant and Anti-inflammatory Agents," J. Med. Chem., vol. 50, 2007 (Published on Web Apr. 20, 2007), pp. 2450-2458.

Duerkop et al., "Sensitive Terbium Probes for Luminescent Determination of both Alkaline Phosphatase and Codeine Phosphate," Ann. N.Y. Acad. Sci., vol. 1130, 2008, pp. 172-178.

Hauben et al., "Activation of the aryl hydrocarbon receptor promotes allograft-specific tolerance through direct and dendritic cell mediated effects on regulatory T cells," Blood, vol. 112, 2008 (Prepublished online Jun. 11, 2008), pp. 1214-1222.

He et al., "Probabilistic Neural Network Multiple Classifier System for Predicting the Genotoxicity of Quinolone and Quinoline Derivatives," Chem. Res. Toxicol., vol. 18, 2005 (Published on Web Feb. 8, 2005), pp. 428-440.

Ho et al., "The aryl hydrocarbon receptor: a regulator of Th17 and Treg cell development in disease," Cell Research, vol. 18, 2008 (Published Online Jun. 2, 2008), pp. 605-608.

International Search Report and Written Opinion of the International Searching Authority (Forms PCT/ISA/220, PCT/ISA/210 and PCT/ISA/237), dated Feb. 1, 2012, for International Application No. PCT/SE2011/00179.

Jansson et al., "Synthesis and Reactivity of Laquinimod, a Quinoline-3-carboxamide: Intramolecular Transfer of the Enol Proton to a Nitrogen Atom as a Plausible Mechanism for Ketene Formation," J. Org. Chem., vol. 71, 2006 (Published on Web Jan. 21, 2006), pp. 1658-1667.

Jönsson et al., "Synthesis and Biological Evaluation of New 1,2-Dihydro-4-hydroxy-2-oxo-3-quinolinecarboxamides for Treatment of Autoimmune Disorders: Structure-Activity Relationship," J. Med. Chem., vol. 47, 2004 (Published on Web Mar. 16, 2004), pp. 2075-2088.

Jover et al., "Down-regulation of human CYP3A4 by the inflammatory signal interleukin-6: molecular mechanism and transcription factors involved," The FASEB Journal, vol. 16, Nov. 2002, pp. 1799-1801.

Kawajiri et al., "Aryl hydrocarbon receptor suppresses intestinal carcinogenesis in ApcMin/+ mice with natural ligands," PNAS, vol. 106, No. 32, Aug. 11, 2009, pp. 13481-13486.

Kerkvliet et al., "Activation of aryl hydrocarbon receptor by TCDD prevents diabetes in NOD mice and increases Foxp3+ T cells in pancreatic lymph nodes," Immunotherapy, vol. 1, No. 4, Jul. 1, 2009, pp. 539-547.

Kewley et al., "The mammalian basic helix-loop-helix/PAS family of transcriptional regulators," The International Journal of Biochemistry & Cell Biology, vol. 36, 2004, pp. 189-204.

Khan et al., "Modified Synthesis and Antiangiogenic Activity of Linomide," Bioorganic & Medicinal Chemistry Letters, vol. 11, 2001, pp. 451-452.

Lawrence et al., "Activation of the aryl hydrocarbon receptor is essential for mediating the anti-inflammatory effects of a novel low-molecular-weight compound," Blood, vol. 112, 2008 (Prepublished online Feb. 12, 2008), pp. 1158-1165.

Lee et al., Anthelmintic β-Hydroxyketoamides (BKAS), Bioorganic & Medicinal Chemistry Letters, vol. 8, 1998, pp. 3317-3320.

Morgan et al., "Regulation of Drug-Metabolizing Enzymes and Transporters in Infection, Inflammation, and Cancer," Drug Metabolism and Disposition, vol. 36, No. 2, 2008, pp. 205-216.

Ohtake et al., "Dioxin receptor is a ligand-dependent E3 ubiquitin ligase," Nature, vol. 446, Mar. 29, 2007, pp. 562-566.

Osherovich, "Dousing diabetes' flames," Science-Business eXchange, vol. 2, No. 31, 2009 (Published online Aug. 13, 2009), pp. 1-2.

Poppe et al., "Different Modes of Inhibitor Binding to Prolyl Hydroxylase by Combined Use of X-ray Crystallography and NMR Spectroscopy of Paramagnetic Complexes," J. Am. Chem. Soc., vol. 131, 2009 (Published on Web Nov. 3, 2009), pp. 16654-16655.

Pot et al., "Type 1 regulatory T cells (Tr1) in autoimmunity," Seminars in Immunology, vol. 23, 2011, pp. 202-208.

(56) References Cited

OTHER PUBLICATIONS

Quintana et al., Control of Treg and TH17 cell differentiation by the aryl hydrocarbon receptor, Nature, vol. 453, May 1, 2008, pp. 65-72.

Rankin et al., "The role of hypoxia-inducible factors in tumorigenesis," Cell Death and Differentiation, vol. 15, 2008 (Published online Feb. 15, 2008), pp. 678-685.

Schulz et al., "Activation of the Aryl Hydrocarbon Receptor Suppresses Sensitization in a Mouse Peanut Allergy Model," Toxicological Sciences, vol. 123, No. 2, 2011 (Advance Access Publication Jul. 29, 2011), pp. 491-500.

SciFinder Search, dated Aug. 18, 2011, Task History: Explore substances by substructure, Am. Chem. Soc. Registry Nos. 1071850-28-6; 1071850-02-6; 872121-48-7; 872121-47-6; 869493-20-9; 869493-19-6; 666234-52-2; 548766-22-9; 479634-26-9; 151328-13-1; and 84088-76-6 (4 pages).

Shi et al., "Structure-Activity Relationships Studies of the Anti-Angiogenic Activities of Linomide," Bioorganic & Medicinal Chemistry Letters, vol. 13, 2003, pp. 1187-1189.

Shridhar et al., "Anti-inflammatory agents. Part II. Synthesis and anti-inflammatory activity of 3,4-disubstituted 2-oxo-1,2-dihydroquinolines," CAS Registry, CAN 93:204422, AN 1980:604422, CAPLUS, 2008, Abstract only.

Sidorenko et al., "Synthesis and antimycobacterial activity of trifluoromethyl-substituted anilides of 1-R-4-hydroxy-2-oxo-1,2-dihydroquinoline-3-carboxylic acids," Farmatsevtichnil Zhurnal, Kiev, Ukraine, vol. 1, 2009, pp. 72-76, Abstract only.

Singh et al., "Activation of Aryl Hydrocarbon Receptor (AhR) Leads to Reciprocal Epigenetic Regulation of FoxP3 and IL-17 Expression and Amelioration of Experimental Colitis," PLoS One, vol. 6, Issue 8, Aug. 15, 2011, pp. 1-13.

Taran et al., "4-Hydroxy-2-Quinolones. 47*. Synthesis and Diuretic Activity of (2H-1,2,4-Benzothiadiazine-1,1-Dioxide-3-YL)Methylamides of 1R-4-Hydroxy-2-Oxoquinoline-3-Carboxylic Acids," Chemistry of Heterocyclic Compounds, vol. 37, No. 2, 2001, pp. 237-240.

Tsuji et al., "Synthesis and Antinephritic Activities of Quinoline-3-carboxamides and Related Compounds," Bioorganic & Medicinal Chemistry Letters, vol. 12, 2002, pp. 85-88.

Tuvesson et al., "Cytochrome P450 3A4 is the Major Enzyme Responsible for the Metabolism of Laquinimod, A Novel Immunomodulator," Drug Metabolism and Disposition, vol. 33, No. 6, 2005, pp. 866-872.

Tuvesson et al., "Identification of cytochrome P4503A as the major subfamily responsible for the metabolism of roquinimex in man," Xenobiotica, vol. 30, Issue 9, 2000, pp. 905-914, SciFinder Abstract (2 pages), AN 2000:740640, CAN 134:50955, CAPLUS.

Ukrainets et al., "4-Hydroxy-2-Quinolones. 110*. Bromination of 1-R-4-Hydroxy-2-Oxo-1,2-Dihydroquinoline-3-Carboxylic Acid Anilides," Chemistry of Heterocyclic Compounds, vol. 42, No. 10, 2006, pp. 1301-1307.

Ukrainets et al., "4-Hydroxy-2-quinolones. 15. The synthesis of 2-pyridyl 1-R-2-oxo-4-hydroxyquinoline-3-carboxamides as potential new non-steroidal . . . ," Khimiya Geterotsiklicheskikh Soedinenii, vol. 8, 1993, pp. 1101-1104, CAN 120:244609, AN 1994:244609, Abstract only.

Ukrainets et al., "4-Hydroxy-2-quinolones. 18. Synthesis and antithyroid activity of 1-R-2-oxo-3-(4-oxo-3H-quinazolin-2-yl)-4-hydroxyquinolines," Khimiya Geterotsiklicheskikh Soedinenii, vol. 9, 1993, pp. 1223-1226, Abstract only.

Ukrainets et al., "4-Hydroxy-2-Quinolones. 42*. Synthesis and Biological Activity of 1-R-2-Oxo-3-(2H-1,2,4-Benzothiadiazine-1,1-Dioxid-3-YL)-4-Hydroxyquinolines," Chemistry of Heterocyclic Compounds, vol. 36, No. 3, 2000, pp. 346-350.

Ukrainets et al., "4-Hydroxy-2-quinolones. 7. Synthesis and biological properties of 1-R-3-(benzimidazolyl-2)-4-hydroxy-2-quinolones," Khimiya Geterotsiklicheskikh Soedinenii, vol. 1, 1993, pp. 105-108, CAN 120:8457, AN 1994:8457, CAPLUS, Abstract only.

Ukrainets et al., "Pyridylamides of 1-R-2-oxo-4-hydroxyquinoline-3-carboxylic acids. Synthesis, physical, chemical and antituberculous poperties," Visnik Farmatsii, vol. 1, 2004, pp. 12-19, CAN 142:280027, AN 2004:543730, CAPLUS, Abstract only.

Ukrainets et al., "Synthesis and antituberculosis properties of 1-substituted 1,2-dihydro-4-hydroxy-2-oxo-3-quinolinecarboxylic acid picolylamides," Visnik Farmatsii, vol. 1, 2005, pp. 10-14, CAN 144:432667, AN 2005:559533, CAPLUS, Abstract only.

Ukrainets et al., "Synthesis and biological properties of 1-R-4-hydroxy-2-oxoquinoline-3-carboxylic acids 4'-hydroxyanilides," Farmatsevtichnii Zhurnal (Kiev), vol. 6, 2001, pp. 48-51, CAN 137:352875, AN 2002:164025, CAPLUS, Abstract only.

Ukrainets et al., "Synthesis and diuretic activity of 1-R-3-(6'-chloro-7'-sulfamyl-2'H-1',2',4'- benzothiadiazine-1',1'-dioxide-3'-yl)-4-hydroxy-2-oxoquinolines," Visnik Farmatsii, vol. 2, 2003, pp. 16-19, CAN 141:225468, AN 2003:879466, CAPLUS, Abstract only.

Veldhoen et al., "The aryl hydrocarbon receptor links TH17-cell-mediated autoimmunity to environmental toxins," Nature, vol. 453, May 1, 2008, pp. 106-110.

Vezina et al., "AHR signaling in prostate growth, morphogenesis, and disease," Biochemical Pharmacology, vol. 77, 2009, pp. 566-576.

Vukanovic et al., "Linomide Inhibits Angiogenesis, Growth, Metastasis, and Macrophage Infiltration within Rat Prostatic Cancers," Cancer Research, vol. 55, Apr. 1, 1995, pp. 1499-1504.

Yuan et al., "Regulatory T cells as a potent target for controlling bone loss," Biochemical and Biophysical Research Communications, Oct. 8, 2010, 4 pages.

Zhang et al., "Suppression of Experimental Autoimmune Uveoretinitis by Inducing Differentiation of Regulatory T Cells via Activation of Aryl Hydrocarbon Receptor," Investigative Ophthalmology & Visual Science, vol. 51, No. 4, Apr. 2010, pp. 2109-2117.

Dalrymple et al., "The Quinoline-3-Carboxamide Anti-Angiogenic Agent, Tasquinimod, Enhances the Anti-Prostate Cancer Efficacy of Androgen Ablation and Taxotere Without Effecting Serum PSA Directly in Human Xenografts", The Prostate, vol. 67, 2007, pp. 790-797, XP055094360.

Extended European Search Report for corresponding Application No. 11832828.5 dated Jan. 7, 2014.

Isaacs et al., "Identification of ABR-215050 as Lead Second Generation Quinoline-3-Carboxamide Anti-Angiogenic Agent for the Treatment of Prostate Cancer", The Prostate, vol. 66, 2006, pp. 1768-1778, XP055094361.

\* cited by examiner

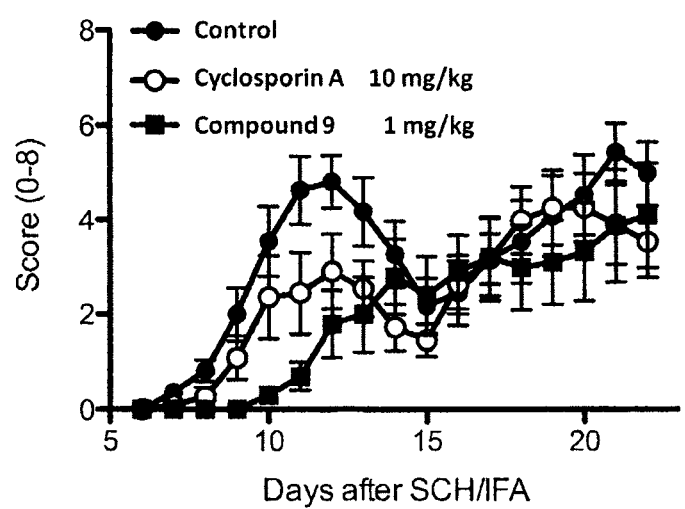

1,2-DIHYDRO-4-HYDROXY-2-OXO-QUINOLINE-3-CARBOXANILIDES AS AHR ACTIVATORS

FIELD OF THE INVENTION

The present invention relates to compounds which are 1,2-dihydro-4-hydroxy-2-oxo-quinoline-3-carboxanilides, their thieno-pyridone analogs, and prodrugs thereof. This invention specifically relates to such derivatives containing an N-hydrogen in the carboxanilide moiety and which exhibit modulating activity towards the aromatic hydrocarbon receptor (AhR), and, specifically, also to prodrugs thereof. The present invention also relates to use of said compounds as a medicament, and for the treatment of cancer, autoimmune disorders and other disorders with an immunological component, and a pharmaceutical composition comprising one or more of said compounds and a method of treatment.

BACKGROUND 1,2-dihydro-4-hydroxy-2-oxo-quinoline-3-carboxanilides have been described in the literature since the 1970s (refs 1-4). The most well-known compound in this class, roquinimex (Linomide), was first described by A B Leo as an immuno-stimulating agent (ref 4) but was later also found to have immuno-modulating effects, as well as anti-angiogenetic effects (refs 5a, b). Roquinimex has been claimed beneficial for the treatment of autoimmune diseases, such as rheumatoid arthritis, multiple sclerosis, systemic lupus erythematosus, inflammatory bowel disease, diabetes type 1, and psoriasis, as well as for the treatment of cancer (refs 6a-d, 9d and refs therein).

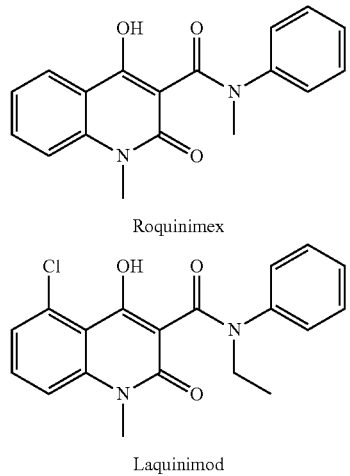

The compound laquinimod (a 5-Cl, N-Et carboxanilide derivative) has been reported by Active Biotech AB to convey a better therapeutic index compared with roquinimex (refs 7a, b) and is currently in phase III clinical studies for the treatment of multiple sclerosis. Laquinimod has also entered clinical trials in Crohn's disease and SLE. Two other compounds in the same class under clinical evaluation are tasquinimod (prostate cancer) and paquinimod (systemic sclerosis). Recently, a molecular target for laquinimod was identified as S100A9 (ref 8).

Fujisawa has reported on similar compounds with inhibitory activity on nephritis and on B16 melanoma metastases (refs 9a-d). Also the closely related thieno-pyridone analogs have been described as immunomodulating compounds with anti-inflammatory properties (ref 10).

Another closely related compound class are the corresponding N-pyridyl-carboxamide derivatives, which have been reported to have antitubercular activity as well as anti-inflammatory properties (ref 11). However, according to literature (ref 10) these derivatives are less active as immuno-modulating agents.

The N-hydrogen 3-carboxanilides ("N—H derivatives") and the N-alkyl 3-carboxanilides ("N-alkyl derivatives"), respectively, are described in the prior art documents relating to inflammation, immunomodulation, and cancer as a homogenous group of compounds in terms of biological effects. Prior art also teaches that the N-alkyl derivatives are the preferred compound derivatives.

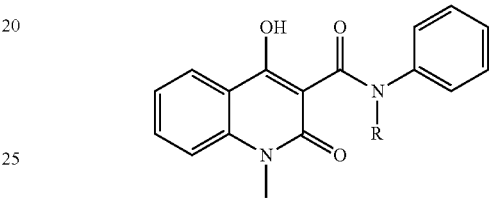

R = alkyl: "N-alkyl derivatives" R = hydrogen: "N—H derivatives"

In fact, very few studies (refs 4, 9d) of N-hydrogen derivatives, especially in vivo studies, have been reported. Furthermore, no fundamental biological differences between the N-alkyl derivatives and the N-hydrogen derivatives, respectively, have been described.

However, some chemical properties of the N-hydrogen and the N-alkyl derivatives are different (ref 12). N-Alkyl derivatives adopt a twisted 3D-structure, whereas the N—H derivatives are stabilized by intramolecular hydrogen bonds in a planar structure. The N-alkyl derivatives are more soluble in aqueous media, but also inherently unstable towards nucleophiles, such as amines and alcohols (refs 12, 13).

The N-alkyl derivatives roquinimex (N-Me) and laquinimod (N-Et) have been reported to be metabolized in human microsomes to give the corresponding N-hydrogen derivatives, via N-dealkylation catalyzed mainly by CYP3A4 (refs 14a, b).

bHLH-PAS (basic helix-loop-helix Per-Arnt-Sim) proteins constitute a recently discovered protein family functioning as transcription factors as homo or hetero protein dimers (refs 15a, b). The N-terminal bHLH domain is responsible for DNA binding and contributes to dimerization with other family members. The PAS region (PAS-A and PAS-B) is also involved in protein-protein interactions determining the choice of dimerization partner and the PAS-B domain harbors a potential ligand binding pocket.

The aryl hydrocarbon receptor (AhR or dioxin receptor) and its dimerization partner ARNT (AhR nuclear translocator) were the first mammalian protein members to be identified. AhR is a cytosolic protein in its non-activated form, associated in a protein complex with Hsp90, p23, and XAP2. Upon ligand activation, typically by chlorinated aromatic hydrocarbons like TCDD, the Ahr enters the nucleus and dimerizes with ARNT. The AhR/ARNT dimer recognizes specific xenobiotic response elements (XREs) to regulate TCDD-responsive genes. The ligand binding domain of AhR (AhR-LBD) resides in the PAS-B domain.

Recently, it has been demonstrated that AhR is involved in Th17 and Treg cell development and AhR has been proposed as a unique target for therapeutic immuno-modulation (refs 16a-c). The AhR ligand TCDD was shown to induce development of Treg(FoxP3$^+$) cells, essential for controlling autoimmunity, and to suppress symptoms in the EAE model. In addition, activation of AhR has been shown essential for the generation of IL-10 producing regulatory Tr1 cells (ref 16d), and Ahr ligands have also been proven efficacious in other models of auto-immunity, e.g. diabetes type 1, IBD, and uveitis (refs 16e-h). Apart from controlling autoimmune disorders, AhR activation and Treg cell development have been implicated as a therapeutic strategy for other conditions with an immunological component, such as allergic lung inflammation, food allergy, transplant rejection, bone loss, and type 2 diabetes and other metabolic disorders (refs 17a-e).

Apart from its role as a transcription factor, AhR has been reported to function as a ligand-dependent E3 ubiquitin ligase (ref 18), and ligand-induced degradation of β-catenin has been demonstrated to suppress intestinal cancer in mice (ref 19). In addition, activation of AhR has been implicated to play a protective role in prostate cancer (ref 20).

Other members of the bHLH-PAS family are the HIF-α (hypoxia inducible factor alpha) proteins, which also heterodimerize with ARNT. In conditions with normal oxygen levels (normoxia), HIF-α proteins are rapidly degraded by the ubiquitin-proteasome system and they are also inactivated by asparagine hydroxylation. Under hypoxic conditions, however, the proteins are active and upregulate genes as a response to the hypoxic state, e.g. genes for erythropoietin and vascular endothelial growth factor (VEGF). VEGF is essential for blood vessel growth (angiogenesis) and is together with HIF-1a considered as interesting targets for anti-angiogenetic tumour therapy (ref 21). HIF-α proteins can be negatively and indirectly regulated by AhR ligands, which upon binding with AhR reduce the level of the common dimerization partner ARNT. Anti-angiogenetic effects can possibly also be achieved directly by AhR activity via upregulation of thrombospondin-1 (ref 22).

SUMMARY OF THE INVENTION

The inventor of the present invention has surprisingly found that the N-hydrogen 1,2-dihydro-4-hydroxy-2-oxoquinoline-3-carboxanilides and the N-hydrogen 6,7-dihydro-4-hydroxy-7-methyl-6-oxo-thieno[2,3-b]pyridine-5-carboxanilides (thieno-pyridone analogs) are potent activators of AhR. This is in contrast to their corresponding N-alkyl analogs.

The metabolizing enzyme transforming the N-alkyl derivatives to the N-hydrogen AhR activating derivatives is mainly CYP3A4. This enzyme shows a large variability within a general population and is also susceptible to drug-drug interactions with a number of different drugs (ref 14b). Moreover, CYP3A enzymes have been reported to be down-regulated under inflammatory conditions (refs 23a, b). Thus, a person treated with an N-alkyl derivative, such as roquinimex or laquinimod, will be exposed to a varying level of the corresponding N-hydrogen derivative, depending on individual CYP3A4 status and on possible drug-drug interactions, which may lead to inadequate exposure.

The concept of prodrugs is well-known for a person skilled in the art. An ideal prodrug is a biologically inactive compound with optimal physico-chemical properties, e.g. solubility and chemical stability, and which is transformed by the organism in a predictable way to give the biologically active drug (metabolite) compound. This relationship between a prodrug and drug can be likened with the relationship between a drug (parent compound) and its active metabolite.

The N-alkyl derivatives, such as roquinimex and laquinimod, can be considered as prodrugs of the N-hydrogen derivatives. As can be seen, however, there are several liabilities with the N-alkyl derivatives as prodrugs. The N-alkyl derivatives are chemically reactive towards nucleophiles (refs 12, 13) making them unstable in their neutral forms and possibly reactive in a biological environment. They are also biologically transformed in an unpredictable way by CYP enzymes, and, they may have inherent biological activity on their own. In addition, prodrugs that are transformed by hepatic metabolism are not optimal for topical treatment.

The use of the N-hydrogen derivatives as drug compounds may in certain instances also be complicated mainly for two reasons. First, the very low aqueous solubility of N-hydrogen derivatives due to intramolecular hydrogen bonds (ref 12) can complicate e.g. formulation and affect pharmacokinetic properties, such as uptake and bioavailability. Second, some N-hydrogen derivatives are metabolically unstable, e.g. the N-hydrogen metabolite of laquinimod was reported to be rapidly metabolized in the aniline part of the molecule (ref 14b), and as AhR ligands they may induce their own breakdown by CYP1A mediated metabolism causing a transient activity. Blocking such metabolism by aromatic substituents may be important in order to modulate the metabolic stability of the compounds. In some instances, however, e.g. when topical treatment is preferred, a rapid systemic or hepatic clearance may be advantageous.

The inventor of the present invention has found that the properties of the N-hydrogen derivatives as drug compounds can be greatly improved by the introduction of prodrug moieties that break up intramolecular anilide-NH and/or 4-OH hydrogen bonds.

The concept is shown below. Stabilization of a planar structure by intramolecular hydrogen bonds results in very low aqueous solubility. Breaking the H-bond(s) by the introduction of prodrug moieties PM1 and/or PM2, respectively, can improve e.g. the solubility considerably. Also, inherent physical, chemical, or biological properties of selected PM1 and PM2, e.g. polarity, specific affinity, targeting properties, etc., can be exploited in the design of the prodrug compounds.

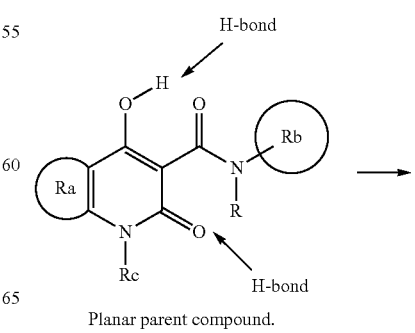

Planar parent compound.

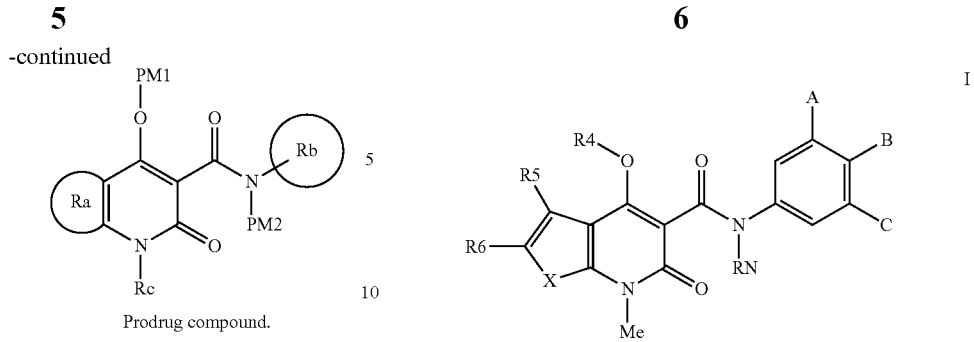

Prodrug compound.

Conceptually, Ra, Rb, and Rc may independently represent any type of group(s) or substituent(s), e.g. aromatic rings, hetero-aromatic rings, hetero-cyclic or alicyclic rings, or open-chain structures. The prodrug moieties PM1 and PM2, respectively, represent groups susceptible to cleavage in an organism providing the bioactive planar parent compound.

The objective problem of the present invention is to develop new N-hydrogen 1,2-dihydro-4-hydroxy-2-oxo-quinoline-3-carboxanilides and N-hydrogen 6,7-dihydro-4-hydroxy-7-methyl-6-oxo-thieno[2,3-b]pyridine-5-carboxanilides, as activators of the aryl hydrocarbon receptor for the treatment of cancer, autoimmune disorders and other disorders with an immunological component.

Another objective problem of the present invention is to develop new prodrug compounds of said N-hydrogen 1,2-dihydro-4-hydroxy-2-oxo-quinoline-3-carboxanilides and N-hydrogen 6,7-dihydro-4-hydroxy-7-methyl-6-oxo-thieno[2,3-b]pyridine-5-carboxanilides.

Compounds of the present invention that activate the aryl hydrocarbon receptor are especially useful for the treatment of cancer, such as leukemia, prostate cancer and intestinal cancer, of autoimmune diseases, such as rheumatoid arthritis, multiple sclerosis, systemic lupus erythematosus, inflammatory bowel disease, diabetes type 1, and psoriasis, and of other disorders or conditions with an immunological component, such as asthma, allergy, infection, bone loss, atherosclerosis, diabetes type 2, graft-versus-host, and transplant rejection.

BRIEF DESCRIPTION OF THE DRAWINGS

FIG. 1 provides a Graph showing administration (1 mg/kg day (0, 3, 6, 9)) of Compound 9 in preventing EAE development.

DETAILED DESCRIPTION OF THE INVENTION

The object of the present invention is to provide novel compounds which are N-hydrogen 1,2-dihydro-4-hydroxy-2-oxo-quinoline-3-carboxanilides or N-hydrogen 6,7-dihydro-4-hydroxy-7-methyl-6-oxo-thieno[2,3-b]pyridine-5-carboxanilides and prodrugs thereof.

In a first aspect the present invention relates to a compound of the general formula I wherein
A, B and C are independently chosen from the group comprising H, Me, Et, iso-Pr, tert-Bu, OMe, OEt, O-iso-Pr, SMe, S(O)Me, S(O)$_2$Me, CF$_3$, OCF$_3$, F, Cl, Br, I, and CN, or A and B represents OCH$_2$O and C is H; RN is chosen from the group comprising H, C(O)H, C(O)Me, C(O)Et, C(O)Pr, C(O)CH(Me)$_2$, C(O)C(Me)$_3$, C(O)Ph, C(O)CH$_2$Ph, CO$_2$H, CO$_2$Me, CO$_2$Et, CO$_2$CH$_2$Ph, C(O)NHMe, C(O)NMe$_2$, C(O)NHEt, C(O)NEt$_2$, C(O)NHPh, C(O)NHCH$_2$Ph, the acyl residues of C5-C20 carboxylic acids optionally containing 1-3 multiple bonds, and the acyl residues of the amino acids glycine, alanine, valine, leucine, iso-leucine, serine, threonine, cysteine, methionine, proline, asparagine, glutamine, aspartic acid, glutamic acid, lysine, arginine, histidine, phenylalanine, tyrosine, and tryptophan, and optionally substituted 1-3 times by substituents chosen from the group comprising Me, Et, OMe, OEt, SMe, S(O)Me, S(O)$_2$Me, S(O)$_2$NMe$_2$, CF$_3$, OCF$_3$, F, Cl, OH, CO$_2$H, CO$_2$Me, CO$_2$Et, C(O)NH$_2$, C(O)NMe$_2$, NH$_2$, NH$_3$$^+$, NMe$_2$, NMe$_3$$^+$, NHC(O)Me, NC(=NH)NH$_2$, OS(O)$_2$OH, S(O)$_2$OH, OP(O)(OH)$_2$, and P(O)(OH)$_2$;
R4 is RN, or when RN is H, then R4 is chosen from the group comprising H, P(O)(OH)$_2$, P(O)(OMe)$_2$, P(O)(OEt)$_2$, P(O)(OPh)$_2$, P(O)(OCH$_2$Ph)$_2$, S(O)$_2$OH, S(O)$_2$NH$_2$, S(O)$_2$NMe$_2$, C(O)H, C(O)Me, C(O)Et, C(O)Pr, C(O)CH(Me)$_2$, C(O)C(Me)$_3$, C(O)Ph, C(O)CH$_2$Ph, CO$_2$H, CO$_2$Me, CO$_2$Et, CO$_2$CH$_2$Ph, C(O)NHMe, C(O)NMe$_2$, C(O)NHEt, C(O)NEt$_2$, C(O)NHPh, C(O)NHCH$_2$Ph, the acyl residues of C5-C20 carboxylic acids optionally containing 1-3 multiple bonds, and the acyl residues of the amino acids glycine, alanine, valine, leucine, iso-leucine, serine, threonine, cysteine, methionine, proline, asparagine, glutamine, aspartic acid, glutamic acid, lysine, arginine, histidine, phenylalanine, tyrosine, and tryptophan, and optionally substituted 1-3 times by substituents chosen from the group comprising Me, Et, OMe, OEt, SMe, S(O)Me, S(O)$_2$Me, S(O)$_2$NMe$_2$, CF$_3$, OCF$_3$, F, Cl, OH, CO$_2$H, CO$_2$Me, CO$_2$Et, C(O)NH$_2$, C(O)NMe$_2$, NH$_2$, NH$_3$$^+$, NMe$_2$, NMe$_3$$^+$, NHC(O)Me, NC(=NH)NH$_2$, OS(O)$_2$OH, S(O)$_2$OH, OP(O)(OH)$_2$, and P(O)(OH)$_2$;
R5 and R6 are independently chosen from the group comprising H, Me, Et, iso-Pr, tert-Bu, OMe, OEt, O-iso-Pr, SMe, S(O)Me, S(O)$_2$Me, CF$_3$, OCF$_3$, F, Cl, Br, I, and CN, or R5 and R6 represents OCH$_2$O; and
X is —CH=CH—, or S,
or pharmaceutically acceptable salts of the compounds of the general formula I,
with the provisio that compound I is not chosen from the group comprising
N-phenyl-1,2-dihydro-4-hydroxy-1-methyl-2-oxo-quinoline-3-carboxamide,
N-(4-methylphenyl)-1,2-dihydro-4-hydroxy-1-methyl-2-oxo-quinoline-3-carboxamide,
N-(4-methoxyphenyl)-1,2-dihydro-4-hydroxy-1-methyl-2-oxo-quinoline-3-carboxamide, N-(4-ethoxyphenyl)-1,2-dihydro-4-hydroxy-1-methyl-2-oxo-quinoline-3-carboxamide,
N-(4-trifluoromethoxyphenyl)-1,2-dihydro-4-hydroxy-1-methyl-2-oxo-quinoline-3-carboxamide,
N-(4-chlorophenyl)-1,2-dihydro-4-hydroxy-1-methyl-2-oxo-quinoline-3-carboxamide,
N-(4-bromophenyl)-1,2-dihydro-4-hydroxy-1-methyl-2-oxo-quinoline-3-carboxamide,
N-(3,4-dichlorophenyl)-1,2-dihydro-4-hydroxy-1-methyl-2-oxo-3-quinoline-3-carboxamide,
N-(3,5-dimethylphenyl)-1,2-dihydro-4-hydroxy-1-methyl-2-oxo-quinoline-3-carboxamide,
N-(3-methylphenyl)-1,2-dihydro-4-hydroxy-1-methyl-2-oxo-quinoline-3-carboxamide,
N-(3-chlorophenyl)-1,2-dihydro-4-hydroxy-1-methyl-2-oxo-quinoline-3-carboxamide,
N-(3-methoxyphenyl)-1,2-dihydro-4-hydroxy-1-methyl-2-oxo-quinoline-3-carboxamide,
N-(3-methylthiophenyl)-1,2-dihydro-4-hydroxy-1-methyl-2-oxo-quinoline-3-carboxamide,
N-(3-trifluoromethylphenyl)-1,2-dihydro-4-hydroxy-1-methyl-2-oxo-quinoline-3-carboxamide,
N-(3-bromophenyl)-1,2-dihydro-4-hydroxy-1-methyl-2-oxo-quinoline-3-carboxamide,
N-(3,4-methylenedioxo)-1,2-dihydro-4-hydroxy-1-methyl-2-oxo-quinoline-3-carboxamide,
N-phenyl-5-chloro-1,2-dihydro-4-hydroxy-1-methyl-2-oxo-quinoline-3-carboxamide,
N-phenyl-5-fluoro-1,2-dihydro-4-hydroxy-1-methyl-2-oxo-quinoline-3-carboxamide,
N-phenyl-1,2-dihydro-4-hydroxy-1,6-dimethyl-2-oxo-quinoline-3-carboxamide,
N-phenyl-1,2-dihydro-4-hydroxy-6-methoxy-1-methyl-2-oxo-quinoline-3-carboxamide,
N-phenyl-1,2-dihydro-4-hydroxy-1-methyl-6-methylthio-2-oxo-quinoline-3-carboxamide, and
N-phenyl-6-chloro-1,2-dihydro-4-hydroxy-1-methyl-2-oxo-quinoline-3-carboxamide.

In one embodiment of the present invention,
A, B and C are independently chosen from the group comprising H, Me, OMe, $CF_3$, $OCF_3$, F, Cl, and Br, or A and B represents $OCH_2O$ and C is H; and
R5 and R6 are independently chosen from the group comprising H, Me, Et, OMe, SMe, S(O)Me, $CF_3$, $OCF_3$, F, Cl, and Br, or R5 and R6 represents $OCH_2O$.

In a further embodiment,
A, B and C are independently chosen from the group comprising Me, OMe, $CF_3$, $OCF_3$, F, and Cl, or A and B represents $OCH_2O$ and C is H; and
R5 and R6 are independently chosen from the group comprising Me, Et, OMe, SMe, S(O)Me, $CF_3$, F, and Cl, or R5 and R6 represents $OCH_2O$.

In one preferred embodiment,
RN is chosen from the group comprising H, C(O)Me, C(O)Et, C(O)Pr, C(O)CH(Me)$_2$, C(O)C(Me)$_3$, C(O)Ph, C(O)CH$_2$Ph, CO$_2$Me, CO$_2$Et, and optionally substituted 1-3 times by substituents chosen from the group comprising Me, Et, OMe, OEt, SMe, S(O)Me, S(O)$_2$Me, S(O)$_2$NMe$_2$, $CF_3$, $OCF_3$, F, Cl, OH, CO$_2$H, CO$_2$Me, CO$_2$Et, C(O)NH$_2$, C(O)NMe$_2$, NH$_2$, NH$_3^+$, NMe$_2$, NMe$_3^+$, NHC(O)Me, NC(=NH)NH$_2$, OS(O)$_2$OH, S(O)$_2$OH, OP(O)(OH)$_2$, and P(O)(OH)$_2$; and,
R4 is RN, or when RN is H, then R4 is chosen from the group comprising P(O)(OH)$_2$, P(O)(OMe)$_2$, P(O)(OEt)$_2$, P(O)(OPh)$_2$, P(O)(OCH$_2$Ph)$_2$, C(O)Me, C(O)Et, C(O)Pr, C(O)CH(Me)$_2$, C(O)C(Me)$_3$, C(O)Ph, C(O)CH$_2$Ph, CO$_2$Me, CO$_2$Et, C(O)NHMe, C(O)NMe$_2$, C(O)NHEt, C(O)NEt$_2$, the acyl residues of C5-C20 carboxylic acids optionally containing 1-3 multiple bonds, and the acyl residues of the amino acids glycine, alanine, valine, leucine, iso-leucine, serine, threonine, cysteine, methionine, proline, asparagine, glutamine, aspartic acid, glutamic acid, lysine, arginine, histidine, phenylalanine, tyrosine, and tryptophan, and optionally substituted 1-3 times by substituents chosen from the group comprising Me, Et, OMe, OEt, SMe, S(O)Me, S(O)$_2$Me, S(O)$_2$NMe$_2$, $CF_3$, $OCF_3$, F, Cl, OH, CO$_2$H, CO$_2$Me, CO$_2$Et, C(O)NH$_2$, C(O)NMe$_2$, NH$_2$, NH$_3^+$, NMe$_2$, NMe$_3^+$, NHC(O)Me, NC(=NH)NH$_2$, OS(O)$_2$OH, S(O)$_2$OH, OP(O)(OH)$_2$, and P(O)(OH)$_2$; with the provisio that R4 is not H.

In a further preferred embodiment,
RN is chosen from the group comprising C(O)Me, C(O)Et, C(O)Pr, C(O)CH(Me)$_2$, C(O)C(Me)$_3$, C(O)Ph, CO$_2$Me, and CO$_2$Et; and R4 is RN.

In another further preferred embodiment,
RN is H; and
R4 is chosen from the group comprising P(O)(OH)$_2$, P(O)(OMe)$_2$, P(O)(OEt)$_2$, P(O)(OPh)$_2$, P(O)(OCH$_2$Ph)$_2$, C(O)Me, C(O)Et, C(O)Pr, C(O)CH(Me)$_2$, C(O)C(Me)$_3$, C(O)Ph, C(O)CH$_2$Ph, CO$_2$Me, CO$_2$Et, C(O)NHMe, C(O)NMe$_2$, C(O)NHEt, C(O)NEt$_2$, the acyl residues of C5-C20 carboxylic acids optionally containing 1-3 multiple bonds, and the acyl residues of the amino acids glycine, alanine, valine, leucine, iso-leucine, serine, threonine, cysteine, methionine, proline, asparagine, glutamine, aspartic acid, glutamic acid, lysine, arginine, histidine, phenylalanine, tyrosine, and tryptophan, and optionally substituted 1-3 times by substituents chosen from the group comprising Me, Et, OMe, OEt, SMe, S(O)Me, S(O)$_2$Me, S(O)$_2$NMe$_2$, $CF_3$, $OCF_3$, F, Cl, OH, CO$_2$H, CO$_2$Me, CO$_2$Et, C(O)NH$_2$, C(O)NMe$_2$, NH$_2$, NH$_3^+$, NMe$_2$, NMe$_3^+$, NHC(O)Me, NC(=NH)NH$_2$, OS(O)$_2$OH, S(O)$_2$OH, OP(O)(OH)$_2$, and P(O)(OH)$_2$.

In yet another further preferred embodiment,
RN is H; and
R4 is H.

In another embodiment of the present invention,
X is S.

In a preferred embodiment,
A, B and C are independently chosen from the group comprising H, Me, OMe, $CF_3$, $OCF_3$, F, Cl, and Br, or A and B represents $OCH_2O$ and C is H;
R5 is chosen from the group comprising H, Me, Et, $CF_3$, Cl, and Br;
R6 is H; and
X is S.

In yet another embodiment the new compound described above is chosen from the group comprising
N-acetyl-N-phenyl-4-acetoxy-1,2-dihydro-1-methyl-2-oxo-quinoline-3-carboxamide,
N-phenyl-4-acetoxy-1,2-dihydro-1-methyl-2-oxo-quinoline-3-carboxamide,
N-iso-butyryl-N-phenyl-4-iso-butyryloxy-1,2-dihydro-1-methyl-2-oxo-quinoline-3-carboxamide,
N-phenyl-4-iso-butyryloxy-1,2-dihydro-1-methyl-2-oxo-quinoline-3-carboxamide,
N-benzoyl-N-phenyl-4-benzoyloxy-1,2-dihydro-1-methyl-2-oxo-quinoline-3-carboxamide,
N-phenyl-4-benzoyloxy-1,2-dihydro-1-methyl-2-oxo-quinoline-3-carboxamide,
N-ethoxycarbonyl-N-phenyl-4-ethoxycarbonyloxy-1,2-dihydro-1-methyl-2-oxo-quinoline-3-carboxamide,
N-phenyl-4-diethylphosphoryloxy-1,2-dihydro-1-methyl-2-oxo-quinoline-3-carboxamide,
N-acetyl-N-(4-methylphenyl)-4-acetoxy-1,2-dihydro-1-methyl-2-oxo-quinoline-3-carboxamide, N-(4-methylphenyl)-4-acetoxy-1,2-dihydro-1-methyl-2-oxo-quinoline-3-carboxamide,
N-iso-butyryl-N-(4-methylphenyl)-4-iso-butyryloxy-1,2-dihydro-1-methyl-2-oxo-quinoline-3-carboxamide,
N-(4-methylphenyl)-4-iso-butyryloxy-1,2-dihydro-1-methyl-2-oxo-quinoline-3-carboxamide,
N-benzoyl-N-(4-methylphenyl)-4-benzoyloxy-1,2-dihydro-1-methyl-2-oxo-quinoline-3-carboxamide,
N-ethoxycarbonyl-N-(4-methylphenyl)-4-ethoxycarbonyloxy-1,2-dihydro-1-methyl-2-oxo-quinoline-3-carboxamide,
N-(4-fluorophenyl)-1,2-dihydro-4-hydroxy-1-methyl-2-oxo-quinoline-3-carboxamide,
N-acetyl-N-(4-fluorophenyl)-4-acetoxy-1,2-dihydro-1-methyl-2-oxo-quinoline-3-carboxamide,
N-(4-fluorophenyl)-4-acetoxy-1,2-dihydro-1-methyl-2-oxo-quinoline-3-carboxamide,
N-iso-butyryl-N-(4-fluorophenyl)-4-iso-butyryloxy-1,2-dihydro-1-methyl-2-oxo-quinoline-3-carboxamide,
N-(4-fluorophenyl)-4-iso-butyryloxy-1,2-dihydro-1-methyl-2-oxo-quinoline-3-carboxamide,
N-benzoyl-N-(4-fluorophenyl)-4-benzoyloxy-1,2-dihydro-1-methyl-2-oxo-quinoline-3-carboxamide,
N-ethoxycarbonyl-N-(4-fluorophenyl)-4-ethoxycarbonyloxy-1,2-dihydro-1-methyl-2-oxo-quinoline-3-carboxamide,
N-acetyl-N-(4-chlorophenyl)-4-acetoxy-1,2-dihydro-1-methyl-2-oxo-quinoline-3-carboxamide,
N-(4-chlorophenyl)-4-acetoxy-1,2-dihydro-1-methyl-2-oxo-quinoline-3-carboxamide,
N-iso-butyryl-N-(4-chlorophenyl)-4-iso-butyryloxy-1,2-dihydro-1-methyl-2-oxo-quinoline-3-carboxamide,
N-(4-chlorophenyl)-4-iso-butyryloxy-1,2-dihydro-1-methyl-2-oxo-quinoline-3-carboxamide,
N-benzoyl-N-(4-chlorophenyl)-4-benzoyloxy-1,2-dihydro-1-methyl-2-oxo-quinoline-3-carboxamide,
N-(4-chlorophenyl)-N-ethoxycarbonyl-4-ethoxycarbonyloxy-1,2-dihydro-1-methyl-2-oxo-quinoline-3-carboxamide,
N-acetyl-N-(4-methoxyphenyl)-4-acetoxy-1,2-dihydro-1-methyl-2-oxo-quinoline-3-carboxamide,
N-(4-methoxyphenyl)-4-acetoxy-1,2-dihydro-1-methyl-2-oxo-quinoline-3-carboxamide,
N-iso-butyryl-N-(4-methoxyphenyl)-4-iso-butyryloxy-1,2-dihydro-1-methyl-2-oxo-quinoline-3-carboxamide,
N-(4-methoxyphenyl)-4-iso-butyryloxy-1,2-dihydro-1-methyl-2-oxo-quinoline-3-carboxamide,
N-benzoyl-N-(4-methoxyphenyl)-4-benzoyloxy-1,2-dihydro-1-methyl-2-oxo-quinoline-3-carboxamide,
N-ethoxycarbonyl-N-(4-methoxyphenyl)-4-ethoxycarbonyloxy-1,2-dihydro-1-methyl-2-oxo-quinoline-3-carboxamide,
N-(4-trifluoromethylphenyl)-1,2-dihydro-4-hydroxy-1-methyl-2-oxo-quinoline-3-carboxamide,
N-acetyl-N-(4-trifluoromethylphenyl)-4-acetoxy-1,2-dihydro-1-methyl-2-oxo-quinoline-3-carboxamide,
N-(4-trifluoromethylphenyl)-4-acetoxy-1,2-dihydro-1-methyl-2-oxo-quinoline-3-carboxamide,
N-iso-butyryl-N-(4-trifluoromethylphenyl)-4-iso-butyryloxy-1,2-dihydro-1-methyl-2-oxo-quinoline-3-carboxamide,
N-benzoyl-N-(4-trifluoromethylphenyl)-4-benzoyloxy-1,2-dihydro-1-methyl-2-oxo-quinoline-3-carboxamide,
N-ethoxycarbonyl-N-(4-trifluoromethylphenyl)-4-ethoxycarbonyloxy-1,2-dihydro-1-methyl-2-oxo-quinoline-3-carboxamide,
N-acetyl-N-(4-trifluoromethoxyphenyl)-4-acetoxy-1,2-dihydro-1-methyl-2-oxo-quinoline-3-carboxamide,
N-(4-trifluoromethoxyphenyl)-4-acetoxy-1,2-dihydro-1-methyl-2-oxo-quinoline-3-carboxamide,
N-(3,4-difluorophenyl)-1,2-dihydro-4-hydroxy-1-methyl-2-oxo-quinoline-3-carboxamide,
N-acetyl-N-(3,4-difluorophenyl)-4-acetoxy-1,2-dihydro-1-methyl-2-oxo-quinoline-3-carboxamide,
N-(3,4-difluorophenyl)-4-acetoxy-1,2-dihydro-1-methyl-2-oxo-quinoline-3-carboxamide,
N-(3,5-di-(trifluoromethyl)phenyl)-1,2-dihydro-4-hydroxy-1-methyl-2-oxo-quinoline-3-carboxamide,
N-(4-methylthiophenyl)-1,2-dihydro-4-hydroxy-1-methyl-2-oxo-quinoline-3-carboxamide,
N-acetyl-N-(3,4-methylenedioxyphenyl)-4-acetoxy-1,2-dihydro-1-methyl-2-oxo-quinoline-3-carboxamide,
N-(4-methylenedioxyphenyl)-4-acetoxy-1,2-dihydro-1-methyl-2-oxo-quinoline-3-carboxamide,
N-phenyl-1,2-dihydro-4-hydroxy-1,5-dimethyl-2-oxo-quinoline-3-carboxamide,
N-acetyl-N-phenyl-4-acetoxy-1,2-dihydro-1,5-dimethyl-2-oxo-quinoline-3-carboxamide,
N-phenyl-4-acetoxy-1,2-dihydro-1,5-dimethyl-2-oxo-quinoline-3-carboxamide,
N-(4-chlorophenyl)-1,2-dihydro-4-hydroxy-1,5-dimethyl-2-oxo-quinoline-3-carboxamide,
N-acetyl-N-(4-chlorophenyl)-4-acetoxy-1,2-dihydro-1,5-dimethyl-2-oxo-quinoline-3-carboxamide,
N-(4-chlorophenyl)-4-acetoxy-1,2-dihydro-1,5-dimethyl-2-oxo-quinoline-3-carboxamide,
N-(4-methoxyphenyl)-1,2-dihydro-4-hydroxy-1,5-dimethyl-2-oxo-quinoline-3-carboxamide,
N-acetyl-N-(4-methoxyphenyl)-4-acetoxy-1,2-dihydro-1,5-dimethyl-2-oxo-quinoline-3-carboxamide,
N-(4-methoxyphenyl)-4-acetoxy-1,2-dihydro-1,5-dimethyl-2-oxo-quinoline-3-carboxamide,
N-phenyl-5-ethyl-1,2-dihydro-4-hydroxy-1-methyl-2-oxo-quinoline-3-carboxamide,
N-acetyl-N-phenyl-4-acetoxy-5-ethyl-1,2-dihydro-1-methyl-2-oxo-quinoline-3-carboxamide,
N-phenyl-4-acetoxy-5-ethyl-1,2-dihydro-1-methyl-2-oxo-quinoline-3-carboxamide,
N-iso-butyryl-N-phenyl-4-iso-butyryloxy-5-ethyl-1,2-dihydro-1-methyl-2-oxo-quinoline-3-carboxamide,
N-phenyl-4-iso-butyryloxy-5-ethyl-1,2-dihydro-1-methyl-2-oxo-quinoline-3-carboxamide,
N-benzoyl-N-phenyl-4-benzoyloxy-5-ethyl-1,2-dihydro-1-methyl-2-oxo-quinoline-3-carboxamide,
N-phenyl-4-benzoyloxy-5-ethyl-1,2-dihydro-1-methyl-2-oxo-quinoline-3-carboxamide,
N-ethoxycarbonyl-N-phenyl-4-ethoxycarbonyloxy-5-ethyl-1,2-dihydro-1-methyl-2-oxo-quinoline-3-carboxamide,
N-phenyl-4-diethylphosphoryloxy-5-ethyl-1,2-dihydro-1-methyl-2-oxo-quinoline-3-carboxamide,
N-(4-chlorophenyl)-5-ethyl-1,2-dihydro-4-hydroxy-1-methyl-2-oxo-quinoline-3-carboxamide,
N-acetyl-N-(4-chlorophenyl)-4-acetoxy-5-ethyl-1,2-dihydro-1-methyl-2-oxo-quinoline-3-carboxamide,
N-(4-chlorophenyl)-4-acetoxy-5-ethyl-1,2-dihydro-1-methyl-2-oxo-quinoline-3-carboxamide,
N-(4-chlorophenyl)-4-iso-butyryloxy-5-ethyl-1,2-dihydro-1-methyl-2-oxo-quinoline-3-carboxamide,
N-benzoyl-N-(4-chlorophenyl)-4-benzoyloxy-5-ethyl-1,2-dihydro-1-methyl-2-oxo-quinoline-3-carboxamide,
N-(4-methoxyphenyl)-5-ethyl-1,2-dihydro-4-hydroxy-1-methyl-2-oxo-quinoline-3-carboxamide, N-acetyl-N-(4-methoxyphenyl)-4-acetoxy-5-ethyl-1,2-dihydro-1-methyl-2-oxo-quinoline-3-carboxamide,
N-(4-methoxyphenyl)-4-acetoxy-5-ethyl-1,2-dihydro-1-methyl-2-oxo-quinoline-3-carboxamide,
N-phenyl-1,2-dihydro-4-hydroxy-1-methyl-2-oxo-5-trifluoromethyl-quinoline-3-carboxamide,
N-acetyl-N-phenyl-4-acetoxy-1,2-dihydro-1-methyl-2-oxo-5-trifluoromethyl-quinoline-3-carboxamide,
N-phenyl-4-acetoxy-1,2-dihydro-1-methyl-2-oxo-5-trifluoromethyl-quinoline-3-carboxamide,
N-phenyl-1,2-dihydro-4-hydroxy-5-methoxy-1-methyl-2-oxo-quinoline-3-carboxamide,
N-acetyl-N-phenyl-4-acetoxy-1,2-dihydro-5-methoxy-1-methyl-2-oxo-quinoline-3-carboxamide,
N-phenyl-4-acetoxy-1,2-dihydro-5-methoxy-1-methyl-2-oxo-quinoline-3-carboxamide,
N-iso-butyryl-N-phenyl-4-iso-butyryloxy-1,2-dihydro-5-methoxy-1-methyl-2-oxo-quinoline-3-carboxamide,
N-phenyl-4-iso-butyryloxy-1,2-dihydro-5-methoxy-1-methyl-2-oxo-quinoline-3-carboxamide,
N-benzoyl-N-phenyl-4-benzoyloxy-1,2-dihydro-5-methoxy-1-methyl-2-oxo-quinoline-3-carboxamide,
N-phenyl-4-benzoyloxy-1,2-dihydro-5-methoxy-1-methyl-2-oxo-quinoline-3-carboxamide,
N-(4-fluorophenyl)-1,2-dihydro-4-hydroxy-5-methoxy-1-methyl-2-oxo-quinoline-3-carboxamide,
N-acetyl-N-(4-fluorophenyl)-4-acetoxy-1,2-dihydro-5-methoxy-1-methyl-2-oxo-quinoline-3-carboxamide,
N-(4-fluorophenyl)-4-acetoxy-1,2-dihydro-5-methoxy-1-methyl-2-oxo-quinoline-3-carboxamide,
N-iso-butyryl-N-(4-fluorophenyl)-4-iso-butyryloxy-1,2-dihydro-5-methoxy-1-methyl-2-oxo-quinoline-3-carboxamide,
N-(4-fluorophenyl)-4-iso-butyryloxy-1,2-dihydro-5-methoxy-1-methyl-2-oxo-quinoline-3-carboxamide,
N-benzoyl-N-(4-fluorophenyl)-4-benzoyloxy-1,2-dihydro-5-methoxy-1-methyl-2-oxo-quinoline-3-carboxamide,
N-(4-fluorophenyl)-4-benzoyloxy-1,2-dihydro-5-methoxy-1-methyl-2-oxo-quinoline-3-carboxamide,
N-(4-trifluoromethylphenyl)-1,2-dihydro-4-hydroxy-5-methoxy-1-methyl-2-oxo-quinoline-3-carboxamide,
N-acetyl-N-(4-trifluoromethylphenyl)-4-acetoxy-1,2-dihydro-5-methoxy-1-methyl-2-oxo-quinoline-3-carboxamide,
N-(4-trifluoromethylphenyl)-4-acetoxy-1,2-dihydro-5-methoxy-1-methyl-2-oxo-quinoline-3-carboxamide,
N-iso-butyryl-N-(4-trifluoromethylphenyl)-4-iso-butyryloxy-1,2-dihydro-5-methoxy-1-methyl-2-oxo-quinoline-3-carboxamide,
N-(4-trifluoromethylphenyl)-4-iso-butyryloxy-1,2-dihydro-5-methoxy-1-methyl-2-oxo-quinoline-3-carboxamide,
N-benzoyl-N-(4-trifluoromethylphenyl)-4-benzoyloxy-1,2-dihydro-5-methoxy-1-methyl-2-oxo-quinoline-3-carboxamide,
N-(4-trifluoromethylphenyl)-4-benzoyloxy-1,2-dihydro-5-methoxy-1-methyl-2-oxo-quinoline-3-carboxamide,
N-ethoxycarbonyl-N-(4-trifluoromethylphenyl)-4-ethoxycarbonyloxy-1,2-dihydro-5-methoxy-1-methyl-2-oxo-quinoline-3-carboxamide,
N-(4-trifluoromethylphenyl)-4-diethylphosphoryloxy-1,2-dihydro-5-methoxy-1-methyl-2-oxo-quinoline-3-carboxamide,
N-acetyl-N-phenyl-4-acetoxy-5-fluoro-1,2-dihydro-1-methyl-2-oxo-quinoline-3-carboxamide,
N-phenyl-4-acetoxy-5-fluoro-1,2-dihydro-1-methyl-2-oxo-quinoline-3-carboxamide,
N-acetyl-N-phenyl-4-acetoxy-5-chloro-1,2-dihydro-1-methyl-2-oxo-quinoline-3-carboxamide,
N-phenyl-4-acetoxy-5-chloro-1,2-dihydro-1-methyl-2-oxo-quinoline-3-carboxamide,
N-iso-butyryl-N-phenyl-4-iso-butyryloxy-5-chloro-1,2-dihydro-1-methyl-2-oxo-quinoline-3-carboxamide,
N-phenyl-4-iso-butyryloxy-5-chloro-1,2-dihydro-1-methyl-2-oxo-quinoline-3-carboxamide,
N-benzoyl-N-phenyl-4-benzoyloxy-5-chloro-1,2-dihydro-1-methyl-2-oxo-quinoline-3-carboxamide,
N-phenyl-4-benzoyloxy-5-chloro-1,2-dihydro-1-methyl-2-oxo-quinoline-3-carboxamide,
N-ethoxycarbonyl-N-phenyl-4-ethoxycarbonyloxy-5-chloro-1,2-dihydro-1-methyl-2-oxo-quinoline-3-carboxamide,
N-phenyl-4-diethylphosphoryloxy-5-chloro-1,2-dihydro-1-methyl-2-oxo-quinoline-3-carboxamide,
N-(4-methylphenyl)-5-chloro-1,2-dihydro-4-hydroxy-1-methyl-2-oxo-quinoline-3-carboxamide,
N-acetyl-N-(4-methylphenyl)-4-acetoxy-5-chloro-1,2-dihydro-1-methyl-2-oxo-quinoline-3-carboxamide,
N-(4-methylphenyl)-4-acetoxy-5-chloro-1,2-dihydro-1-methyl-2-oxo-quinoline-3-carboxamide,
N-ethoxycarbonyl-N-(4-methylphenyl)-5-chloro-4-ethoxycarbonyloxy-1,2-dihydro-1-methyl-2-oxo-quinoline-3-carboxamide,
N-(4-methoxyphenyl)-5-chloro-1,2-dihydro-4-hydroxy-1-methyl-2-oxo-quinoline-3-carboxamide,
N-acetyl-N-(4-methoxyphenyl)-4-acetoxy-5-chloro-1,2-dihydro-1-methyl-2-oxo-quinoline-3-carboxamide,
N-iso-butyryl-N-(4-methoxyphenyl)-4-iso-butyryloxy-5-chloro-1,2-dihydro-1-methyl-2-oxo-quinoline-3-carboxamide,
N-(4-methoxyphenyl)-4-acetoxy-5-chloro-1,2-dihydro-1-methyl-2-oxo-quinoline-3-carboxamide,
N-(4-chlorophenyl)-5-chloro-1,2-dihydro-4-hydroxy-1-methyl-2-oxo-quinoline-3-carboxamide,
N-acetyl-N-(4-chlorophenyl)-4-acetoxy-5-chloro-1,2-dihydro-1-methyl-2-oxo-quinoline-3-carboxamide,
N-(4-chlorophenyl)-4-acetoxy-5-chloro-1,2-dihydro-1-methyl-2-oxo-quinoline-3-carboxamide,
N-phenyl-5-bromo-1,2-dihydro-4-hydroxy-1-methyl-2-oxo-quinoline-3-carboxamide,
N-acetyl-N-phenyl-4-acetoxy-5-bromo-1,2-dihydro-1-methyl-2-oxo-quinoline-3-carboxamide,
N-phenyl-4-acetoxy-5-bromo-1,2-dihydro-1-methyl-2-oxo-quinoline-3-carboxamide,
N-phenyl-1,2-dihydro-4-hydroxy-1-methyl-5-methylthio-2-oxo-quinoline-3-carboxamide,
N-acetyl-N-phenyl-4-acetoxy-1,2-dihydro-1-methyl-5-methylthio-2-oxo-quinoline-3-carboxamide,
N-phenyl-4-acetoxy-1,2-dihydro-1-methyl-5-methylthio-2-oxo-quinoline-3-carboxamide,
N-phenyl-1,2-dihydro-4-hydroxy-5,6-methylenedioxy-1-methyl-2-oxo-quinoline-3-carboxamide,
N-acetyl-N-phenyl-4-acetoxy-1,2-dihydro-5,6-methylenedioxy-1-methyl-2-oxo-quinoline-3-carboxamide,
N-phenyl-4-acetoxy-1,2-dihydro-5,6-methylenedioxy-1-methyl-2-oxo-quinoline-3-carboxamide,
N-(4-methoxyphenyl)-1,2-dihydro-4-hydroxy-5,6-methylenedioxy-1-methyl-2-oxo-quinoline-3-carboxamide,
N-(4-methoxyphenyl)-N-phenyl-4-acetoxy-1,2-dihydro-5,6-methylenedioxy-1-methyl-2-oxo-quinoline-3-carboxamide,
N-(4-methoxyphenyl)-4-acetoxy-1,2-dihydro-5,6-methylenedioxy-1-methyl-2-oxo-quinoline-3-carboxamide, N-(4-chlorophenyl)-1,2-dihydro-4-hydroxy-5,6-methylenedioxy-1-methyl-2-oxo-quinoline-3-carboxamide,
N-(4-chlorophenyl)-N-phenyl-4-acetoxy-1,2-dihydro-5,6-methylenedioxy-1-methyl-2-oxo-quinoline-3-carboxamide,
N-(4-chlorophenyl)-4-acetoxy-1,2-dihydro-5,6-methylenedioxy-1-methyl-2-oxo-quinoline-3-carboxamide,
N-acetyl-N-phenyl-4-acetoxy-1,2-dihydro-1,6-dimethyl-2-oxo-quinoline-3-carboxamide,
N-phenyl-4-acetoxy-1,2-dihydro-1,6-dimethyl-2-oxo-quinoline-3-carboxamide,
N-phenyl-1,2-dihydro-4-hydroxy-1-methyl-2-oxo-6-trifluoromethyl-quinoline-3-carboxamide,
N-acetyl-N-phenyl-4-acetoxy-1,2-dihydro-1-methyl-2-oxo-6-trifluoromethyl-quinoline-3-carboxamide,
N-phenyl-4-acetoxy-1,2-dihydro-1-methyl-2-oxo-6-trifluoromethyl-quinoline-3-carboxamide,
N-acetyl-N-phenyl-4-acetoxy-1,2-dihydro-6-methoxy-1-methyl-2-oxo-quinoline-3-carboxamide,
N-phenyl-4-acetoxy-1,2-dihydro-6-methoxy-1-methyl-2-oxo-quinoline-3-carboxamide,
N-iso-butyryl-N-phenyl-4-iso-butyryloxy-1,2-dihydro-6-methoxy-1-methyl-2-oxo-quinoline-3-carboxamide,
N-phenyl-4-iso-butyryloxy-1,2-dihydro-6-methoxy-1-methyl-2-oxo-quinoline-3-carboxamide,
N-benzoyl-N-phenyl-4-benzoyloxy-1,2-dihydro-6-methoxy-1-methyl-2-oxo-quinoline-3-carboxamide,
N-phenyl-4-benzoyloxy-1,2-dihydro-6-methoxy-1-methyl-2-oxo-quinoline-3-carboxamide,
N-ethoxycarbonyl-N-phenyl-4-ethoxycarbonyloxy-1,2-dihydro-6-methoxy-1-methyl-2-oxo-quinoline-3-carboxamide,
N-phenyl-4-diethylphosphoryloxy-1,2-dihydro-6-methoxy-1-methyl-2-oxo-quinoline-3-carboxamide,
N-(4-fluorophenyl)-1,2-dihydro-4-hydroxy-6-methoxy-1-methyl-2-oxo-quinoline-3-carboxamide,
N-acetyl-N-(4-fluorophenyl)-4-acetoxy-1,2-dihydro-6-methoxy-1-methyl-2-oxo-quinoline-3-carboxamide,
N-(4-fluorophenyl)-4-acetoxy-1,2-dihydro-6-methoxy-1-methyl-2-oxo-quinoline-3-carboxamide,
N-iso-butyryl-N-(4-fluorophenyl)-4-iso-butyryloxy-1,2-dihydro-6-methoxy-1-methyl-2-oxo-quinoline-3-carboxamide,
N-benzoyl-N-(4-fluorophenyl)-4-benzoyloxy-1,2-dihydro-6-methoxy-1-methyl-2-oxo-quinoline-3-carboxamide,
N-ethoxycarbonyl-N-(4-fluorophenyl)-4-ethoxycarbonyloxy-1,2-dihydro-6-methoxy-1-methyl-2-oxo-quinoline-3-carboxamide,
N-(4-chlorophenyl)-1,2-dihydro-4-hydroxy-6-methoxy-1-methyl-2-oxo-quinoline-3-carboxamide,
N-acetyl-N-(4-chlorophenyl)-4-acetoxy-1,2-dihydro-6-methoxy-1-methyl-2-oxo-quinoline-3-carboxamide,
N-(4-chlorophenyl)-4-acetoxy-1,2-dihydro-6-methoxy-1-methyl-2-oxo-quinoline-3-carboxamide,
N-iso-butyryl-N-(4-chlorophenyl)-4-iso-butyryloxy-1,2-dihydro-6-methoxy-1-methyl-2-oxo-quinoline-3-carboxamide,
N-benzoyl-N-(4-chlorophenyl)-4-benzoyloxy-1,2-dihydro-6-methoxy-1-methyl-2-oxo-quinoline-3-carboxamide,
N-(4-chlorophenyl)-N-ethoxycarbonyl-4-ethoxycarbonyloxy-1,2-dihydro-6-methoxy-1-methyl-2-oxo-quinoline-3-carboxamide,
N-phenyl-1,2-dihydro-4-hydroxy-1-methyl-2-oxo-6-trifluoromethoxy-quinoline-3-carboxamide,
N-acetyl-N-phenyl-4-acetoxy-1,2-dihydro-1-methyl-2-oxo-6-trifluoromethoxy-quinoline-3-carboxamide,
N-phenyl-4-acetoxy-1,2-dihydro-1-methyl-2-oxo-6-trifluoromethoxy-quinoline-3-carboxamide,
N-phenyl-6-fluoro-1,2-dihydro-4-hydroxy-1-methyl-2-oxo-quinoline-3-carboxamide,
N-acetyl-N-phenyl-4-acetoxy-6-fluoro-1,2-dihydro-1-methyl-2-oxo-quinoline-3-carboxamide,
N-phenyl-4-acetoxy-6-fluoro-1,2-dihydro-1-methyl-2-oxo-quinoline-3-carboxamide,
N-acetyl-N-phenyl-4-acetoxy-6-chloro-1,2-dihydro-1-methyl-2-oxo-quinoline-3-carboxamide,
N-phenyl-4-acetoxy-6-chloro-1,2-dihydro-1-methyl-2-oxo-quinoline-3-carboxamide,
N-iso-butyryl-N-phenyl-4-iso-butyryloxy-6-chloro-1,2-dihydro-1-methyl-2-oxo-quinoline-3-carboxamide,
N-phenyl-4-iso-butyryloxy-6-chloro-1,2-dihydro-1-methyl-2-oxo-quinoline-3-carboxamide,
N-benzoyl-N-phenyl-4-benzoyloxy-6-chloro-1,2-dihydro-1-methyl-2-oxo-quinoline-3-carboxamide,
N-phenyl-4-benzoyloxy-6-chloro-1,2-dihydro-1-methyl-2-oxo-quinoline-3-carboxamide,
N-ethoxycarbonyl-N-phenyl-4-ethoxycarbonyloxy-6-chloro-1,2-dihydro-1-methyl-2-oxo-quinoline-3-carboxamide,
N-phenyl-4-diethylphosphoryloxy-6-chloro-1,2-dihydro-1-methyl-2-oxo-quinoline-3-carboxamide,
N-(4-fluorophenyl)-6-chloro-1,2-dihydro-4-hydroxy-1-methyl-2-oxo-quinoline-3-carboxamide,
N-acetyl-N-(4-fluorophenyl)-4-acetoxy-6-chloro-1,2-dihydro-1-methyl-2-oxo-quinoline-3-carboxamide,
N-(4-fluorophenyl)-4-acetoxy-6-chloro-1,2-dihydro-1-methyl-2-oxo-quinoline-3-carboxamide,
N-n-butyryl-N-(4-fluorophenyl)-4-n-butyryloxy-6-chloro-1,2-dihydro-1-methyl-2-oxo-quinoline-3-carboxamide,
N-iso-butyryl-N-(4-fluorophenyl)-4-iso-butyryloxy-6-chloro-1,2-dihydro-1-methyl-2-oxo-quinoline-3-carboxamide,
N-benzoyl-N-(4-fluorophenyl)-4-benzoyloxy-6-chloro-1,2-dihydro-1-methyl-2-oxo-quinoline-3-carboxamide,
N-ethoxycarbonyl-N-(4-fluorophenyl)-6-chloro-4-ethoxycarbonyloxy-1,2-dihydro-1-methyl-2-oxo-quinoline-3-carboxamide,
N-(4-chlorophenyl)-6-chloro-1,2-dihydro-4-hydroxy-1-methyl-2-oxo-quinoline-3-carboxamide,
N-acetyl-N-(4-chlorophenyl)-4-acetoxy-6-chloro-1,2-dihydro-1-methyl-2-oxo-quinoline-3-carboxamide,
N-(4-chlorophenyl)-4-acetoxy-6-chloro-1,2-dihydro-1-methyl-2-oxo-quinoline-3-carboxamide,
N-n-butyryl-N-(4-chlorophenyl)-4-n-butyryloxy-6-chloro-1,2-dihydro-1-methyl-2-oxo-quinoline-3-carboxamide,
N-iso-butyryl-N-(4-chlorophenyl)-4-iso-butyryloxy-6-chloro-1,2-dihydro-1-methyl-2-oxo-quinoline-3-carboxamide,
N-benzoyl-N-(4-chlorophenyl)-4-benzoyloxy-6-chloro-1,2-dihydro-1-methyl-2-oxo-quinoline-3-carboxamide,
N-(4-chlorophenyl)-N-ethoxycarbonyl-6-chloro-4-ethoxycarbonyloxy-1,2-dihydro-1-methyl-2-oxo-quinoline-3-carboxamide,
N-(4-methoxyphenyl)-6-chloro-1,2-dihydro-4-hydroxy-1-methyl-2-oxo-quinoline-3-carboxamide,
N-acetyl-N-(4-methoxyphenyl)-4-acetoxy-6-chloro-1,2-dihydro-1-methyl-2-oxo-quinoline-3-carboxamide,
N-(4-methoxyphenyl)-4-acetoxy-6-chloro-1,2-dihydro-1-methyl-2-oxo-quinoline-3-carboxamide,
N-n-butyryl-N-(4-methoxyphenyl)-4-n-butyryloxy-6-chloro-1,2-dihydro-1-methyl-2-oxo-quinoline-3-carboxamide, N-iso-butyryl-N-(4-methoxyphenyl)-4-iso-butyryloxy-6-chloro-1,2-dihydro-1-methyl-2-oxo-quinoline-3-carboxamide,
N-benzoyl-N-(4-methoxyphenyl)-4-benzoyloxy-6-chloro-1,2-dihydro-1-methyl-2-oxo-quinoline-3-carboxamide,
N-ethoxycarbonyl-N-(4-methoxyphenyl)-6-chloro-4-ethoxycarbonyloxy-1,2-dihydro-1-methyl-2-oxo-quinoline-3-carboxamide,
N-phenyl-6-bromo-1,2-dihydro-4-hydroxy-1-methyl-2-oxo-quinoline-3-carboxamide,
N-acetyl-N-phenyl-4-acetoxy-6-bromo-1,2-dihydro-1-methyl-2-oxo-quinoline-3-carboxamide,
N-phenyl-4-acetoxy-6-bromo-1,2-dihydro-1-methyl-2-oxo-quinoline-3-carboxamide,
N-acetyl-N-phenyl-4-acetoxy-1,2-dihydro-1-methyl-6-methylthio-2-oxo-quinoline-3-carboxamide,
N-phenyl-4-acetoxy-1,2-dihydro-1-methyl-6-methylthio-2-oxo-quinoline-3-carboxamide,
N-iso-butyryl-N-phenyl-4-iso-butyryloxy-1,2-dihydro-1-methyl-6-methylthio-2-oxo-quinoline-3-carboxamide,
N-phenyl-4-iso-butyryloxy-1,2-dihydro-1-methyl-6-methylthio-2-oxo-quinoline-3-carboxamide,
N-benzoyl-N-phenyl-4-benzoyloxy-1,2-dihydro-1-methyl-6-methylthio-2-oxo-quinoline-3-carboxamide,
N-phenyl-4-benzoyloxy-1,2-dihydro-1-methyl-6-methylthio-2-oxo-quinoline-3-carboxamide,
N-ethoxycarbonyl-N-phenyl-4-ethoxycarbonyloxy-1,2-dihydro-1-methyl-6-methylthio-2-oxo-quinoline-3-carboxamide,
N-phenyl-4-diethylphosphoryloxy-1,2-dihydro-1-methyl-6-methylthio-2-oxo-quinoline-3-carboxamide,
N-(4-fluorophenyl)-1,2-dihydro-4-hydroxy-1-methyl-6-methylthio-2-oxo-quinoline-3-carboxamide,
N-acetyl-N-(4-fluorophenyl)-4-acetoxy-1,2-dihydro-1-methyl-6-methylthio-2-oxo-quinoline-3-carboxamide,
N-(4-fluorophenyl)-4-acetoxy-1,2-dihydro-1-methyl-6-methylthio-2-oxo-quinoline-3-carboxamide,
N-(4-chlorophenyl)-1,2-dihydro-4-hydroxy-1-methyl-6-methylthio-2-oxo-quinoline-3-carboxamide,
N-acetyl-N-(4-chlorophenyl)-4-acetoxy-1,2-dihydro-1-methyl-6-methylthio-2-oxo-quinoline-3-carboxamide,
N-(4-chlorophenyl)-4-acetoxy-1,2-dihydro-1-methyl-6-methylthio-2-oxo-quinoline-3-carboxamide,
N-(4-methoxyphenyl)-1,2-dihydro-4-hydroxy-1-methyl-6-methylthio-2-oxo-quinoline-3-carboxamide,
N-acetyl-N-(4-methoxyphenyl)-4-acetoxy-1,2-dihydro-1-methyl-6-methylthio-2-oxo-quinoline-3-carboxamide,
N-(4-methoxyphenyl)-4-acetoxy-1,2-dihydro-1-methyl-6-methylthio-2-oxo-quinoline-3-carboxamide,
N-acetyl-N-phenyl-1,2-dihydro-4-hydroxy-1-methyl-6-methylsulfinyl-2-oxo-quinoline-3-carboxamide,
N-acetyl-N-phenyl-4-acetoxy-1,2-dihydro-1-methyl-6-methylsulfinyl-2-oxo-quinoline-3-carboxamide,
N-phenyl-4-acetoxy-1,2-dihydro-1-methyl-6-methylsulfinyl-2-oxo-quinoline-3-carboxamide,
N-phenyl-6,7-dihydro-4-hydroxy-7-methyl-6-oxo-thieno[2,3-b]pyridine-5-carboxamide,
N-acetyl-N-phenyl-4-acetoxy-6,7-dihydro-7-methyl-6-oxo-thieno[2,3-b]pyridine-5-carboxamide,
N-phenyl-4-acetoxy-6,7-dihydro-7-methyl-6-oxo-thieno[2,3-b]pyridine-5-carboxamide,
N-phenyl-6,7-dihydro-4-hydroxy-3,7-dimethyl-6-oxo-thieno[2,3-b]pyridine-5-carboxamide,
N-acetyl-N-phenyl-4-acetoxy-6,7-dihydro-3,7-dimethyl-6-oxo-thieno[2,3-b]pyridine-5-carboxamide,
N-phenyl-4-acetoxy-6,7-dihydro-3,7-dimethyl-6-oxo-thieno[2,3-b]pyridine-5-carboxamide,
N-iso-butyryl-N-phenyl-4-iso-butyryloxy-6,7-dihydro-3,7-dimethyl-6-oxo-thieno[2,3-b]pyridine-5-carboxamide,
N-phenyl-4-iso-butyryloxy-6,7-dihydro-3,7-dimethyl-6-oxo-thieno[2,3-b]pyridine-5-carboxamide,
N-benzoyl-N-phenyl-4-benzoyloxy-6,7-dihydro-3,7-dimethyl-6-oxo-thieno[2,3-b]pyridine-5-carboxamide,
N-phenyl-4-benzoyloxy-6,7-dihydro-3,7-dimethyl-6-oxo-thieno[2,3-b]pyridine-5-carboxamide,
N-ethoxycarbonyl-N-phenyl-4-ethoxycarbonyloxy-6,7-dihydro-3,7-dimethyl-6-oxo-thieno[2,3-b]pyridine-5-carboxamide,
N-phenyl-4-diethylphosphoryloxy-6,7-dihydro-3,7-dimethyl-6-oxo-thieno[2,3-b]pyridine-5-carboxamide,
N-(4-fluorophenyl)-6,7-dihydro-4-hydroxy-3,7-dimethyl-6-oxo-thieno[2,3-b]pyridine-5-carboxamide,
N-acetyl-N-(4-fluorophenyl)-4-acetoxy-6,7-dihydro-3,7-dimethyl-6-oxo-thieno[2,3-b]pyridine-5-carboxamide,
N-(4-fluorophenyl)-4-acetoxy-6,7-dihydro-3,7-dimethyl-6-oxo-thieno[2,3-b]pyridine-5-carboxamide,
N-iso-butyryl-N-(4-fluorophenyl)-4-iso-butyryloxy-6,7-dihydro-3,7-dimethyl-6-oxo-thieno[2,3-b]pyridine-5-carboxamide,
N-benzoyl-N-(4-fluorophenyl)-4-benzoyloxy-6,7-dihydro-3,7-dimethyl-6-oxo-thieno[2,3-b]pyridine-5-carboxamide,
N-ethoxycarbonyl-N-(4-fluorophenyl)-4-ethoxycarbonyloxy-6,7-dihydro-3,7-dimethyl-6-oxo-thieno[2,3-b]pyridine-5-carboxamide,
N-(4-chlorophenyl)-6,7-dihydro-4-hydroxy-3,7-dimethyl-6-oxo-thieno[2,3-b]pyridine-5-carboxamide,
N-acetyl-N-(4-chlorophenyl)-4-acetoxy-6,7-dihydro-3,7-dimethyl-6-oxo-thieno[2,3-b]pyridine-5-carboxamide,
N-(4-chlorophenyl)-4-acetoxy-6,7-dihydro-3,7-dimethyl-6-oxo-thieno[2,3-b]pyridine-5-carboxamide,
N-(4-methoxyphenyl)-6,7-dihydro-4-hydroxy-3,7-dimethyl-6-oxo-thieno[2,3-b]pyridine-5-carboxamide,
N-acetyl-N-(4-methoxyphenyl)-4-acetoxy-6,7-dihydro-3,7-dimethyl-6-oxo-thieno[2,3-b]pyridine-5-carboxamide,
N-(4-methoxyphenyl)-4-acetoxy-6,7-dihydro-3,7-dimethyl-6-oxo-thieno[2,3-b]pyridine-5-carboxamide,
N-iso-butyryl-N-(4-methoxyphenyl)-4-iso-butyryloxy-6,7-dihydro-3,7-dimethyl-6-oxo-thieno[2,3-b]pyridine-5-carboxamide,
N-benzoyl-N-(4-methoxyphenyl)-4-benzoyloxy-6,7-dihydro-3,7-dimethyl-6-oxo-thieno[2,3-b]pyridine-5-carboxamide,
N-ethoxycarbonyl-N-(4-methoxyphenyl)-4-ethoxycarbonyloxy-6,7-dihydro-3,7-dimethyl-6-oxo-thieno[2,3-b]pyridine-5-carboxamide,
N-phenyl-3-ethyl-6,7-dihydro-4-hydroxy-7-methyl-6-oxo-thieno[2,3-b]pyridine-5-carboxamide,
N-acetyl-N-phenyl-4-acetoxy-3-ethyl-6,7-dihydro-7-methyl-6-oxo-thieno[2,3-b]pyridine-5-carboxamide,
N-phenyl-4-acetoxy-3-ethyl-6,7-dihydro-7-methyl-6-oxo-thieno[2,3-b]pyridine-5-carboxamide,
N-phenyl-6,7-dihydro-4-hydroxy-7-methyl-6-oxo-3-trifluoromethyl-thieno[2,3-b]pyridine-5-carboxamide,
N-acetyl-N-phenyl-4-acetoxy-6,7-dihydro-7-methyl-6-oxo-3-trifluoromethyl-thieno[2,3-b]pyridine-5-carboxamide, and
N-phenyl-4-acetoxy-6,7-dihydro-7-methyl-6-oxo-3-trifluoromethyl-thieno[2,3-b]pyridine-5-carboxamide.

In a second aspect the present invention relates to a new compound as described above for use as a medicament.

In a third aspect the present invention relates to the use of a new compound as described above for the manufacturing of a medicament for the treatment of cancer, autoimmune disorders, and other disorders with an immunological component.

In one preferred embodiment the cancer is chosen from the group comprising prostate cancer, intestinal cancer, and leukemia.

In another preferred embodiment the autoimmune disorder is chosen from the group comprising rheumatoid arthritis, multiple sclerosis, systemic lupus erythematosus, inflammatory bowel disease, diabetes type 1, and psoriasis.

In yet another preferred embodiment the disorder with an immunological component is chosen from the group comprising asthma, allergy, infection, bone loss, atherosclerosis, diabetes type 2, graft-versus-host, and transplant rejection.

In a fourth aspect the present invention relates to a pharmaceutical composition comprising a new compound as described above admixed with one or more pharmaceutically acceptable excipients or carriers.

In one preferred embodiment the excipients are chosen from the group comprising filling agents, lubricants, flavours, colourings, sweetenings, buffers, acidifying agents, diluents and preservatives.

In another preferred embodiment the pharmaceutical composition is administered orally, by oral inhalation, intramuscularly, intravenously, intraperitoneally or subcutaneously, via implants, rectally, intranasally, or transdermally; preferably orally.

In a fifth aspect the present invention relates to a method of treatment comprising administration of a pharmaceutically effective amount of a compound as described above or a pharmaceutical composition as described above to a subject suffering from cancer, autoimmune disorders, or other disorders with an immunological component.

In one embodiment the cancer to be treated is chosen from the group comprising prostate cancer, intestinal cancer, and leukemia.

In another embodiment the autoimmune disorder to be treated is chosen from the group comprising rheumatoid arthritis, multiple sclerosis, systemic lupus erythematosus, inflammatory bowel disease, diabetes type 1, and psoriasis.

In yet another embodiment the disorder with an immunological component to be treated is chosen from the group comprising asthma, allergy, infection, bone loss, atherosclerosis, diabetes type 2, graft-versus-host, and transplant rejection.

The compounds of the present invention may be given in doses about 0.01-1000 mg/day, preferably in doses about 0.1-10 mg/day. The compounds of the present invention may be administered orally, by oral inhalation, by injections, e.g. intramuscular, intravenous, intraperitoneal, or subcutaneous, via implants, rectally, intranasally, transdermally, or by any other route suitable to deliver a therapeutically active amount of the compound.

The pharmaceutical composition of the present invention comprises a pharmaceutically effective dose of at least one of the compounds according to the present invention, preferably in admixture with one or more pharmaceutically acceptable excipients, diluents or carriers. The amount administered will vary depending on various factors, e g age, sex, weight, which disorder or condition that is treated and the compound used. Both local and systemic administration is possible.

With "pharmaceutically acceptable" is meant that the excipients, diluents or carriers must be compatible with the other ingredients of the formulation, and not deleterious to the recipient thereof.

The pharmaceutical composition can be prepared according to any of the methods well known by a person skilled in the art of pharmacy. Such methods may include the step of bringing the novel compounds of the present invention in contact with liquid carriers, solid matrices, semi-solid carriers, finely diveded solid carriers or combinations thereof, and then, if necessary, introducing or shaping the product into the desired delivery system.

EMBODIMENTS OF THE PRESENT INVENTION

The present invention will now be described in more detail by the following examples, which are included in order to disclose some embodiments of the invention, but not in any way to limit the scope of the invention.

The novel 1,2-dihydro-4-hydroxy-1-methyl-2-oxo-quinoline-3-carboxanilide and 6,7-dihydro-4-hydroxy-7-methyl-6-oxo-thieno[2,3-b]pyridine-5-carboxanilide compounds according to the invention can be prepared by known methods described in the literature (refs 7b, 9a, 10). Thus, the carboxamides (c) can be formed by reacting acid derivatives (a), activated by e.g. DCC-coupling procedures, with anilines (b), or by reacting ester derivatives (d) or N,N-disubstituted (e.g. N-alkyl-N-aryl) carboxamides (e) with anilines at elevated temperatures (Scheme 1). The N,N-disubstituted carboxamides (e) can be formed analogously from the acid or ester derivatives and the carboxylic acids (a) can be prepared by acidic hydrolysis of the ester derivatives.

Scheme 1

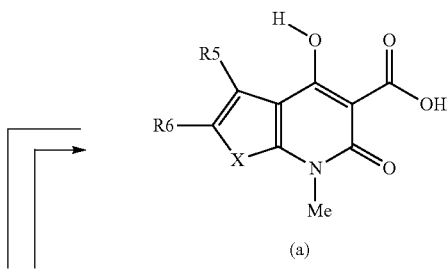

(a)

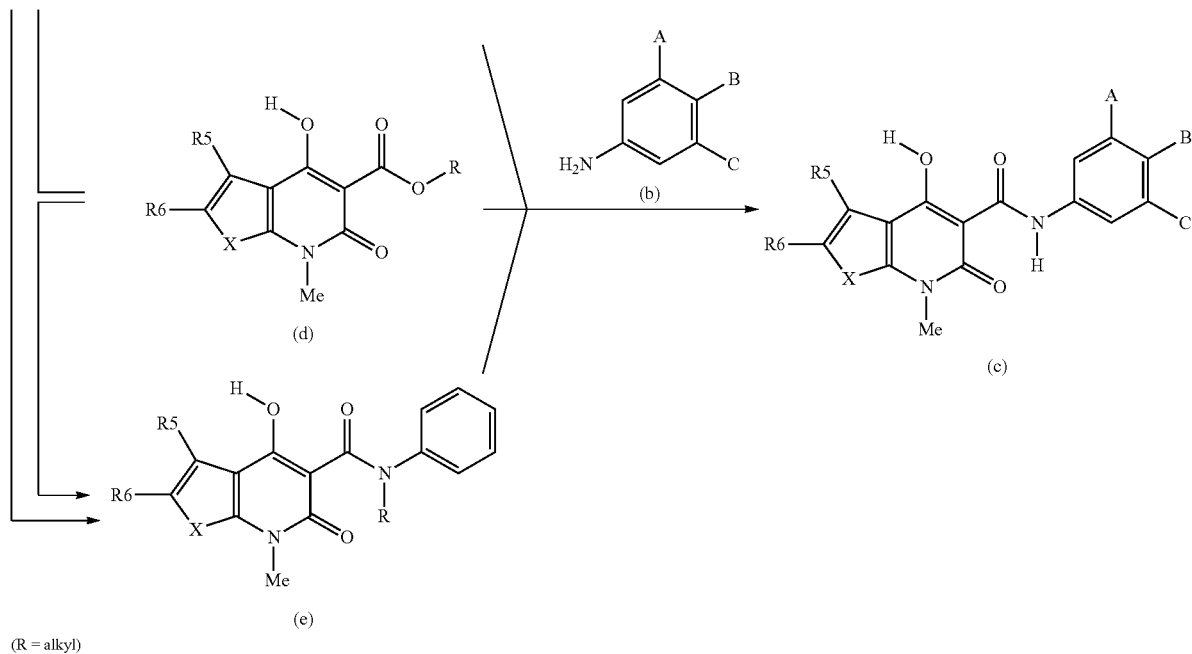

(R = alkyl)

Other methods for the preparation of carboxamides (c) are: to react malonic amides (f), as acid chlorides or as esters at elevated temperatures, with anthranilic ester derivatives (g), followed by deprotonation and ring closure to provide the carboxamides (Scheme 2); and, to react malonic amide esters (h) under basic conditions with N-methyl-isatoic anhydrides (i), which can be provided from reacting anthranilic acids (j) with phosgene (Scheme 3).

Scheme 2

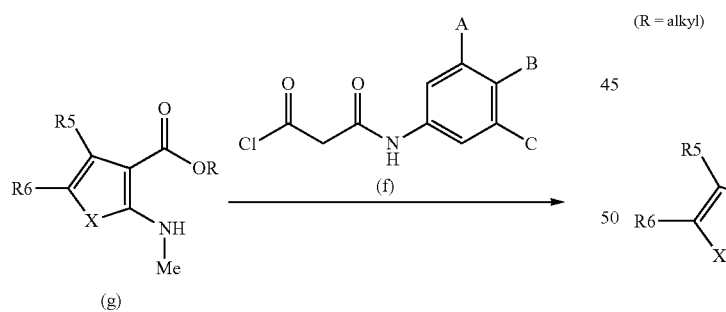

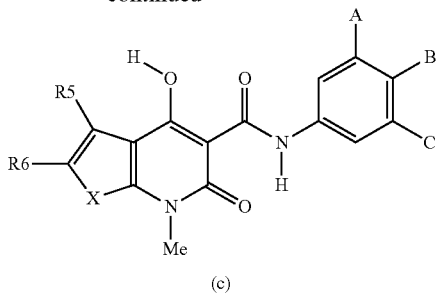

(R = alkyl)

Scheme 3

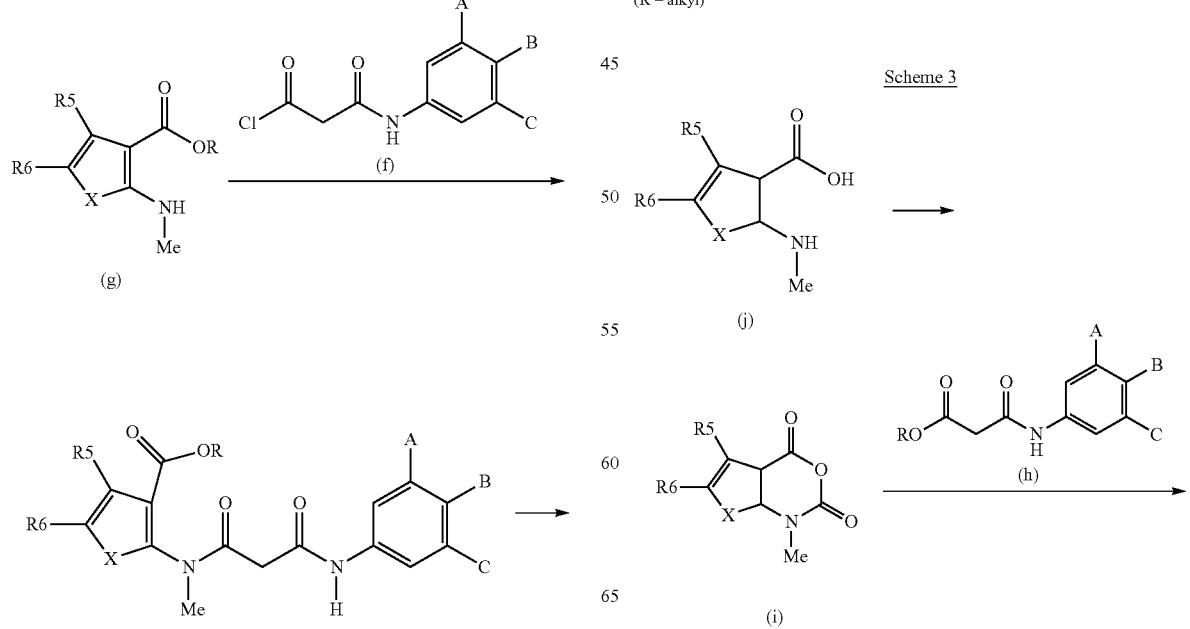

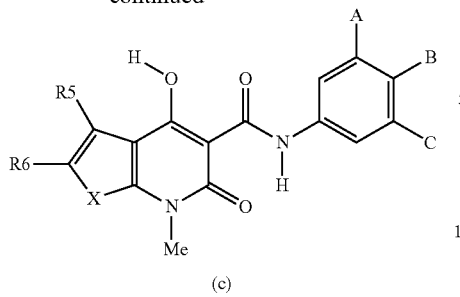

(c)

(R = alkyl)

The preparation of ester derivatives (d) can be performed in various ways starting from anthranilic esters (g), N-methyl-isatoic anhydrides (i) as well as from N-methyl-aniline derivatives (j) (Scheme 4). Reacting anthranilic esters (g) with alkylmalonic acidchloride or with dialkylmalonate at elevated temperatures provides amide intermediate (k), which can be reacted further under basic conditions to give the ester derivative (d). Similarly as described above, N-methyl-isatoic anhydrides react with dialkylmalonate under basic conditions to provide the ester derivative (d). Another method to prepare esters (d) is to react N-methyl-anilines (j) with trialkylmethanecarboxylate at high temperatures, typically at 180-230° C. in inert high-boiling solvents such as diphenylether.

Scheme 5

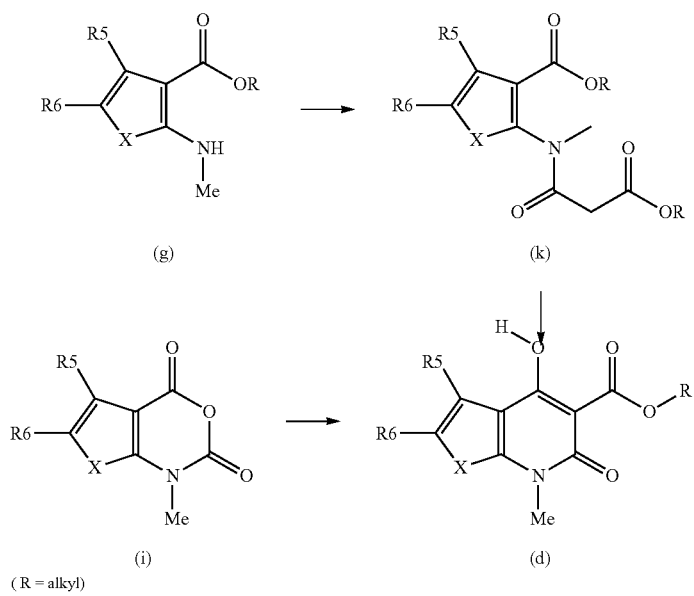

(R = alkyl)

In the preparations of esters (d) described above, the N-methyl group may be included in the starting materials as shown, or alternatively, it may be introduced in a last step, e.g. using MeI under basic conditions. The basic conditions referred to in the above reactions are typically a strong non-nucleophilic base, such as NaH, in an aprotic solvent, such as DMF, at temperatures 20-120° c.

Preparation of the 4-acyloxy (l) and the N-acyl-4-acyloxy (m) prodrug compounds can be performed using activated acid derivatives, such as acid chlorides or anhydrides and a non-nucleophilic base, such as trialkylamine, in non-nucleophilic solvents, such as $CH_2Cl_2$ (Scheme 5).

-continued

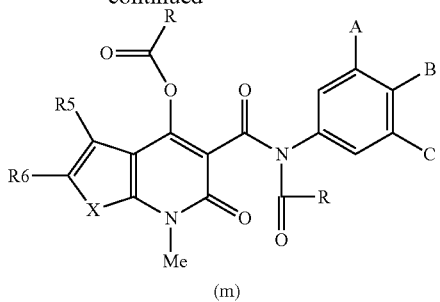

(m)

The mono- and the di-acylated products, (l) and (m), respectively, can be separated, e.g. by silica column chromatography. The N-acyl-4-acyloxy compounds (m) can selectively be prepared using an excess of the acylation reagents.

The mono-acylated 4-acyloxy compounds (l) can be prepared from the N-acyl-4-acyloxy compounds (m) by regioselective hydrolysis of the N-acyl group, using e.g. a solution of NaOH in MeOH, optionally with a co-solvent like THF.

An alternative method for the selective introduction of the prodrug moiety R4 is to use a protecting group at the amide nitrogen. Blocking the amide nitrogen will also disrupt intramolecular hydrogen bonding and give a twisted structure with enhanced reactivity at the 4-hydroxy group. The protecting group can be introduced during the preparation of the disubstituted amides (see Scheme 1), e.g. from the acid (a) or the ester (d) derivatives, using N-protected anilines as starting materials. The resulting protected amides (O) can be reacted at the 4-hydroxy group to give compounds (p), followed by deprotection providing the 4-hydroxy derivatized prodrug compounds (q) (Scheme 6).

One such protecting group is the 2,4-dimethoxybenzyl, which can be cleaved under acidic or oxidative conditions, e.g. by the use of cerium(IV)ammoniumnitrate in aqueous solvents. This protecting group can be introduced by preparation of the N-(2,4-dimethoxybenzyl)-aniline derivative (r), e.g. by reductive amination using NaBH$_4$ in MeOH, followed by reaction with an acid (a) or an ester (d) derivative providing the N-(2,4-dimethoxybenzyl) protected compound (s) (Scheme 7).

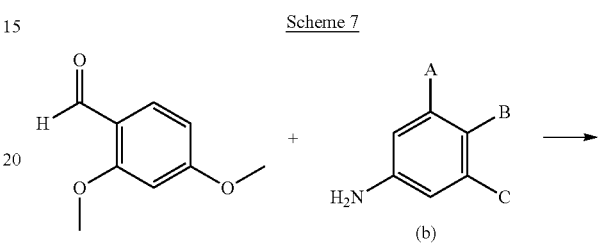

Scheme 7

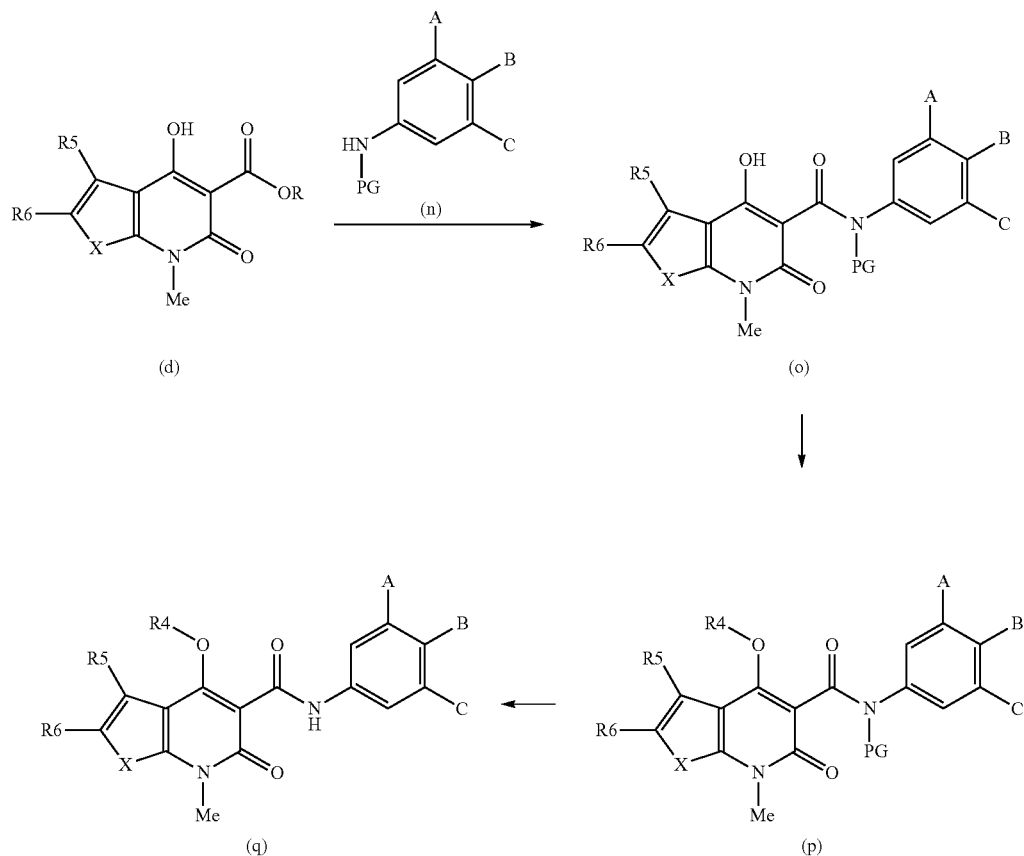

Scheme 6

(R = hydrogen or alkyl)

-continued

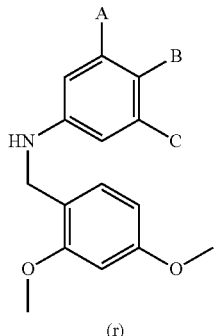 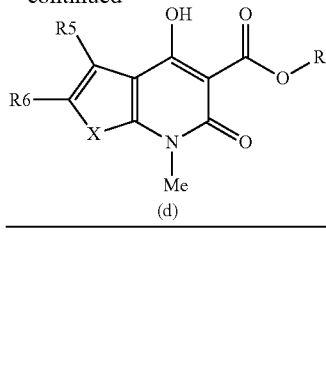

(r) (d) →

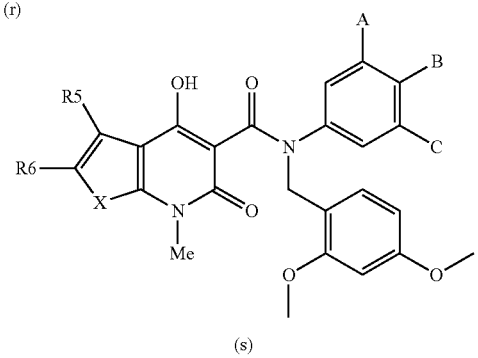

(s)

In the preparative examples column chromatography separations were performed using Merck SiO₂ 60 (0.040-0.063 mm) silica gel. NMR spectra were recorded on Varian Mercury (400 MHz) or on Bruker UltraShield (300 MHz) machines with CDCl₃ as solvent if not otherwise stated.

The following starting materials were prepared as described in the literature (refs 7b, 10):

Ethyl 1,2-dihydro-4-hydroxy-1-methyl-2-oxo-quinoline-3-carboxylate

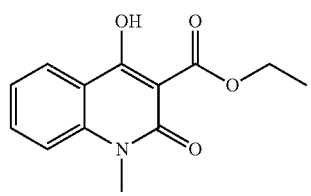 [SMILES: CCOC(=O)c1c(O)c2ccccc2n(C)c1=O]

$^1$H NMR: 1.48 (t, 3H), 3.65 (s, 3H), 4.50 (q, 2H), 7.26 (t, 1H), 7.31 (d, 1H), 7.68 (ddd, 1H), 8.18 (dd, 1H), 14.21 (s, 1H).

Ethyl 6-ethyl-1,2-dihydro-4-hydroxy-1-methyl-2-oxo-quinoline-3-carboxylate

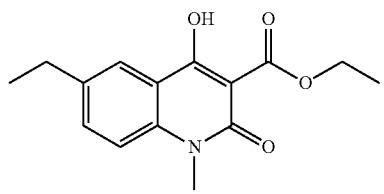 [SMILES: CCOC(=O)c1c(O)c2cc(CC)ccc2n(C)c1=O]

$^1$H NMR: 1.27 (t, 3H), 1.47 (t, 3H), 2.72 (q, 2H), 3.63 (s, 3H), 4.49 (q, 2H), 7.22 (d, 1H), 7.52 (dd, 1H), 7.97 (d, 1H), 14.20 (s, 1H).

Ethyl 6-chloro-1,2-dihydro-4-hydroxy-1-methyl-2-oxo-quinoline-3-carboxylate

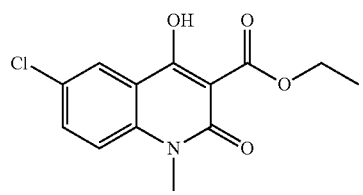 [SMILES: CCOC(=O)c1c(O)c2cc(Cl)ccc2n(C)c1=O]

$^1$H NMR: 1.48 (t, 3H), 3.64 (s, 3H), 4.51 (q, 2H), 7.26 (d, 1H), 7.62 (dd, 1H), 8.15 (d, 1H), 14.22 (s, 1H).

Ethyl 1,2-dihydro-4-hydroxy-6-methoxy-1-methyl-2-oxo-quinoline-3-carboxylate

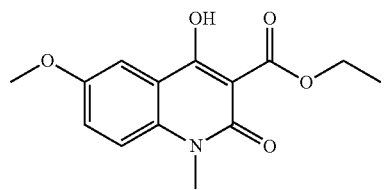 [SMILES: CCOC(=O)c1c(O)c2cc(OC)ccc2n(C)c1=O]

$^1$H NMR: 1.49 (t, 3H), 3.65 (s, 3H), 3.90 (s, 3H), 4.51 (q, 2H), 7.26 (d, 1H), 7.31 (dd, 1H), 7.58 (d, 1H), 14.24 (s, 1H).

Ethyl 6,7-dihydro-4-hydroxy-3,7-dimethyl-6-oxo-thieno[2,3-b]pyridine-5-carboxylate

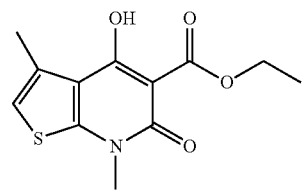 [SMILES: CCOC(=O)c1c(O)c2c(C)csc2n(C)c1=O]

$^1$H NMR: 1.45 (t, 3H), 2.49 (d, 1H), 3.55 (s, 3H), 4.45 (q, 2H), 6.46 (q, 1H), 14.23 (s, 1H).

N-methyl-N-phenyl-1,2-dihydro-4-hydroxy-1-methyl-2-oxo-quinoline-3-carboxamide

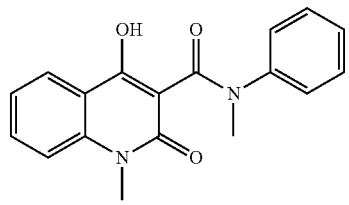 [SMILES: CN(C(=O)c1c(O)c2ccccc2n(C)c1=O)c1ccccc1]

$^1$H NMR: 3.00 (bs, 3H), 3.50 (s, 3H), 7.15-7.30 (m, 7H), 7.60 (ddd, 1H), 8.14 (dd, 1H), 12.48 (s, 1H).

N-ethyl-N-phenyl-5-ethyl-1,2-dihydro-4-hydroxy-1-methyl-2-oxo-quinoline-3-carboxamide

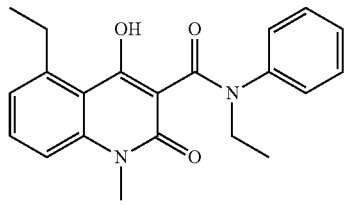 [SMILES: CCc1cccc2c1c(O)c(C(=O)N(CC)c1ccccc1)c(=O)n2C]

¹H NMR: 1.22 (t, 3H), 1.30 (t, 3H), 3.22-3.29 (m, 5H), 4.00 (q, 2H), 7.03 (t, 2H), 7.11-7.25 (m, 5H), 7.44 (dd, 1H), 13.16 (bs, 1H).

N-ethyl-N-phenyl-5-chloro-1,2-dihydro-4-hydroxy-1-methyl-2-oxo-quinoline-3-carboxamide

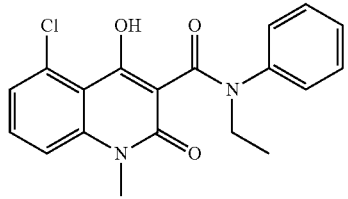 [SMILES: CCN(C(=O)c1c(O)c2c(Cl)cccc2n(C)c1=O)c1ccccc1]

¹H NMR: 1.22 (t, 3H), 3.30 (s, 3H), 3.99 (q, 2H), 7.10-7.27 (m, 7H), 7.42 (dd, 1H), 12.63 (bs, 1H).

N-ethyl-N-phenyl-1,2-dihydro-4-hydroxy-1-methyl-5-methoxy-2-oxo-quinoline-3-carboxamide

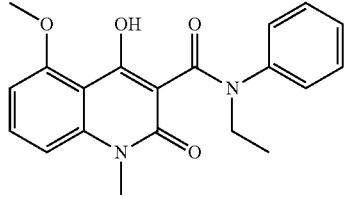 [SMILES: CCN(C(=O)c1c(O)c2c(OC)cccc2n(C)c1=O)c1ccccc1]

¹H NMR: 1.24 (t, 3H), 3.49 (s, 3H), 3.95 (q, 2H), 4.01 (s, 3H), 6.63 (d, 1H), 6.87 (d, 1H), 7.11-7.23 (m, 3H), 7.34-7.43 (m, 3H), 9.78 (s, 1H).

Example 1

N-(4-fluorophenyl)-1,2-dihydro-4-hydroxy-1-methyl-2-oxo-quinoline-3-carboxamide

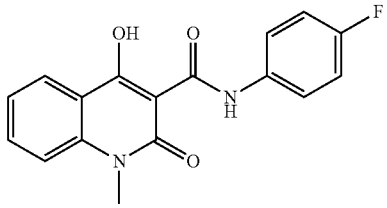 [SMILES: Cn1c(=O)c(C(=O)Nc2ccc(F)cc2)c(O)c2ccccc21]

A solution of N-methyl-N-phenyl-1,2-dihydro-4-hydroxy-1-methyl-2-oxo-quinoline-3-carboxamide (15 mg, 0.050 mmol) and 4-fluoro-aniline (0.100 mmol) in toluene (0.5 mL) was stirred at 100° C. for 1 h. Heptane (1.5 mL) was added and the solution was allowed to cool to room temperature. The crystallized product was separated from the solution and washed with heptane to give the title compound (12 mg, 79%).

¹H NMR: 3.74 (s, 3H), 7.07 (t, 2H), 7.34 (t, 1H), 7.40 (d, 1H), 7.65 (m, 2H), 7.73 (ddd, 1H), 8.26 (dd, 1H), 12.52 (s, 1H), 16.62 (s, 1H).

The following compounds were prepared by the same method in 70-95% yields:

Example 2

N-(4-trifluoromethylphenyl)-1,2-dihydro-4-hydroxy-1-methyl-2-oxo-quinoline-3-carboxamide

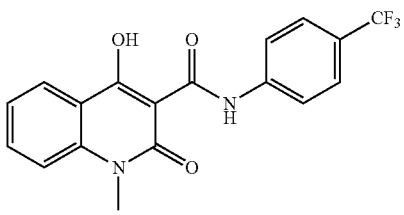 [SMILES: Cn1c(=O)c(C(=O)Nc2ccc(C(F)(F)F)cc2)c(O)c2ccccc21]

¹H NMR: 3.74 (s, 3H), 7.33 (t, 1H), 7.41 (d, 1H), 7.62 (d, 2H), 7.73 (ddd, 1H), 7.82 (d, 2H), 8.26 (dd, 1H), 12.81 (s, 1H), 16.35 (s, 1H).

Example 3

N-(4-ethylphenyl)-1,2-dihydro-4-hydroxy-1-methyl-2-oxo-quinoline-3-carboxamide

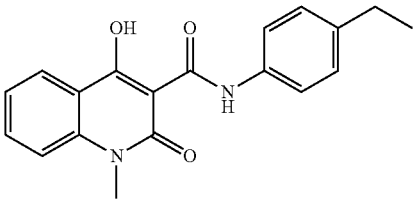 [SMILES: CCc1ccc(NC(=O)c2c(O)c3ccccc3n(C)c2=O)cc1]

¹H NMR: 1.24 (t, 3H), 2.65 (q, 2H), 3.74 (s, 3H), 7.22 (d, 2H), 7.34 (t, 1H), 7.40 (d, 1H), 7.60 (d, 2H), 7.72 (ddd, 1H), 8.26 (dd, 1H), 12.44 (s, 1H), 16.87 (s, 1H).

Example 4

N-(4-tert-butylphenyl)-1,2-dihydro-4-hydroxy-1-methyl-2-oxo-quinoline-3-carboxamide

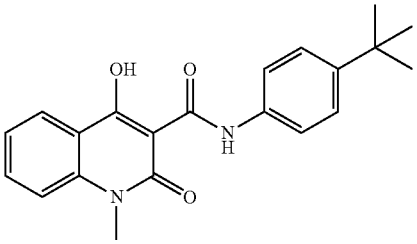 [SMILES: Cn1c(=O)c(C(=O)Nc2ccc(C(C)(C)C)cc2)c(O)c2ccccc21]

¹H NMR: 1.33 (s, 9H), 3.74 (s, 3H), 7.34 (t, 1H), 7.40 (2d, 3H), 7.61 (d, 2H), 7.72 (ddd, 1H), 8.26 (dd, 1H), 12.43 (s, 1H), 16.88 (s, 1H).

Example 5

N-(4-iodophenyl)-1,2-dihydro-4-hydroxy-1-methyl-2-oxo-quinoline-3-carboxamide

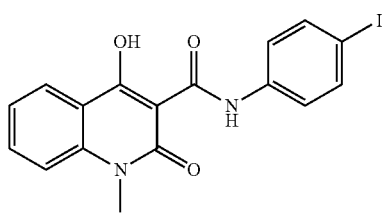 [SMILES: Cn1c(=O)c(C(=O)Nc2ccc(I)cc2)c(O)c2ccccc21]

$^1$H NMR: 3.73 (s, 3H), 7.34 (t, 1H), 7.40 (d, 1H), 7.48 (d, 2H), 7.67 (d, 2H), 7.73 (ddd, 1H), 8.25 (dd, 1H), 12.60 (s, 1H), 16.49 (s, 1H).

Example 6

N-(4-methylthiophenyl)-1,2-dihydro-4-hydroxy-1-methyl-2-oxo-quinoline-3-carboxamide

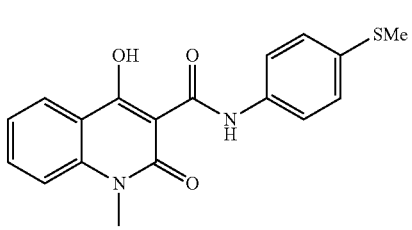 [SMILES: CSc1ccc(NC(=O)c2c(O)c3ccccc3n(C)c2=O)cc1]

$^1$H NMR: 2.49 (s, 3H), 3.73 (s, 3H), 7.28 (d, 2H), 7.33 (t, 1H), 7.39 (d, 1H), 7.63 (d, 2H), 7.71 (ddd, 1H), 8.24 (dd, 1H), 12.51 (s, 1H), 16.69 (s, 1H).

Example 7

N-(3-methylphenyl)-1,2-dihydro-4-hydroxy-1-methyl-2-oxo-quinoline-3-carboxamide

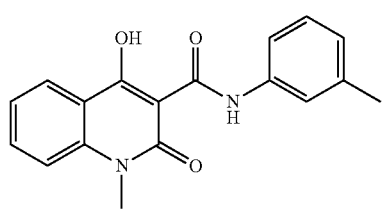 [SMILES: Cc1cccc(NC(=O)c2c(O)c3ccccc3n(C)c2=O)c1]

$^1$H NMR: 2.38 (s, 3H), 3.74 (s, 3H), 6.99 (d, 1H), 7.27 (t, 1H), 7.34 (t, 1H), 7.40 (d, 1H), 7.51 (m, 2H), 7.72 (ddd, 1H), 8.26 (dd, 1H), 12.49 (s, 1H), 16.79 (s, 1H).

Example 8

N-(3,5-di(trifluoromethyl)phenyl)-1,2-dihydro-4-hydroxy-1-methyl-2-oxo-quinoline-3-carboxamide

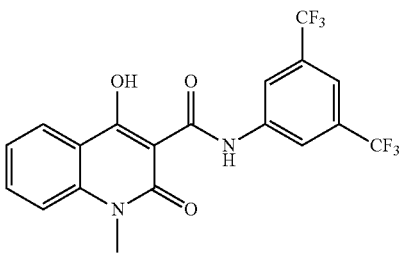 [SMILES: Cn1c(=O)c(C(=O)Nc2cc(C(F)(F)F)cc(C(F)(F)F)c2)c(O)c2ccccc21]

$^1$H NMR: 3.76 (s, 3H), 7.38 (t, 1H), 7.44 (d, 1H), 7.65 (bs, 1H), 7.77 (ddd, 1H), 8.22 (bs, 2H), 8.29 (dd, 1H), 13.10 (s, 1H), 16.00 (s, 1H).

Example 9

N-(3,4-difluorophenyl)-1,2-dihydro-4-hydroxy-1-methyl-2-oxo-quinoline-3-carboxamide

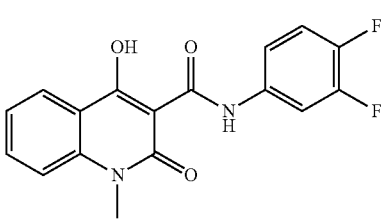 [SMILES: Cn1c(=O)c(C(=O)Nc2ccc(F)c(F)c2)c(O)c2ccccc21]

$^1$H NMR: 3.74 (s, 3H), 7.15 (m, 1H), 7.25-7.30 (m, 1H), 7.35 (t, 1H), 7.41 (d, 1H), 7.74 (ddd, 1H), 7.79 (m, 1H), 8.26 (dd, 1H), 12.65 (s, 1H), 16.36 (s, 1H).

The same method, with stirring for 2 h, and using N-ethyl-N-phenyl-1,2-dihydro-4-hydroxy-1-methyl-5-methoxy-2-oxo-quinoline-3-carboxamide, N-ethyl-N-phenyl-5-ethyl-1,2-dihydro-4-hydroxy-1-methyl-2-oxo-quinoline-3-carboxamide, or N-ethyl-N-phenyl-5-chloro-1,2-dihydro-4-hydroxy-1-methyl-2-oxo-quinoline-3-carboxamide, as starting material, was used to prepare the following compounds:

Example 10

N-phenyl-1,2-dihydro-4-hydroxy-5-methoxy-1-methyl-2-oxo-quinoline-3-carboxamide

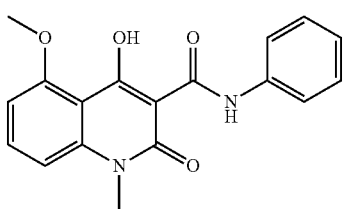 [SMILES: COc1cccc2c1c(O)c(C(=O)Nc1ccccc1)c(=O)n2C]

$^1$H NMR: 3.71 (s, 3H), 4.01 (s, 3H), 6.79 (d, 1H), 6.99 (d, 1H), 7.15 (t, 1H), 7.37 (dd, 1H), 7.60 (t, 1H), 7.68 (d, 1H), 12.69 (s, 1H), 17.68 (s, 1H).

Example 11

N-(4-trifluoromethylphenyl)-1,2-dihydro-4-hydroxy-5-methoxy-1-methyl-2-oxo-quinoline-3-carboxamide

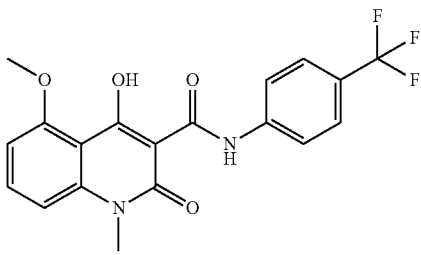 [SMILES: COc1cccc2c1c(O)c(C(=O)Nc1ccc(C(F)(F)F)cc1)c(=O)n2C]

$^1$H NMR: 3.72 (s, 3H), 4.02 (s, 3H), 6.81 (d, 1H), 7.00 (d, 1H), 7.59-7.65 (m, 3H), 7.81 (d, 2H), 12.99 (s, 1H).

Example 12

N-(4-fluorophenyl)-1,2-dihydro-4-hydroxy-5-methoxy-1-methyl-2-oxo-quinoline-3-carboxamide

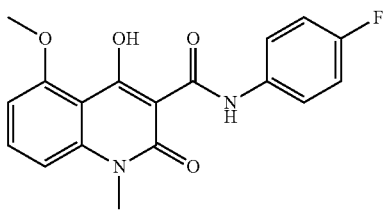 [SMILES: COc1cccc2c1c(O)c(C(=O)Nc1ccc(F)cc1)c(=O)n2C]

$^1$H NMR: 3.71 (s, 3H), 4.02 (s, 3H), 6.80 (d, 1H), 7.00 (d, 1H), 7.06 (t, 2H), 7.59-7.68 (m, 3H), 12.69 (s, 1H), 17.55 (s, 1H).

Example 13

N-phenyl-5-ethyl-1,2-dihydro-4-hydroxy-1-methyl-2-oxo-quinoline-3-carboxamide

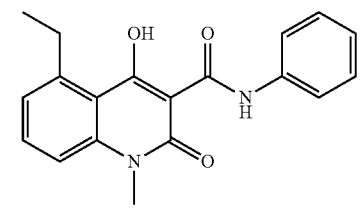 [SMILES: CCc1cccc2c1c(O)c(C(=O)Nc1ccccc1)c(=O)n2C]

The product was crystallized from abs. EtOH.

$^1$H NMR: 1.31 (t, 3H), 3.32 (q, 2H), 3.73 (s, 3H), 7.13 (d, 1H), 7.16 (tt, 1H), 7.28 (dd, 1H), 7.38 (t, 2H), 7.58 (dd, 1H), 7.69 (m, 2H), 12.78 (bs, 1H), 17.55 (s, 1H).

Example 14

N-(4-chlorophenyl)-5-ethyl-1,2-dihydro-4-hydroxy-1-methyl-2-oxo-quinoline-3-carboxamide

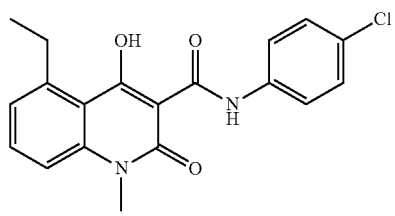 [SMILES: CCc1cccc2c1c(O)c(C(=O)Nc1ccc(Cl)cc1)c(=O)n2C]

$^1$H NMR: 1.31 (t, 3H), 3.31 (q, 2H), 3.73 (s, 3H), 7.14 (d, 1H), 7.29 (d, 1H), 7.34 (d, 2H), 7.59 (dd, 1H), 7.65 (d, 2H), 12.87 (bs, 1H), 17.43 (s, 1H).

N-phenyl-5-chloro-1,2-dihydro-4-hydroxy-1-methyl-2-oxo-quinoline-3-carboxamide

Not according to invention. Prepared as precursor for acylation reactions.

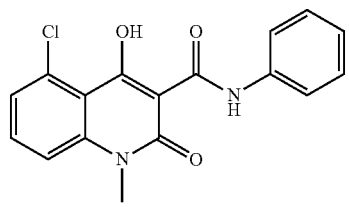 [SMILES: Cn1c(=O)c(C(=O)Nc2ccccc2)c(O)c2c(Cl)cccc21]

$^1$H NMR: 3.73 (s, 3H), 7.18 (t, 1H), 7.31-7.42 (m, 4H), 7.54 (dd, 1H), 7.68 (d, 2H), 12.58 (s, 1H), 17.91 (s, 1H).

Example 15

N-(4-methylphenyl)-5-chloro-1,2-dihydro-4-hydroxy-1-methyl-2-oxo-quinoline-3-carboxamide

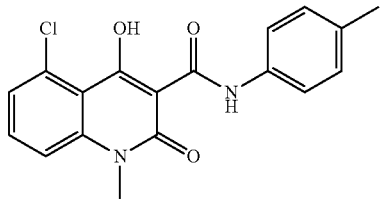 [SMILES: Cc1ccc(NC(=O)c2c(O)c3c(Cl)cccc3n(C)c2=O)cc1]

$^1$H NMR: 2.36 (s, 3H), 3.71 (s, 3H), 7.19 (d, 2H), 7.34 (m, 2H), 7.52-7.59 (m, 3H), 12.52 (s, 1H), 18.00 (s, 1H).

Example 16

N-(4-chlorophenyl)-5-chloro-1,2-dihydro-4-hydroxy-1-methyl-2-oxo-quinoline-3-carboxamide

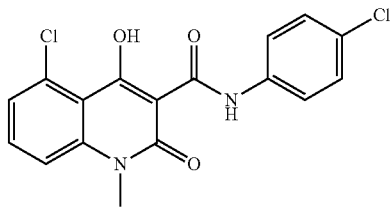 [SMILES: Cn1c(=O)c(C(=O)Nc2ccc(Cl)cc2)c(O)c2c(Cl)cccc21]

¹H NMR: 3.74 (s, 3H), 7.31-7.39 (m, 4H), 7.56 (t, 1H), 7.64 (d, 2H), 12.70 (s, 1H), 17.68 (s, 1H).

Example 17

N-(4-methoxyphenyl)-5-chloro-1,2-dihydro-4-hydroxy-1-methyl-2-oxo-quinoline-3-carboxamide

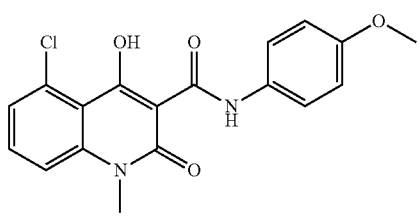 [SMILES: COc1ccc(NC(=O)c2c(O)c3c(Cl)cccc3n(C)c2=O)cc1]

¹H NMR: 3.74 (s, 3H), 3.83 (s, 3H), 6.93 (d, 2H), 7.32-7.38 (m, 2H), 7.51-7.62 (m, 3H), 12.48 (bs, 1H), 18.05 (s, 1H).

N-(4-methylphenyl)-1,2-dihydro-4-hydroxy-1-methyl-2-oxo-quinoline-3-carboxamide

Not according to invention. Prepared as precursor for acylation reactions.

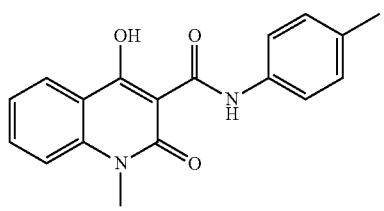 [SMILES: Cc1ccc(NC(=O)c2c(O)c3ccccc3n(C)c2=O)cc1]

A solution of ethyl 1,2-dihydro-4-hydroxy-1-methyl-2-oxo-quinoline-3-carboxylate (247 mg, 1.00 mmol) and 4-Me-aniline (133 mg, 1.25 mmol) in heptane (20 mL) was stirred at 100° C. for 8 h in a sealed vial, with occasional opening letting formed EtOH to evaporate.

After cooling the product crystallized from the solution and was collected by filtration. Recrystallization from heptane gave the title compound (229 mg, 74%).

¹H NMR: 2.35 (s, 3H), 3.74 (s, 3H), 7.19 (d, 2H), 7.34 (t, 1H), 7.40 (d, 1H), 7.57 (d, 2H), 7.72 (ddd, 1H), 8.26 (dd, 1H), 12.43 (s, 1H), 16.86 (s, 1H).

The following compounds were prepared by essentially the same method in 71-99% yields starting from the corresponding Et-ester starting materials, in scales ranging from 0.10 to 40 mmol.

Recrystallizations if needed were performed from heptane or from heptane-EtOAc mixtures:

N-phenyl-1,2-dihydro-4-hydroxy-1-methyl-2-oxo-quinoline-3-carboxamide

Not according to invention. Prepared as precursor for acylation reactions.

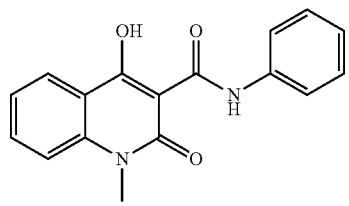 [SMILES: Cn1c(=O)c(C(=O)Nc2ccccc2)c(O)c2ccccc21]

¹H NMR: 3.74 (s, 3H), 7.17 (t, 1H), 7.34 (t, 1H), 7.39 (t, 2H), 7.40 (d, 1H), 7.70 (d, 2H), 7.72 (ddd, 1H), 8.26 (dd, 1H), 12.53 (s, 1H), 16.75 (s, 1H).

N-(4-methoxyphenyl)-1,2-dihydro-4-hydroxy-1-methyl-2-oxo-quinoline-3-carboxamide Not according to invention. Prepared as precursor for acylation reactions.

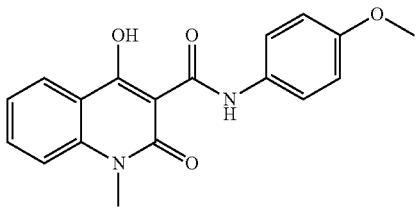 [SMILES: COc1ccc(NC(=O)c2c(O)c3ccccc3n(C)c2=O)cc1]

¹H NMR: 3.74 (s, 3H), 3.82 (s, 3H), 6.92 (d, 2H), 7.34 (t, 1H), 7.40 (d, 1H), 7.60 (d, 2H), 7.72 (ddd, 1H), 8.26 (dd, 1H), 12.37 (s, 1H), 16.88 (s, 1H)

Example 18

Same Compound as Example 1

N-(4-fluorophenyl)-1,2-dihydro-4-hydroxy-1-methyl-2-oxo-quinoline-3-carboxamide

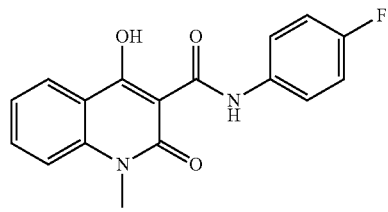

¹H NMR: 3.74 (s, 3H), 7.07 (t, 2H), 7.34 (t, 1H), 7.40 (d, 1H), 7.65 (m, 2H), 7.73 (ddd, 1H), 8.26 (dd, 1H), 12.52 (s, 1H), 16.62 (s, 1H).

N-(4-chlorophenyl)-1,2-dihydro-4-hydroxy-1-methyl-2-oxo-quinoline-3-carboxamide

Not according to invention. Prepared as precursor for acylation reactions.

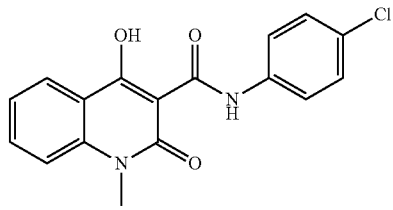 [SMILES: Cn1c(=O)c(C(=O)Nc2ccc(Cl)cc2)c(O)c2ccccc21]

$^1$H NMR: 3.73 (s, 3H), 7.33 (d, 2H), 7.34 (t, 1H), 7.40 (d, 1H), 7.65 (d, 2H), 7.72 (ddd, 1H), 8.25 (dd, 1H), 12.60 (s, 1H), 16.52 (s, 1H).

Example 19

Same Compound as Example 2

N-(4-trifluoromethylphenyl)-1,2-dihydro-4-hydroxy-1-methyl-2-oxo-quinoline-3-carboxamide

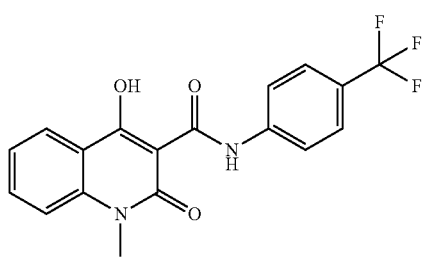 [SMILES: Cn1c(=O)c(C(=O)Nc2ccc(C(F)(F)F)cc2)c(O)c2ccccc21]

$^1$H NMR: 3.74 (s, 3H), 7.33 (t, 1H), 7.41 (d, 1H), 7.62 (d, 2H), 7.73 (ddd, 1H), 7.82 (dd, 2H), 8.26 (d, 1H), 12.81 (s, 1H), 16.35 (s, 1H).

Example 20

N-phenyl-5-ethyl-1,2-dihydro-4-hydroxy-1-methyl-2-oxo-quinoline-3-carboxamide

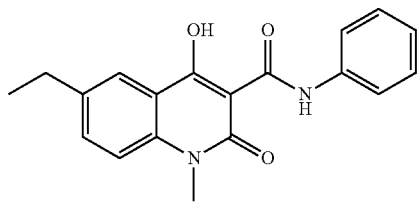 [SMILES: CCc1ccc2c(c1)c(O)c(C(=O)Nc1ccccc1)c(=O)n2C]

$^1$H NMR: 1.30 (t, 3H), 2.77 (q, 2H), 3.72 (s, 3H), 7.17 (t, 1H), 7.33 (d, 1H), 7.39 (t, 2H), 7.57 (dd, 1H), 7.70 (d, 2H), 8.07 (d, 1H), 12.58 (s, 1H), 16.74 (s, 1H).

Example 21

N-(4-ethylphenyl)-5-ethyl-1,2-dihydro-4-hydroxy-1-methyl-2-oxo-quinoline-3-carboxamide

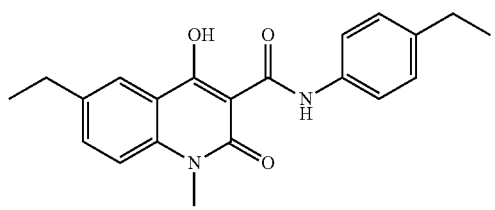 [SMILES: CCc1ccc(NC(=O)c2c(O)c3cc(CC)ccc3n(C)c2=O)cc1]

$^1$H NMR: 1.24 (t, 3H), 1.30 (t, 3H), 2.64 (q, 2H), 2.77 (q, 2H), 3.72 (s, 3H), 7.22 (d, 2H), 7.33 (d, 1H), 7.57 (dd, 1H), 7.60 (d, 2H), 8.07 (d, 1H), 12.49 (s, 1H), 16.85 (s, 1H).

Example 22

N-phenyl-6,7-dihydro-4-hydroxy-3,7-dimethyl-6-oxo-thieno[2,3-b]pyridine-5-carboxamide

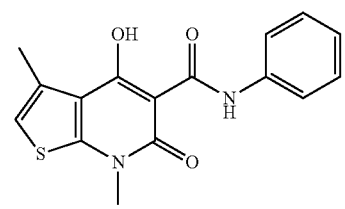 [SMILES: Cc1csc2c1c(O)c(C(=O)Nc1ccccc1)c(=O)n2C]

$^1$H NMR: 2.55 (s, 3H), 3.65 (s, 3H), 6.54 (s, 1H), 7.15 (t, 1H), 7.38 (t, 2H), 7.67 (d, 2H), 12.39 (s, 1H), 16.65 (s, 1H).

Example 23

N-(4-methoxyphenyl)-6,7-dihydro-4-hydroxy-3,7-dimethyl-6-oxo-thieno[2,3-b]pyridine-5-carboxamide

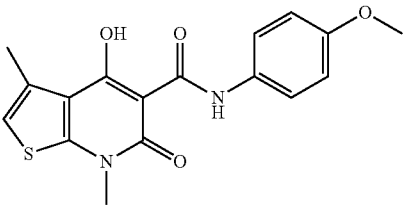 [SMILES: COc1ccc(NC(=O)c2c(O)c3c(C)csc3n(C)c2=O)cc1]

$^1$H NMR: 2.55 (s, 3H), 3.65 (s, 3H), 3.82 (s, 3H), 6.54 (s, 1H), 6.92 (d, 2H), 7.58 (d, 2H), 12.24 (s, 1H), 16.74 (s, 1H).

Example 24

N-(4-fluorophenyl)-6,7-dihydro-4-hydroxy-3,7-dimethyl-6-oxo-thieno[2,3-b]pyridine-5-carboxamide

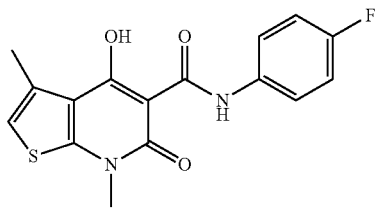 [SMILES: Cc1csc2c1c(O)c(C(=O)Nc1ccc(F)cc1)c(=O)n2C]

$^1$H NMR: 2.55 (s, 3H), 3.65 (s, 3H), 6.54 (s, 1H), 7.07 (dd, 2H), 7.63 (m, 2H), 12.39 (s, 1H), 16.52 (s, 1H).

N-phenyl-1,2-dihydro-4-hydroxy-6-methoxy-1-methyl-2-oxo-quinoline-3-carboxamide

Not according to invention. Prepared as precursor for acylation reactions. Purified by silica column chromatography (CHCl$_3$) and recrystallized from heptane-CHCl$_3$.

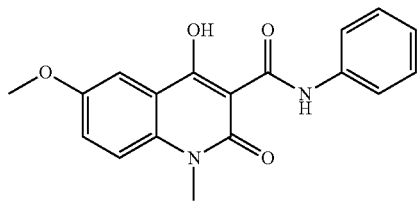

$^1$H NMR: 3.73 (s, 3H), 3.93 (s, 3H), 7.18 (t, 1H), 7.34 (bs, 2H), 7.39 (t, 2H), 7.64 (bs, 1H), 7.70 (d, 2H), 12.65 (s, 1H), 16.78 (s, 1H).

Example 25

N-(4-fluorophenyl)-1,2-dihydro-4-hydroxy-6-methoxy-1-methyl-2-oxo-quinoline-3-carboxamide Purified by silica column chromatography (CHCl$_3$) and recrystallized from heptane-CHCl$_3$.

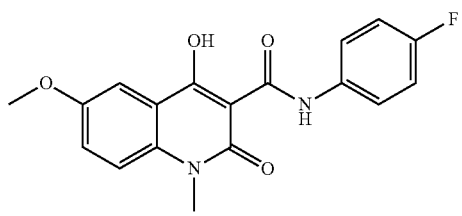 [SMILES: COc1ccc2c(c1)c(O)c(C(=O)Nc1ccc(F)cc1)c(=O)n2C]

$^1$H NMR: 3.73 (s, 3H), 3.92 (s, 3H), 7.08 (t, 2H), 7.34 (d, 2H), 7.61-7.70 (m, 3H), 12.64 (s, 1H), 16.65 (s, 1H).

Example 26

N-(4-chlorophenyl)-1,2-dihydro-4-hydroxy-6-methoxy-1-methyl-2-oxo-quinoline-3-carboxamide Purified by silica column chromatography (CHCl$_3$) and recrystallized from heptane-CHCl$_3$.

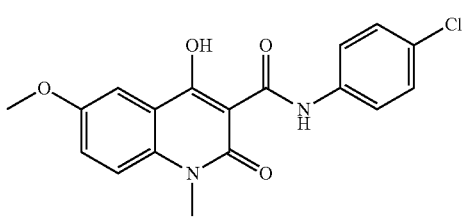 [SMILES: COc1ccc2c(c1)c(O)c(C(=O)Nc1ccc(Cl)cc1)c(=O)n2C]

$^1$H NMR: 3.72 (s, 3H), 3.92 (s, 3H), 7.31-7.37 (m, 4H), 7.61-7.69 (m, 3H), 12.73 (s, 1H), 16.65 (s, 1H).

N-phenyl-6-chloro-1,2-dihydro-4-hydroxy-1-methyl-2-oxo-quinoline-3-carboxamide

Not according to invention. Prepared as precursor for acylation reactions. Purified by silica column chromatography (CHCl$_3$) and recrystallized from heptane-CHCl$_3$.

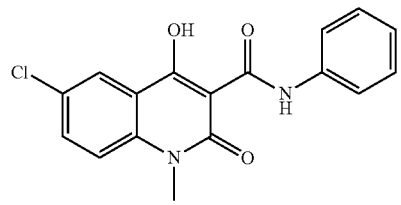 [SMILES: Cn1c(=O)c(C(=O)Nc2ccccc2)c(O)c2cc(Cl)ccc21]

$^1$H NMR: 3.73 (s, 3H), 7.18 (t, 1H), 7.34 (d, 1H), 7.39 (t, 2H), 7.65 (dd, 1H), 7.69 (d, 2H), 8.22 (d, 1H), 12.44 (s, 1H), 16.85 (s, 1H).

Example 27

N-(4-fluorophenyl)-6-chloro-1,2-dihydro-4-hydroxy-1-methyl-2-oxo-quinoline-3-carboxamide Purified by silica column chromatography (CHCl$_3$) and recrystallized from heptane-CHCl$_3$.

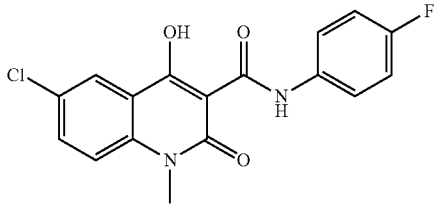 [SMILES: Cn1c(=O)c(C(=O)Nc2ccc(F)cc2)c(O)c2cc(Cl)ccc21]

$^1$H NMR: 3.72 (s, 3H), 7.08 (t, 2H), 7.34 (d, 1H), 7.60-7.68 (m, 3H), 8.20 (d, 1H), 12.42 (s, 1H), 16.70 (s, 1H).

Example 28

N-(4-chlorophenyl)-6-chloro-1,2-dihydro-4-hydroxy-1-methyl-2-oxo-quinoline-3-carboxamide Purified by silica column chromatography (CHCl₃) and recrystallized from heptane-CHCl₃.

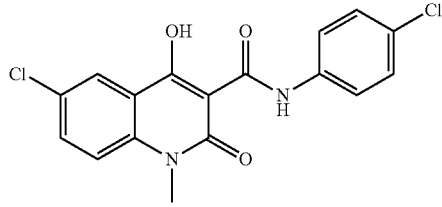 [SMILES: Cn1c(=O)c(C(=O)Nc2ccc(Cl)cc2)c(O)c2cc(Cl)ccc21]

¹H NMR: 3.72 (s, 3H), 7.32-7.38 (m, 3H), 7.62-7.69 (m, 3H), 8.23 (d, 1H), 12.52 (s, 1H), 16.62 (s, 1H).

Example 29

N-(4-methoxyphenyl)-6-chloro-1,2-dihydro-4-hydroxy-1-methyl-2-oxo-quinoline-3-carboxamide Purified by silica column chromatography (CHCl₃) and recrystallized from heptane-CHCl₃.

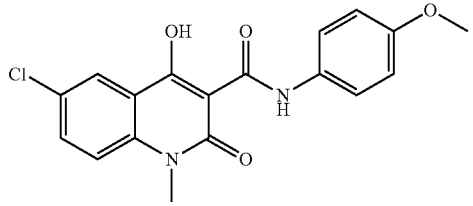 [SMILES: COc1ccc(NC(=O)c2c(O)c3cc(Cl)ccc3n(C)c2=O)cc1]

¹H NMR: 3.70 (s, 3H), 3.82 (s, 3H), 6.92 (d, 2H), 7.32 (d, 1H), 7.58 (d, 2H), 7.62 (dd, 1H), 8.19 (d, 1H), 12.27 (s, 1H), 16.96 (s, 1H).

Example 30

N-acetyl-N-phenyl-4-acetoxy-1,2-dihydro-1-methyl-2-oxo-quinoline-3-carboxamide

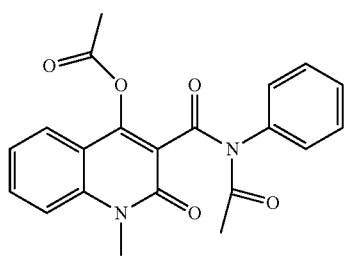 [SMILES: CC(=O)Oc1c(C(=O)N(C(C)=O)c2ccccc2)c(=O)n(C)c2ccccc12]

and

Example 31

N-phenyl-4-acetoxy-1,2-dihydro-1-methyl-2-oxo-quinoline-3-carboxamide

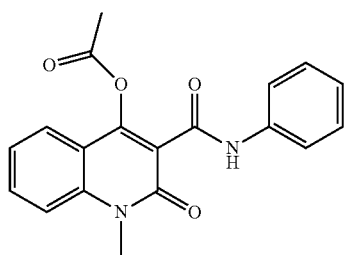 [SMILES: CC(=O)Oc1c(C(=O)Nc2ccccc2)c(=O)n(C)c2ccccc12]

A solution of acetylchloride (447 mg, 5.69 mmol) in CH₂Cl₂ (3.0 mL) was added to a solution of N-phenyl-1,2-dihydro-4-hydroxy-1-methyl-2-oxo-quinoline-3-carboxamide (864 mg, 2.94 mmol), EtNiPr₂ (1.31 g, 10.1 mmol) and DMAP (49 mg, 0.40 mmol) in CH₂Cl₂ (10 mL). The reaction mixture was stirred for 30 min, then additional EtNiPr₂ (1.31 g, 10.1 mmol) and acetylchloride (447 mg, 5.69 mmol) was added. The reaction mixture was stirred for another 60 min and concentrated at reduced pressure. The residue was purified by silica column chromatography (heptane:EtOAc 2:1, 1:1, 1:2) to give the title compounds.

For N-phenyl-4-acetoxy-1,2-dihydro-1-methyl-2-oxo-quinoline-3-carboxamide (129 mg, 13%):

¹H NMR: 2.57 (s, 3H), 3.82 (s, 3H), 7.12 (tt, 1H), 7.31-7.41 (m, 3H), 7.48 (d, 1H), 7.67-7.78 (m, 3H), 7.94 (dd, 1H), 11.85 (s, 1H).

For N-acetyl-N-phenyl-4-acetoxy-1,2-dihydro-1-methyl-2-oxo-quinoline-3-carboxamide (280 mg, 25%):

¹H NMR: 2.11 (s, 3H), 2.39 (s, 3H), 3.68 (s, 3H), 7.27 (t, 1H), 7.35-7.48 (m, 6H), 7.58-7.65 (m, 2H).

Example 32

Same Compound as Example 30

N-acetyl-N-phenyl-4-acetoxy-1,2-dihydro-1-methyl-2-oxo-quinoline-3-carboxamide

A solution of AcCl (6.28 g, 80.0 mmol) in CH₂Cl₂ (10 mL) was added in portions during 1 h to a solution of N-phenyl-1,2-dihydro-4-hydroxy-1,5-dimethyl-2-oxo-quinoline-3-carboxamide (6.40 g, 22.0 mmol) and EtNiPr₂ (12.92 g, 100.0 mmol) in CH₂Cl₂ (100 mL). The reaction mixture was stirred for another 30 min and was then partitioned between EtOAc and 1 M HCl (aq.). The organic phase was washed with brine, dried (Na₂SO₄) and concentrated at reduced pressure. The residue was purified by silica column chromatography (CHCl₃, CHCl₃-EtOAc 10:1) and recrystallized from EtOAc-heptane to give the title compound (5.57 g, 68%).

Examples 33-112

A library of di-acylated compounds was prepared by reacting starting materials (1,2-dihydro-4-hydroxy-1-methyl-2-oxo-quinoline-3-carboxanilides and 6,7-dihydro-4-hydroxy-7-methyl-6-oxo-thieno[2,3-b]pyridine-5-carboxanilides) with acylchlorides (acetylchloride, n-butyrylchloride, iso-butyrylchloride, benzoylchloride, and ethylchloroformate) according to the following general procedure:

A solution of the acylchloride (0.40 mmol) in CH₂Cl₂ (0.2 mL) was added to a solution of the starting material (0.10 mmol) and EtNiPr₂ (2.0 mmol) in CH₂Cl₂ (1.0 mL). The reaction mixture was shaken in a sealed vial for 30 min. A second portion of the acyl chloride (0.40 mmol) was added and shaking was continued for between 30 min and 24 h depending on the reactivity and solubility of the starting material. The reaction mixture was analyzed by TLC (silica, heptane-EtOAc, 1:1) and purified by silica column chromatography (heptane-EtOAc, 1:1) followed by crystallization from heptane-EtOAc to give the diacylated compound.

Example 33

N-acetyl-N-(4-trifluoromethylphenyl)-4-acetoxy-1,2-dihydro-5-methoxy-1-methyl-2-oxo-quinoline-3-carboxamide ¹H NMR: 2.30 (s, 3H), 2.33 (s, 3H), 3.63 (s, 3H), 3.90 (s, 3H), 6.72 (d, 1H), 6.98 (d, 1H), 7.50 (d, 2H), 7.52 (t, 1H), 7.67 (d, 2H).

Example 34

N-ethoxycarbonyl-N-(4-trifluoromethylphenyl)-4-ethoxycarbonyloxy-1,2-dihydro-5-methoxy-1-methyl-2-oxo-quinoline-3-carboxamide $^1$H NMR: 1.05 (t, 3H), 1.37 (t, 3H), 3.74 (s, 3H), 3.92 (s, 3H), 4.10 (q, 2H), 4.32 (q, 2H), 6.76 (d, 1H), 7.05 (d, 1H), 7.49 (d, 2H), 7.56 (t, 1H), 7.72 (d, 2H).

Example 35

N-acetyl-N-(4-fluorophenyl)-4-acetoxy-1,2-dihydro-5-methoxy-1-methyl-2-oxo-quinoline-3-carboxamide $^1$H NMR: 2.33 (s, 3H), 2.34 (s, 3H), 3.63 (s, 3H), 3.89 (s, 3H), 6.70 (d, 1H), 6.96 (d, 1H), 7.07 (t, 2H), 7.34 (m, 2H), 7.51 (t, 1H).

Example 36

N-iso-butyryl-N-(4-fluorophenyl)-4-iso-butyryloxy-1,2-dihydro-5-methoxy-1-methyl-2-oxo-quinoline-3-carboxamide $^1$H NMR: 1.17 (d, 6H), 1.33 (d, 6H), 2.85 (m, 1H), 3.09 (bm, 1H), 3.62 (s, 3H), 3.85 (s, 3H), 6.68 (d, 1H), 6.95 (d, 1H), 7.06 (t, 2H), 7.33 (m, 2H), 7.49 (t, 1H).

Example 37

N-acetyl-N-phenyl-4-acetoxy-5-ethyl-1,2-dihydro-1-methyl-2-oxo-quinoline-3-carboxamide $^1$H NMR: 1.28 (t, 3H), 2.16 (s, 3H), 2.34 (s, 3H), 2.99 (q, 2H), 3.70 (s, 3H), 7.10 (d, 1H), 7.28 (d, 1H), 7.35-7.55 (m, 6H).

Example 38

N-ethoxycarbonyl-N-phenyl-4-ethoxycarbonyloxy-5-ethyl-1,2-dihydro-1-methyl-2-oxo-quinoline-3-carboxamide $^1$H NMR: 1.06 (t, 3H), 1.29 (t, 3H), 1.36 (t, 3H), 3.04 (bm, 2H), 3.76 (s, 3H), 4.10 (q, 2H), 4.34 (q, 2H), 7.14 (d, 1H), 7.31-7.50 (m, 6H), 7.54 (t, 1H).

Example 39

N-acetyl-N-(4-chlorophenyl)-4-acetoxy-5-ethyl-1,2-dihydro-1-methyl-2-oxo-quinoline-3-carboxamide $^1$H NMR: 1.28 (t, 3H), 2.20 (s, 3H), 2.34 (s, 3H), 2.99 (q, 2H), 3.69 (s, 3H), 7.11 (d, 1H), 7.27-7.46 (m, 5H), 7.52 (dd, 1H).

Example 40

N-acetyl-N-phenyl-4-acetoxy-6,7-dihydro-3,7-dimethyl-6-oxo-thieno[2,3-b]pyridine-5-carboxamide $^1$H NMR: 2.11 (s, 3H), 2.32 (s, 3H), 2.35 (d, 3H), 3.62 (s, 3H), 6.59 (q, 1H), 7.31-7.53 (m, 5H).

Example 41

N-iso-butyryl-N-phenyl-4-iso-butyryloxy-6,7-dihydro-3,7-dimethyl-6-oxo-thieno[2,3-b]pyridine-5-carboxamide $^1$H NMR: 1.11 (d, 6H), 1.30 (d, 6H), 2.32 (d, 3H), 2.75 (m, 1H), 2.83 (m, 1H), 3.61 (s, 3H), 6.56 (q, 1H), 7.34-7.48 (m, 5H).

Example 42

N-benzoyl-N-phenyl-4-benzoyloxy-6,7-dihydro-3,7-dimethyl-6-oxo-thieno[2,3-b]pyridine-5-carboxamide $^1$H NMR: 2.26 (d, 3H), 3.62 (s, 3H), 6.57 (q, 1H), 7.13-7.38 (m, 8H), 7.51 (t, 2H), 7.65 (t, 1H), 7.77 (d, 2H), 8.19 (d, 2H).

Example 43

N-ethoxycarbonyl-N-phenyl-4-ethoxycarbonyloxy-6,7-dihydro-3,7-dimethyl-6-oxo-thieno[2,3-b]pyridine-5-carboxamide $^1$H NMR: 1.09 (t, 3H), 1.35 (t, 3H), 2.39 (d, 3H), 3.68 (s, 3H), 4.11 (q, 2H), 4.34 (q, 2H), 6.61 (q, 1H), 7.31-7.48 (m, 5H).

Example 44

N-iso-butyryl-N-(4-methoxyphenyl)-4-iso-butyryloxy-6,7-dihydro-3,7-dimethyl-6-oxo-thieno[2,3-b]pyridine-5-carboxamide $^1$H NMR: 1.10 (d, 6H), 1.30 (d, 6H), 2.32 (d, 3H), 2.73-2.89 (m, 2H), 3.60 (s, 3H), 3.83 (s, 3H), 6.56 (q, 1H), 6.93 (d, 2H), 7.27 (d, 2H).

Example 45

N-benzoyl-N-(4-methoxyphenyl)-4-benzoyloxy-6,7-dihydro-3,7-dimethyl-6-oxo-thieno[2,3-b]pyridine-5-carboxamide $^1$H NMR: 2.26 (d, 3H), 3.60 (s, 3H), 3.72 (s, 3H), 6.57 (q, 1H), 6.77 (d, 2H), 7.17 (d, 2H), 7.23-7.39 (m, 3H), 7.51 (t, 2H), 7.65 (t, 1H), 7.79 (d, 2H), 8.19 (d, 2H).

Example 46

N-ethoxycarbonyl-N-(4-methoxyphenyl)-4-ethoxycarbonyloxy-6,7-dihydro-3,7-dimethyl-6-oxo-thieno[2,3-b]pyridine-5-carboxamide $^1$H NMR: 1.10 (t, 3H), 1.36 (t, 3H), 2.39 (d, 3H), 3.67 (s, 3H), 3.84 (s, 3H), 4.11 (q, 2H), 4.33 (q, 2H), 6.61 (q, 1H), 6.95 (d, 2H), 7.25 (d, 2H).

Example 47

N-acetyl-N-(4-fluorophenyl)-4-acetoxy-6,7-dihydro-3,7-dimethyl-6-oxo-thieno[2,3-b]pyridine-5-carboxamide $^1$H NMR: 2.16 (s, 3H), 2.33 (s, 3H), 2.35 (d, 3H), 3.62 (s, 3H), 6.61 (q, 1H), 7.12 (t, 2H), 7.36 (m, 2H).

Example 48

N-iso-butyryl-N-(4-fluorophenyl)-4-iso-butyryloxy-6,7-dihydro-3,7-dimethyl-6-oxo-thieno[2,3-b]pyridine-5-carboxamide $^1$H NMR: 1.13 (d, 6H), 1.31 (d, 6H), 2.33 (d, 3H), 2.76-2.90 (m, 2H), 3.60 (s, 3H), 6.57 (q, 1H), 7.11 (t, 2H), 7.34 (m, 2H).

Example 49

N-benzoyl-N-(4-fluorophenyl)-4-benzoyloxy-6,7-dihydro-3,7-dimethyl-6-oxo-thieno[2,3-b]pyridine-5-carboxamide $^1$H NMR: 2.25 (d, 3H), 3.61 (s, 3H), 6.59 (q, 1H), 6.95 (t, 2H), 7.20-7.41 (m, 5H), 7.51 (t, 2H), 7.66 (t, 1H), 7.77 (d, 2H), 8.19 (d, 2H).

Example 50

N-ethoxycarbonyl-N-(4-fluorophenyl)-4-ethoxycarbonyloxy-6,7-dihydro-3,7-dimethyl-6-oxo-thieno[2,3-b]pyridine-5-carboxamide $^1$H NMR: 1.09 (t, 3H), 1.36 (t, 3H), 2.39 (d, 3H), 3.67 (s, 3H), 4.11 (q, 2H), 4.33 (q, 2H), 6.62 (q, 1H), 7.12 (t, 2H), 7.32 (m, 2H).

Example 51

Same Compound as Examples 30 and 32

N-acetyl-N-phenyl-4-acetoxy-1,2-dihydro-1-methyl-2-oxo-quinoline-3-carboxamide $^1$H NMR: 2.11 (s, 3H), 2.39 (s, 3H), 3.68 (s, 3H), 7.27 (t, 1H), 7.35-7.48 (m, 6H), 7.58-7.65 (m, 2H).

Example 52

N-iso-butyryl-N-phenyl-4-iso-butyryloxy-1,2-dihydro-1-methyl-2-oxo-quinoline-3-carboxamide $^1$H NMR: 1.10 (d, 6H), 1.37 (d, 6H), 2.74 (m, 1H), 2.92 (m, 1H), 3.69 (s, 3H), 7.25 (t, 1H), 7.35-7.50 (m, 6H), 7.56-7.65 (m, 2H).

Example 53

N-benzoyl-N-phenyl-4-benzoyloxy-1,2-dihydro-1-methyl-2-oxo-quinoline-3-carboxamide $^1$H NMR: 3.68 (s, 3H), 7.16-7.42 (m, 10H), 7.52 (t, 2H), 7.61-7.72 (m, 3H), 7.76 (d, 2H), 8.25 (d, 2H).

Example 54

N-ethoxycarbonyl-N-phenyl-4-ethoxycarbonyloxy-1,2-dihydro-1-methyl-2-oxo-quinoline-3-carboxamide $^1$H NMR: 1.06 (t, 3H), 1.38 (t, 3H), 3.75 (s, 3H), 4.11 (q, 2H), 4.35 (q, 2H), 7.31 (t, 2H), 7.34-7.50 (m, 6H), 7.66 (ddd, 1H), 7.77 (dd, 1H).

Example 55

N-acetyl-N-(4-methylphenyl)-4-acetoxy-1,2-dihydro-1-methyl-2-oxo-quinoline-3-carboxamide $^1$H NMR: 2.11 (s, 3H), 2.38 (s, 3H), 2.40 (s, 3H), 3.70 (s, 3H), 7.24-7.31 (m, 5H), 7.39 (dd, 1H), 7.60-7.66 (m, 2H).

Example 56

N-iso-butyryl-N-(4-methylphenyl)-4-iso-butyryloxy-1,2-dihydro-1-methyl-2-oxo-quinoline-3-carboxamide $^1$H NMR: 1.09 (d, 6H), 1.36 (d, 6H), 2.39 (s, 3H), 2.73 (m, 1H), 2.92 (m, 1H), 3.69 (s, 3H), 7.22-7.28 (m, 5H), 7.37 (d, 1H), 7.56-7.64 (m, 2H).

Example 57

N-benzoyl-N-(4-methylphenyl)-4-benzoyloxy-1,2-dihydro-1-methyl-2-oxo-quinoline-3-carboxamide $^1$H NMR: 2.26 (s, 3H), 3.68 (s, 3H), 7.06 (d, 2H), 7.15 (d, 2H), 7.20-7.40 (m, 5H), 7.54 (t, 2H), 7.58-7.71 (m, 3H), 7.78 (d, 2H), 8.25 (d, 2H).

Example 58

N-ethoxycarbonyl-N-(4-methylphenyl)-4-ethoxycarbonyloxy-1,2-dihydro-1-methyl-2-oxo-quinoline-3-carboxamide $^1$H NMR: 1.07 (t, 3H), 1.37 (t, 3H), 2.40 (s, 3H), 3.75 (s, 3H), 4.11 (q, 2H), 4.34 (q, 2H), 7.21-7.27 (m, 4H), 7.31 (t, 1H), 7.42 (d, 2H), 7.65 (ddd, 1H), 7.76 (dd, 1H).

Example 59

N-acetyl-N-(4-methoxyphenyl)-4-acetoxy-1,2-dihydro-1-methyl-2-oxo-quinoline-3-carboxamide $^1$H NMR: 2.15 (s, 3H), 2.40 (s, 3H), 3.69 (s, 3H), 3.82 (s, 3H), 6.95 (d, 2H), 7.24-7.32 (m, 3H), 7.38 (d, 1H), 7.59-7.66 (m, 2H).

Example 60

N-iso-butyryl-N-(4-methoxyphenyl)-4-iso-butyryloxy-1,2-dihydro-1-methyl-2-oxo-quinoline-3-carboxamide $^1$H NMR: 1.11 (d, 6H), 1.37 (d, 6H), 2.81 (m, 1H), 2.92 (m, 1H), 3.68 (s, 3H), 3.82 (s, 3H), 6.95 (d, 2H), 7.21-7.31 (m, 3H), 7.37 (d, 1H), 7.54-7.63 (m, 2H).

Example 61

N-benzoyl-N-(4-methoxyphenyl)-4-benzoyloxy-1,2-dihydro-1-methyl-2-oxo-quinoline-3-carboxamide $^1$H NMR: 3.68 (s, 3H), 3.72 (s, 3H), 6.77 (d, 2H), 7.16-7.41 (m, 7H), 7.54 (t, 2H), 7.59-7.73 (m, 3H), 7.79 (d, 2H), 8.25 (d, 2H).

Example 62

N-ethoxycarbonyl-N-(4-methoxyphenyl)-4-ethoxycarbonyloxy-1,2-dihydro-1-methyl-2-oxo-quinoline-3-carboxamide $^1$H NMR: 1.07 (t, 3H), 1.38 (t, 3H), 3.75 (s, 3H), 3.84 (s, 3H), 4.11 (q, 2H), 4.35 (q, 2H), 6.96 (d, 2H), 7.23-7.34 (m, 3H), 7.42 (d, 1H), 7.66 (ddd, 1H), 7.76 (dd, 1H).

Example 63

N-acetyl-N-(4-fluorophenyl)-4-acetoxy-1,2-dihydro-1-methyl-2-oxo-quinoline-3-carboxamide $^1$H NMR: 2.17 (s, 3H), 2.41 (s, 3H), 3.69 (s, 3H), 7.13 (t, 2H), 7.25-7.42 (m, 4H), 7.61-7.68 (m, 2H).

Example 64

N-iso-butyryl-N-(4-fluorophenyl)-4-iso-butyryloxy-1,2-dihydro-1-methyl-2-oxo-quinoline-3-carboxamide $^1$H NMR: 1.12 (d, 6H), 1.37 (d, 6H), 2.82 (m, 1H), 2.94 (m, 1H), 3.68 (s, 3H), 7.12 (dd, 2H), 7.26 (ddd, 1H), 7.31-7.40 (m, 3H), 7.56-7.65 (m, 2H).

Example 65

N-benzoyl-N-(4-fluorophenyl)-4-benzoyloxy-1,2-dihydro-1-methyl-2-oxo-quinoline-3-carboxamide $^1$H NMR: 3.68 (s, 3H), 6.96 (t, 2H), 7.22-7.41 (m, 7H), 7.55 (t, 2H), 7.60-7.73 (m, 3H), 7.77 (d, 2H), 8.25 (d, 2H).

Example 66

N-ethoxycarbonyl-N-(4-fluorophenyl)-4-ethoxycarbonyloxy-1,2-dihydro-1-methyl-2-oxo-quinoline-3-carboxamide $^1$H NMR: 1.04 (t, 3H), 1.38 (t, 3H), 3.74 (s, 3H), 4.10 (q, 2H), 4.35 (q, 2H), 7.14 (t, 2H), 7.26-7.38 (m, 5H), 7.43 (d, 1H), 7.66 (t, 1H), 7.78 (d, 1H).

Example 67

N-acetyl-N-(4-chlorophenyl)-4-acetoxy-1,2-dihydro-1-methyl-2-oxo-quinoline-3-carboxamide $^1$H NMR: 2.17 (s, 3H), 2.41 (s, 3H), 3.69 (s, 3H), 7.28-7.44 (m, 6H), 7.61-7.68 (m, 2H).

Example 68

N-iso-butyryl-N-(4-chlorophenyl)-4-iso-butyryloxy-1,2-dihydro-1-methyl-2-oxo-quinoline-3-carboxamide $^1$H NMR: 1.12 (d, 6H), 1.37 (d, 6H), 2.79 (m, 1H), 2.92 (m, 1H), 3.68 (s, 3H), 7.26 (ddd, 1H), 7.31 (d, 2H), 7.38 (d, 1H), 7.41 (d, 2H), 7.59 (dd, 1H), 7.62 (ddd, 1H).

Example 69

N-benzoyl-N-(4-chlorophenyl)-4-benzoyloxy-1,2-dihydro-1-methyl-2-oxo-quinoline-3-carboxamide $^1$H NMR: 3.67 (s, 3H), 7.18-7.42 (m, 9H), 7.54 (t, 2H), 7.61-7.73 (m, 3H), 7.78 (d, 2H), 8.25 (d, 2H).

Example 70

N-(4-chlorophenyl)-N-ethoxycarbonyl-4-ethoxycarbonyloxy-1,2-dihydro-1-methyl-2-oxo-quinoline-3-carboxamide $^1$H NMR: 1.07 (t, 3H), 1.38 (t, 3H), 3.75 (s, 3H), 4.11 (q, 2H), 4.35 (q, 2H), 7.26-7.35 (m, 3H), 7.40-7.46 (m, 3H), 7.66 (ddd, 1H), 7.79 (dd, 1H).

Example 71

N-acetyl-N-(4-trifluoromethylphenyl)-4-acetoxy-1,2-dihydro-1-methyl-2-oxo-quinoline-3-carboxamide $^1$H NMR: 2.16 (s, 3H), 2.41 (s, 3H), 3.70 (s, 3H), 7.30 (t, 1H), 7.40 (d, 1H), 7.53 (d, 2H), 7.60-7.70 (m, 2H), 7.72 (d, 2H).

Example 72

N-benzoyl-N-(4-trifluoromethylphenyl)-4-benzoyloxy-1,2-dihydro-1-methyl-2-oxo-quinoline-3-carboxamide $^1$H NMR: 3.67 (s, 3H), 7.22-7.42 (m, 7H), 7.50-7.58 (m, 4H), 7.61-7.72 (m, 2H), 7.76 (d, 2H), 8.25 (d, 2H).

Example 73

N-ethoxycarbonyl-N-(4-trifluoromethylphenyl)-4-ethoxycarbonyloxy-1,2-dihydro-1-methyl-2-oxo-quinoline-3-carboxamide $^1$H NMR: 1.07 (t, 3H), 1.38 (t, 3H), 3.76 (s, 3H), 4.12 (q, 2H), 4.35 (q, 2H), 7.33 (t, 1H), 7.44 (d, 1H), 7.50 (d, 2H), 7.68 (ddd, 1H), 7.73 (d, 2H), 7.80 (dd, 2H).

Example 74

N-acetyl-N-phenyl-4-acetoxy-5-chloro-1,2-dihydro-1-methyl-2-oxo-quinoline-3-carboxamide $^1$H NMR: 2.16 (s, 3H), 2.35 (s, 3H), 3.70 (s, 3H), 7.29 (dd, 1H), 7.32-7.51 (m, 7H).

Example 75

N-n-butyryl-N-phenyl-4-n-butyryloxy-5-chloro-1,2-dihydro-1-methyl-2-oxo-quinoline-3-carboxamide $^1$H NMR: 0.84 (t, 3H), 1.02 (t, 3H), 1.57 (m, 2H), 1.76 (m, 2H), 2.31 (bt, 2H), 2.60 (t, 2H), 3.72 (s, 3H), 7.28-7.51 (m, 7H).

Example 76

N-iso-butyryl-N-phenyl-4-iso-butyryloxy-5-chloro-1,2-dihydro-1-methyl-2-oxo-quinoline-3-carboxamide $^1$H NMR: 1.11 (d, 6H), 1.30 (d, 6H), 2.77 (bm, 1H), 2.87 (m, 1H), 3.69 (s, 3H), 7.26 (dd, 1H), 7.33-7.50 (m, 6H).

Example 77

N-benzoyl-N-phenyl-4-benzoyloxy-5-chloro-1,2-dihydro-1-methyl-2-oxo-quinoline-3-carboxamide $^1$H NMR: 3.70 (s, 3H), 7.16-7.38 (m, 10H), 7.45-7.56 (m, 3H), 7.65 (tt, 1H), 7.71 (bd, 2H), 8.22 (d, 2H).

Example 78

N-ethoxycarbonyl-N-phenyl-4-ethoxycarbonyloxy-5-chloro-1,2-dihydro-1-methyl-2-oxo-quinoline-3-carboxamide $^1$H NMR: 1.07 (t, 3H), 1.36 (t, 3H), 3.76 (s, 3H), 4.10 (q, 2H), 4.34 (q, 2H), 7.30-7.55 (m, 8H).

Example 79

N-ethoxycarbonyl-N-(4-methylphenyl)-5-chloro-4-ethoxycarbonyloxy-1,2-dihydro-1-methyl-2-oxo-quinoline-3-carboxamide $^1$H NMR: 1.08 (t, 3H), 1.36 (t, 3H), 2.40 (s, 3H), 3.76 (s, 3H), 4.10 (q, 2H), 4.33 (q, 2H), 7.20-7.30 (m, 4H), 7.32 (d, 1H), 7.38 (d, 1H), 7.51 (t, 1H).

Example 80

N-acetyl-N-(4-chlorophenyl)-4-acetoxy-5-chloro-1,2-dihydro-1-methyl-2-oxo-quinoline-3-carboxamide $^1$H NMR: 2.20 (s, 3H), 2.35 (s, 3H), 3.69 (s, 3H), 7.28-7.34 (m, 4H), 7.43 (d, 2H), 7.50 (t, 1H).

Example 81

N-n-butyryl-N-(4-chlorophenyl)-4-n-butyryloxy-5-chloro-1,2-dihydro-1-methyl-2-oxo-quinoline-3-carboxamide $^1$H NMR: 0.87 (t, 3H), 1.01 (t, 3H), 1.59 (m, 2H), 1.73 (m, 2H), 2.35 (bm, 2H), 2.60 (t, 2H), 3.69 (s, 3H), 7.27-7.52 (m, 7H).

Example 82

N-acetyl-N-(4-methoxyphenyl)-4-acetoxy-5-chloro-1,2-dihydro-1-methyl-2-oxo-quinoline-3-carboxamide $^1$H NMR: 2.18 (s, 3H), 2.34 (s, 3H), 3.70 (s, 3H), 3.82 (s, 3H), 6.95 (d, 2H), 7.24-7.41 (m, 4H), 7.48 (t, 1H).

Example 83

N-iso-butyryl-N-(4-methoxyphenyl)-4-iso-butyryloxy-5-chloro-1,2-dihydro-1-methyl-2-oxo-quinoline-3-carboxamide $^1$H NMR: 1.11 (d, 6H), 1.30 (d, 6H), 2.85 (bm, 1H), 2.87 (m, 1H), 3.69 (s, 3H), 3.83 (s, 3H), 6.94 (d, 2H), 7.24-7.30 (m, 3H), 7.32 (dd, 1H), 7.46 (dd, 1H).

Example 84

N-acetyl-N-phenyl-4-acetoxy-1,2-dihydro-6-methoxy-1-methyl-2-oxo-quinoline-3-carboxamide $^1$H NMR: 2.12 (s, 3H), 2.40 (s, 3H), 3.68 (s, 3H), 3.86 (s, 3H), 7.02 (d, 1H), 7.24 (dd, 1H), 7.32 (d, 1H), 7.36-7.50 (m, 5H).

Example 85

N-iso-butyryl-N-phenyl-4-iso-butyryloxy-1,2-dihydro-6-methoxy-1-methyl-2-oxo-quinoline-3-carboxamide $^1$H NMR: 1.11 (d, 6H), 1.38 (d, 6H), 2.75 (m, 1H), 2.93 (m, 1H), 3.67 (s, 3H), 3.83 (s, 3H), 6.99 (d, 1H), 7.21 (dd, 1H), 7.31 (d, 1H), 7.35-7.49 (m, 5H).

Example 86

N-benzoyl-N-phenyl-4-benzoyloxy-1,2-dihydro-6-methoxy-1-methyl-2-oxo-quinoline-3-carboxamide $^1$H NMR: 3.66 (m, 1H), 3.76 (s, 3H), 7.05 (d, 1H), 7.15-7.38 (m, 9H), 7.54 (t, 2H), 7.68 (tt, 1H), 7.77 (d, 2H), 8.25 (d, 2H).

Example 87

N-ethoxycarbonyl-N-phenyl-4-ethoxycarbonyloxy-1,2-dihydro-6-methoxy-1-methyl-2-oxo-quinoline-3-carboxamide $^1$H NMR: 1.06 (t, 3H), 1.38 (t, 3H), 3.73 (s, 3H), 3.87 (s, 3H), 4.10 (q, 2H), 4.35 (q, 2H), 7.16 (d, 1H), 7.26 (dd, 1H), 7.33-7.50 (m, 6H).

Example 88

N-acetyl-N-(4-fluorophenyl)-4-acetoxy-1,2-dihydro-6-methoxy-1-methyl-2-oxo-quinoline-3-carboxamide $^1$H NMR: 2.17 (s, 3H), 2.40 (s, 3H), 3.66 (s, 3H), 3.85 (s, 3H), 7.02 (d, 1H), 7.12 (t, 2H), 7.24 (dd, 1H), 7.32 (d, 1H), 7.36 (m, 2H).

Example 89

N-iso-butyryl-N-(4-fluorophenyl)-4-iso-butyryloxy-1,2-dihydro-6-methoxy-1-methyl-2-oxo-quinoline-3-carboxamide $^1$H NMR: 1.12 (d, 6H), 1.38 (d, 6H), 2.83 (m, 1H), 2.93 (m, 1H), 3.66 (s, 3H), 3.83 (s, 3H), 6.98 (d, 1H), 7.12 (t, 2H), 7.22 (dd, 1H), 7.31 (d, 1H), 7.36 (m, 2H).

Example 90

N-benzoyl-N-(4-fluorophenyl)-4-benzoyloxy-1,2-dihydro-6-methoxy-1-methyl-2-oxo-quinoline-3-carboxamide $^1$H NMR: 3.66 (s, 3H), 3.76 (s, 3H), 6.95 (t, 2H), 7.04 (d, 1H), 7.22-7.41 (m, 8H), 7.55 (t, 2H), 7.69 (tt, 1H), 7.77 (d, 2H), 8.25 (d, 2H).

Example 91

N-ethoxycarbonyl-N-(4-fluorophenyl)-4-ethoxycarbonyloxy-1,2-dihydro-6-methoxy-1-methyl-2-oxo-quinoline-3-carboxamide $^1$H NMR: 1.06 (t, 3H), 1.39 (t, 3H), 3.73 (s, 3H), 3.87 (s, 3H), 4.10 (q, 2H), 4.35 (q, 2H), 7.13 (t, 2H), 7.17 (d, 1H), 7.27 (dd, 1H), 7.31-7.39 (m, 3H).

Example 92

N-iso-butyryl-N-(4-chlorophenyl)-4-iso-butyryloxy-1,2-dihydro-6-methoxy-1-methyl-2-oxo-quinoline-3-carboxamide $^1$H NMR: 1.12 (d, 6H), 1.38 (d, 6H), 2.81 (m, 1H), 2.93 (m, 1H), 3.66 (s, 3H), 3.84 (s, 3H), 6.99 (d, 1H), 7.23 (dd, 1H), 7.30-7.35 (m, 3H), 7.41 (d, 2H).

Example 93

N-benzoyl-N-(4-chlorophenyl)-4-benzoyloxy-1,2-dihydro-6-methoxy-1-methyl-2-oxo-quinoline-3-carboxamide $^1$H NMR: 3.66 (s, 3H), 3.76 (s, 3H), 7.05 (d, 1H), 7.19-7.41 (m, 9H), 7.54 (t, 2H), 7.69 (tt, 1H), 7.77 (d, 2H), 8.24 (d, 2H).

Example 94

N-(4-chlorophenyl)-N-ethoxycarbonyl-4-ethoxycarbonyloxy-1,2-dihydro-6-methoxy-1-methyl-2-oxo-quinoline-3-carboxamide $^1$H NMR: 1.07 (t, 3H), 1.38 (t, 3H), 3.73 (s, 3H), 3.88 (s, 3H), 4.11 (q, 2H), 4.35 (q, 2H), 7.17 (d, 1H), 7.25-7.33 (m, 3H), 7.37 (d, 1H), 7.43 (d, 2H).

Example 95

N-acetyl-N-phenyl-4-acetoxy-6-chloro-1,2-dihydro-1-methyl-2-oxo-quinoline-3-carboxamide $^1$H NMR: 2.09 (s, 3H), 2.41 (s, 3H), 3.68 (s, 3H), 7.32 (d, 1H), 7.35-7.51 (m, 5H), 7.55-7.60 (m, 2H).

Example 96

N-n-butyryl-N-phenyl-4-n-butyryloxy-6-chloro-1,2-dihydro-1-methyl-2-oxo-quinoline-3-carboxamide $^1$H NMR: 0.83 (t, 3H), 1.06 (t, 3H), 1.56 (m, 2H), 1.82 (m, 2H), 2.25 (bt, 2H), 2.66 (t, 2H), 3.68 (s, 3H), 7.30-7.52 (m, 6H), 7.54-7.59 (m, 2H).

Example 97

N-iso-butyryl-N-phenyl-4-iso-butyryloxy-6-chloro-1,2-dihydro-1-methyl-2-oxo-quinoline-3-carboxamide $^1$H NMR: 1.10 (d, 6H), 1.37 (d, 6H), 2.68 (m, 1H), 2.98 (m, 1H), 3.67 (s, 3H), 7.31 (d, 1H), 7.35-7.51 (m, 5H), 7.52-7.58 (m, 2H).

Example 98

N-benzoyl-N-phenyl-4-benzoyloxy-6-chloro-1,2-dihydro-1-methyl-2-oxo-quinoline-3-carboxamide $^1$H NMR: 3.65 (s, 3H), 7.16-7.38 (m, 9H), 7.51-7.61 (m, 4H), 7.66-7.76 (m, 3H), 8.25 (d, 2H).

Example 99

N-ethoxycarbonyl-N-phenyl-4-ethoxycarbonyloxy-6-chloro-1,2-dihydro-1-methyl-2-oxo-quinoline-3-carboxamide $^1$H NMR: 1.08 (t, 3H), 1.389 (t, 3H), 3.73 (s, 3H), 4.11 (q, 2H), 4.37 (q, 2H), 7.33-7.50 (m, 6H), 7.59 (dd, 1H), 7.74 (d, 1H).

Example 100

N-acetyl-N-(4-fluorophenyl)-4-acetoxy-6-chloro-1,2-dihydro-1-methyl-2-oxo-quinoline-3-carboxamide $^1$H NMR: 2.12 (s, 3H), 2.41 (s, 3H), 3.67 (s, 3H), 7.15 (dd, 2H), 7.30-7.39 (m, 3H), 7.55-7.60 (m, 2H).

Example 101

N-iso-butyryl-N-(4-fluorophenyl)-4-iso-butyryloxy-6-chloro-1,2-dihydro-1-methyl-2-oxo-quinoline-3-carboxamide $^1$H NMR: 1.10 (d, 6H), 1.37 (d, 6H), 2.73 (m, 1H), 2.93 (m, 1H), 3.67 (s, 3H), 7.14 (dd, 2H), 7.30-7.38 (m, 3H), 7.52-7.58 (m, 2H).

Example 102

N-benzoyl-N-(4-fluorophenyl)-4-benzoyloxy-6-chloro-1,2-dihydro1-methyl-2-oxo-quinoline-3-carboxamide $^1$H NMR: 3.66 (s, 3H), 6.95 (dd, 2H), 7.18-7.40 (m, 6H), 7.52-7.62 (m, 4H), 7.67-7.75 (m, 3H), 8.24 (d, 2H).

Example 103

N-ethoxycarbonyl-N-(4-fluorophenyl)-6-chloro-4-ethoxycarbonyloxy-1,2-dihydro-1-methyl-2-oxo-quinoline-3-carboxamide $^1$H NMR: 1.08 (t, 3H), 1.39 (t, 3H), 3.73 (s, 3H), 4.11 (q, 2H), 4.36 (q, 2H), 7.14 (t, 2H), 7.33 (m, 2H), 7.36 (d, 1H), 7.60 (dd, 1H), 7.75 (d, 1H).

Example 104

N-acetyl-N-(4-chlorophenyl)-4-acetoxy-6-chloro-1,2-dihydro-1-methyl-2-oxo-quinoline-3-carboxamide ¹H NMR: 2.13 (s, 3H), 2.41 (s, 3H), 3.68 (s, 3H), 7.29-7.36 (m, 3H), 7.44 (d, 2H), 7.56-7.61 (m, 2H).

Example 105

N-n-butyryl-N-(4-chlorophenyl)-4-n-butyryloxy-6-chloro-1,2-dihydro-1-methyl-2-oxo-quinoline-3-carboxamide ¹H NMR: 0.85 (t, 3H), 1.06 (t, 3H), 1.57 (m, 2H), 1.81 (m, 2H), 2.27 (bt, 2H), 2.65 (t, 2H), 3.66 (s, 3H), 7.27-7.35 (m, 3H), 7.45 (d, 2H), 7.54-7.59 (m, 2H).

Example 106

N-iso-butyryl-N-(4-chlorophenyl)-4-iso-butyryloxy-6-chloro-1,2-dihydro-1-methyl-2-oxo-quinoline-3-carboxamide ¹H NMR: 1.10 (d, 6H), 1.36 (d, 6H), 2.71 (m, 1H), 2.92 (m, 1H), 3.67 (s, 3H), 7.28-7.35 (m, 2H), 7.44 (d, 2H), 7.53-7.59 (m, 2H).

Example 107

N-benzoyl-N-(4-chlorophenyl)-4-benzoyloxy-6-chloro-1,2-dihydro1-methyl-2-oxo-quinoline-3-carboxamide ¹H NMR: 3.66 (s, 3H), 7.16-7.40 (m, 8H), 7.52-7.62 (m, 4H), 7.67-7.75 (m, 3H), 8.23 (d, 2H).

Example 108

N-(4-chlorophenyl)-N-ethoxycarbonyl-6-chloro-4-ethoxycarbonyloxy-1,2-dihydro-1-methyl-2-oxo-quinoline-3-carboxamide ¹H NMR: 1.08 (t, 3H), 1.39 (t, 3H), 3.72 (s, 3H), 4.11 (q, 2H), 4.36 (q, 2H), 7.29 (d, 2H), 7.36 (d, 1H), 7.45 (d, 2H), 7.60 (dd, 1H), 7.75 (d, 1H).

Example 109

N-acetyl-N-(4-methoxyphenyl)-4-acetoxy-6-chloro-1,2-dihydro-1-methyl-2-oxo-quinoline-3-carboxamide ¹H NMR: 2.12 (s, 3H), 2.41 (s, 3H), 3.68 (s, 3H), 3.83 (s, 3H), 6.96 (d, 2H), 7.28 (bd, 2H), 7.32 (d, 1H), 7.54-7.59 (m, 2H).

Example 110

N-iso-butyryl-N-(4-methoxyphenyl)-4-iso-butyryloxy-6-chloro-1,2-dihydro-1-methyl-2-oxo-quinoline-3-carboxamide ¹H NMR: 1.09 (d, 6H), 1.37 (d, 6H), 2.75 (bm, 1H), 2.92 (m, 1H), 3.67 (s, 3H), 3.83 (s, 3H), 6.96 (d, 2H), 7.27 (d, 2H), 7.31 (d, 1H), 7.50-7.58 (m, 2H).

Example 111

N-benzoyl-N-(4-methoxyphenyl)-4-benzoyloxy-6-chloro-1,2-dihydro1-methyl-2-oxo-quinoline-3-carboxamide ¹H NMR: 3.67 (s, 3H), 3.72 (s, 3H), 6.77 (d, 2H), 7.17 (d, 2H), 7.23-7.40 (m, 4H), 7.51-7.61 (m, 4H), 7.66-7.78 (m, 3H), 8.24 (d, 2H).

Example 112

N-ethoxycarbonyl-N-(4-methoxyphenyl)-6-chloro-4-ethoxycarbonyloxy-1,2-dihydro-1-methyl-2-oxo-quinoline-3-carboxamide ¹H NMR: 1.08 (t, 3H), 1.39 (t, 3H), 3.72 (s, 3H), 3.84 (s, 3H), 4.10 (q, 2H), 4.36 (q, 2H), 6.96 (d, 2H), 7.26 (d, 2H), 7.35 (d, 1H), 7.59 (dd, 1H), 7.73 (d, 1H).

Example 113

Same Compound as Example 31

N-phenyl-4-acetoxy-1,2-dihydro-1-methyl-2-oxo-quinoline-3-carboxamide

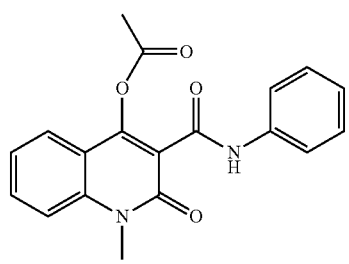 [SMILES: CC(=O)Oc1c(C(=O)Nc2ccccc2)c(=O)n(C)c2ccccc12]

A solution of NaOH in MeOH (0.50 mL, 0.20 M, 0.10 mmol) was added to a solution of N-acetyl-N-phenyl-4-acetoxy-1,2-dihydro-1-methyl-2-oxo-quinoline-3-carboxamide (38 mg, 0.10 mmol) in MeOH (1.0 mL) and THF (0.5 mL). After stirring for 3 min, the solution was neutralized with aq. HCl (0.2 mL, 0.5 M) and further diluted with water (ca 10 mL). The precipitated product (29 mg, 86%) was collected by filtration and washed with water.

The following compounds were prepared by the same method:

Example 114

N-(4-fluorophenyl)-4-acetoxy-6-chloro-1,2-dihydro-1-methyl-2-oxo-quinoline-3-carboxamide

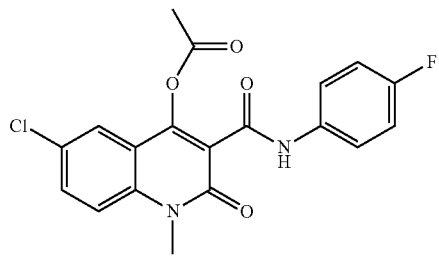 [SMILES: CC(=O)Oc1c(C(=O)Nc2ccc(F)cc2)c(=O)n(C)c2ccc(Cl)cc12]

Yield: 39 mg (quant.).
$^1$H NMR: 2.57 (s, 3H), 3.81 (s, 3H), 7.04 (t, 2H), 7.42 (d, 1H), 7.65 (m, 2H), 7.69 (dd, 1H), 7.89 (d, 1H), 11.77 (s, 1H).

Example 115

N-(4-chlorophenyl)-4-acetoxy-6-chloro-1,2-dihydro-1-methyl-2-oxo-quinoline-3-carboxamide

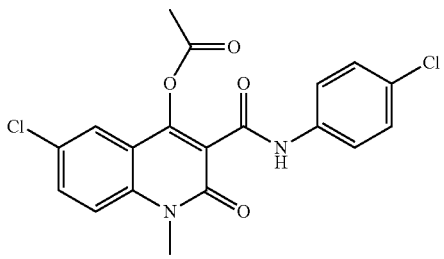 [SMILES: CC(=O)Oc1c(C(=O)Nc2ccc(Cl)cc2)c(=O)n(C)c2ccc(Cl)cc12]

Yield: (40 mg, 98%).
$^1$H NMR: 2.58 (s, 3H), 3.81 (s, 3H), 7.31 (d, 2H), 7.42 (d, 1H), 7.64 (d, 2H), 7.69 (dd, 1H), 7.89 (d, 1H), 11.87 (s, 1H).

Example 116

N-(4-methoxyphenyl)-4-acetoxy-6-chloro-1,2-dihydro-1-methyl-2-oxo-quinoline-3-carboxamide

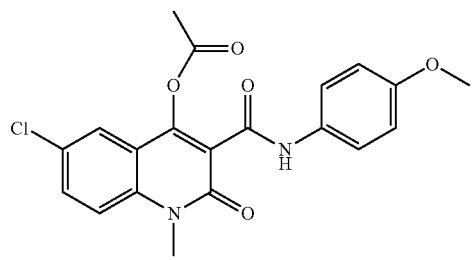 [SMILES: COc1ccc(NC(=O)c2c(OC(C)=O)c3cc(Cl)ccc3n(C)c2=O)cc1]

Yield: (38 mg, 95%).
$^1$H NMR: 2.57 (s, 3H), 3.80 (s, 3H), 3.81 (s, 3H), 6.89 (d, 2H), 7.41 (d, 1H), 7.59 (d, 2H), 7.67 (dd, 1H), 7.88 (d, 1H), 11.59 (s, 1H).

Example 117

N-phenyl-4-dibenzylphosphoryloxy-1,2-dihydro-1-methyl-2-oxo-quinoline-3-carboxamide N-(2,4-dimethoxybenzyl)-aniline

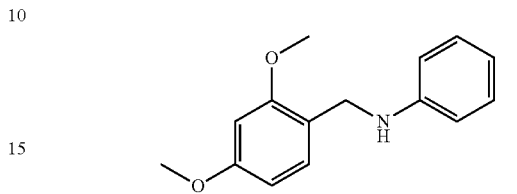

Trifluoroaceticacid (10 drops) was added to a solution of 2,4-dimethoxybenzaldehyde (16.62 g, 100 mmol) and aniline (9.31 g, 100 mmol) in toluene (100 mL). The reaction mixture was stirred at reflux temperature and toluene/water was distilled off during 1.5 h. After cooling the reaction mixture was concentrated at reduced pressure and the residue was dissolved in MeOH (200 mL). NaBH$_4$ (2.0 g, 54 mmol) was added in portions during 20 min and the reaction mixture was then stirred for 1 h. The product (22.16 g, 91%) crystallized from the reaction mixture and was isolated by filtration.

$^1$H NMR: 3.80 (s, 3H), 3.84 (s, 3H), 4.05 (bs, 1H), 4.26 (s, 2H), 6.44 (dd, 1H), 6.47 (d, 1H), 6.66 (m, 2H), 6.70 (tt, 1H), 7.17 (m, 2H), 7.21 (d, 1H).

N-(2,4-dimethoxybenzyl)-N-phenyl-1,2-dihydro-4-hydroxy-1-methyl-2-oxo-quinoline-3-carboxamide

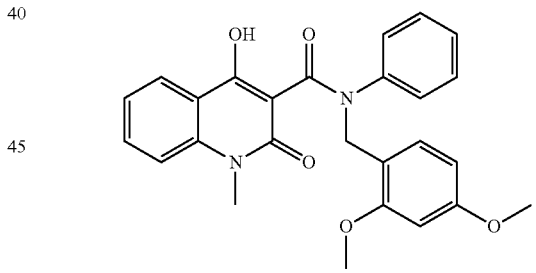

A solution of ethyl 1,2-dihydro-4-hydroxy-1-methyl-2-oxo-quinoline-3-carboxylate (9.25 g, 37.4 mmol) and N-(2,4-dimethoxybenzyl)-aniline (9.10 g, 37.4 mmol) in heptane (200 mL) was stirred at 110° C. under a flow of N$_2$ for 6 h letting the EtOH evaporate from the reaction mixture. The product started to precipitate and some extra heptane was added. The reaction mixture was then stirred at 100° C. overnight, still under a gentle flow of N$_2$. The product (12.21 g, 73%) crystallized from the reaction mixture and was collected by filtration while still warm (ca 50° C.).

$^1$H NMR: 3.30 (bs, 3H), 3.69 (s, 3H), 3.77 (s, 3H), 5.09 (s, 2H), 6.39 (d, 1H), 6.46 (bd, 1H), 7.07-7.19 (m, 5H), 7.20 (bd, 1H), 7.24 (t, 1H), 7.47 (bs, 1H), 7.59 (ddd, 1H), 8.12 (dd, 1H), 12.09 (bs, 1H).

N-(2,4-dimethoxybenzyl)-N-phenyl-4-dibenzylphosphoryloxy-1,2-dihydro-1-methyl-2-oxo-quinoline-3-carboxamide

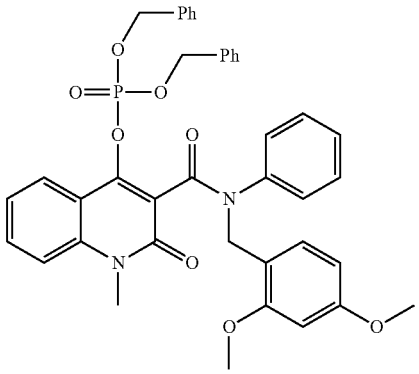 [SMILES: COc1ccc(CN(C(=O)c2c(OP(=O)(OCc3ccccc3)OCc3ccccc3)c3ccccc3n(C)c2=O)c2ccccc2)c(OC)c1]

CCl₄ (154 mg, 1.00 mmol) was added to a solution of EtNiPr₂ (52 mg, 0.40 mmol), DMAP (5 mg, 0.04 mmol) and (PhCH₂O)₂POH (79 mg, 0.30 mmol) in dry MeCN (1.5 mL). The reaction mixture was stirred for 3 min and was then added to a slurry of N-(2,4-dimethoxybenzyl)-N-phenyl-1,2-dihydro-4-hydroxy-1-methyl-2-oxo-quinoline-3-carboxamide (44 mg, 0.10 mmol) in dry MeCN (0.5 mL). The reaction mixture was stirred at room temperature for 20 min and was then concentrated at reduced pressure. The residue was purified by silica column chromatography (heptane-EtOAc, 1:2, then EtOAc) to give the title compound (62 mg, 88%).

¹H NMR: 3.54 (s, 3H), 3.55 (s, 3H), 3.73 (s, 3H), 4.78 (d, 1H), 5.12-5.29 (m, 5H), 6.29 (d, 1H), 6.44 (dd, 1H), 6.91-7.05 (m, 3H), 7.12 (t, 1H), 7.14-7.42 (m, 5H), 7.48 (ddd, 1H), 7.61 (d, 1H), 7.89 (dd, 1H).

N-phenyl-4-dibenzylphosphoryloxy-1,2-dihydro-1-methyl-2-oxo-quinoline-3-carboxamide

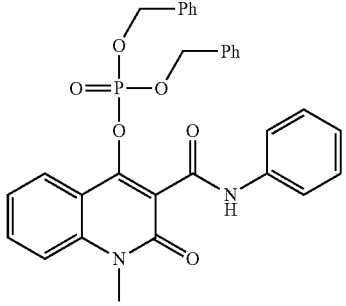 [SMILES: Cn1c(=O)c(C(=O)Nc2ccccc2)c(OP(=O)(OCc2ccccc2)OCc2ccccc2)c2ccccc21]

N-(2,4-dimethoxybenzyl)-N-phenyl-4-dibenzylphosphoryloxy-1,2-dihydro-1-methyl-2-oxo-quinoline-3-carboxamide (116 mg, 0.165 mmol) was added to a solution of cerium ammonium nitrate (CAN, 226 mg, 0.412 mmol, 2.5 eq.) in aq. MeCN (95%, 8.0 mL). The reaction mixture was stirred at room temperature for 1 h, concentrated at reduced pressure, and then partitioned between EtOAc and water. The organic phase was washed with water and brine, dried (Na₂SO₄), and concentrated at reduced pressure. The residue was purified by silica column chromatography (heptane-EtOAc, 1:1, then 1:2) to give the title compound (61 mg, 67%).

¹H NMR: 3.78 (s, 3H), 5.20 (m, 4H), 7.11 (t, 1H), 7.21 (d, 1H), 7.25-7.31 (m, 10H), 7.33 (t, 2H), 7.41 (d, 1H), 7.69 (t, 1H), 7.72 (d, 2H), 8.16 (d, 1H), 10.52 (s, 1H).

Example 118

N-phenyl-4-phosphoryloxy-1,2-dihydro-1-methyl-2-oxo-quinoline-3-carboxamide di-sodium salt

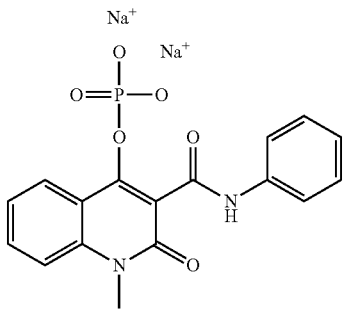 [SMILES: [Na+] ; [Na+] ; Cn1c(=O)c(C(=O)Nc2ccccc2)c(OP(=O)(O)O)c2ccccc21]

N-phenyl-4-dibenzylphosphoryloxy-1,2-dihydro-1-methyl-2-oxo-quinoline-3-carboxamide (14 mg, 0.025 mmol) was hydrogenated at 1 atm. H₂ at room temperature for 30 min in methanol (2 mL) in the presence of Na₂CO₃ (10 mg, 0.10 mmol) using Pd/C (10%, 8 mg) as catalyst. The reaction mixture was filtered and concentrated at reduced pressure to give the title compound.

¹H NMR (CD₃OD): 3.73 (s, 3H), 7.07 (t, 1H), 7.27-7.34 (m, 3H), 7.51 (d, 1H), 7.64 (ddd, 1H), 7.92 (d, 2H), 8.69 (dd, 1H).

Example 119

N-phenyl-4-diethylphosphoryloxy-1,2-dihydro-1-methyl-2-oxo-quinoline-3-carboxamide N-(2,4-dimethoxybenzyl)-N-phenyl-4-diethylphosphoryloxy-1,2-dihydro-1-methyl-2-oxo-quinoline-3-carboxamide

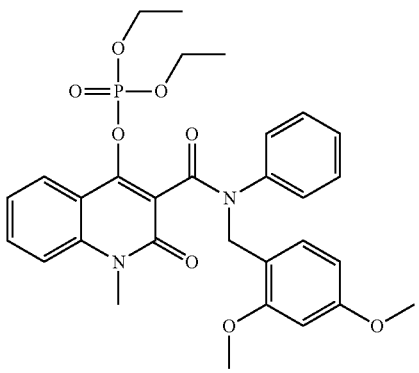 [SMILES: CCOP(=O)(OCC)Oc1c(C(=O)N(Cc2ccc(OC)cc2OC)c2ccccc2)c(=O)n(C)c2ccccc12]

Diethylphosphorylchloride (150 mg, 0.87 mmol) was added to a solution of EtNiPr₂ (129 mg, 1.00 mmol), DMAP (10 mg, 0.08 mmol) and N-(2,4-dimethoxybenzyl)-N-phenyl-1,2-dihydro-4-hydroxy-1-methyl-2-oxo-quinoline-3-carboxamide (222 mg, 050 mmol) in CH₂Cl₂ (3.0 mL). The reaction mixture was stirred for 30 min and was then concentrated at reduced pressure. The residue was purified by silica column chromatography (EtOAc) to give the title compound (196 mg, 68%).

¹H NMR: 1.31 (t, 3H), 1.45 (t, 3H), 3.59 (s, 3H), 3.59 (s, 3H), 3.78 (s, 3H), 4.20-4.43 (m, 4H), 4.83 (d, 1H), 5.35 (d, 1H), 6.33 (d, 1H), 6.54 (dd, 1H), 7.00-7.44 (m, 7H), 7.54 (ddd, 1H), 7.66 (d, 1H), 7.99 (dd, 1H).

N-phenyl-4-diethylphosphoryloxy-1,2-dihydro-1-methyl-2-oxo-quinoline-3-carboxamide

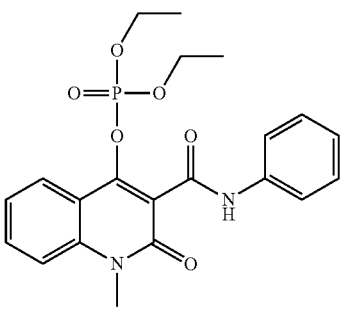 [SMILES: CCOP(=O)(OCC)Oc1c(C(=O)Nc2ccccc2)c(=O)n(C)c2ccccc12]

N-(2,4-dimethoxybenzyl)-N-phenyl-4-diethylphosphoryloxy-1,2-dihydro-1-methyl-2-oxo-quinoline-3-carboxamide (125 mg, 0.22 mmol) was added to a solution of cerium ammonium nitrate in 95% aq. MeCN (0.50 mmol, 0.1 M, 5.0 mL). The reaction mixture was stirred at room temperature for 1 h, concentrated at reduced pressure, and then partitioned between EtOAc and water. The organic phase was washed with water and brine, dried ($Na_2SO_4$), and concentrated at reduced pressure. The residue was purified by silica column chromatography (EtOAc) to give the title compound (45 mg, 49%).

$^1$H NMR: 1.33 (dt, 6H), 3.79 (s, 3H), 4.30 (m, 4H), 7.12 (tt, 1H), 7.31-7.41 (m, 3H), 7.44 (d, 1H), 7.68-7.75 (m, 3H), 8.20 (dd, 1H), 10.35 (s, 1H).

Examples 120-126 were prepared by methods as described for Example 1 and Example 18.

Example 120

N-(4-fluorophenyl)-5-chloro-1,2-dihydro-4-hydroxy-1-methyl-2-oxo-quinoline-3-carboxamide

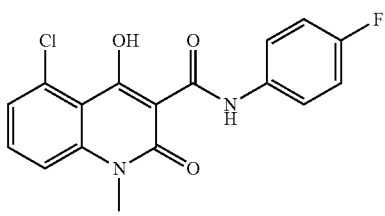 [SMILES: Cn1c(=O)c(C(=O)Nc2ccc(F)cc2)c(O)c2c(Cl)cccc21]

$^1$H NMR: 3.74 (s, 3H), 7.09 (t, 2H), 7.35 (dd, 1H), 7.36 (dd, 1H), 7.56 (t, 1H), 7.65 (m, 2H), 12.62 (s, 1H).

Example 121

N-(4-trifluoromethylphenyl)-5-chloro-1,2-dihydro-4-hydroxy-1-methyl-2-oxo-quinoline-3-carboxamide

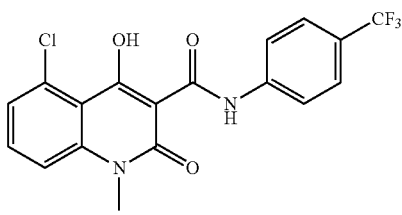 [SMILES: Cn1c(=O)c(C(=O)Nc2ccc(C(F)(F)F)cc2)c(O)c2c(Cl)cccc21]

$^1$H NMR: 3.74 (s, 3H), 7.34 (dd, 1H), 7.35 (dd, 1H), 7.56 (t, 1H), 7.63 (d, 2H), 7.80 (d, 2H), 12.90 (s, 1H).

Example 122

N-(4-fluorophenyl)-5-ethyl-1,2-dihydro-4-hydroxy-1-methyl-2-oxo-quinoline-3-carboxamide

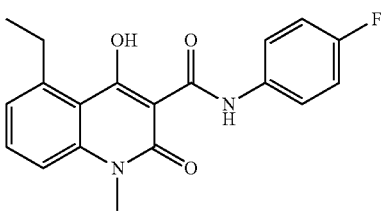 [SMILES: CCc1cccc2c1c(O)c(C(=O)Nc1ccc(F)cc1)c(=O)n2C]

$^1$H NMR: 1.31 (t, 3H), 3.32 (q, 2H), 3.74 (s, 3H), 7.08 (t, 2H), 7.14 (d, 1H), 7.29 (d, 1H), 7.59 (dd, 1H), 7.66 (m, 2H), 12.79 (s, 1H).

Example 123

N-(4-trifluoromethylphenyl)-5-ethyl-1,2-dihydro-4-hydroxy-1-methyl-2-oxo-quinoline-3-carboxamide

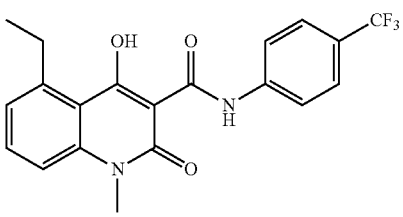 [SMILES: CCc1cccc2c1c(O)c(C(=O)Nc1ccc(C(F)(F)F)cc1)c(=O)n2C]

$^1$H NMR: 1.32 (t, 3H), 3.32 (q, 2H), 3.73 (s, 3H), 7.14 (d, 1H), 7.29 (d, 1H), 7.60 (dd, 1H), 7.63 (d, 2H), 7.82 (d, 2H), 13.09 (s, 1H).

Example 124

N-(4-methoxyphenyl)-5-ethyl-1,2-dihydro-4-hydroxy-1-methyl-2-oxo-quinoline-3-carboxamide

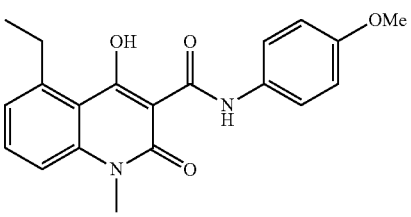 [SMILES: CCc1cccc2c1c(O)c(C(=O)Nc1ccc(OC)cc1)c(=O)n2C]

$^1$H NMR: 1.31 (t, 3H), 3.32 (q, 2H), 3.73 (s, 3H), 3.83 (s, 3H), 6.93 (d, 2H), 7.13 (d, 1H), 7.28 (d, 1H), 7.58 (dd, 1H), 7.60 (d, 2H), 12.63 (s, 1H).

Example 125

N-(4-chlorophenyl)-1,2-dihydro-4-hydroxy-5-methoxy-1-methyl-2-oxo-quinoline-3-carboxamide

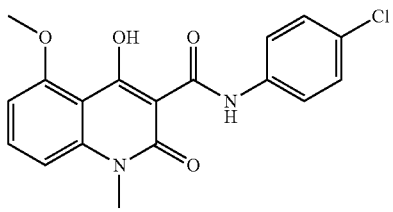 [SMILES: COc1cccc2c1c(O)c(C(=O)Nc1ccc(Cl)cc1)c(=O)n2C]

$^1$H NMR: 3.71 (s, 3H), 4.03 (s, 3H), 6.80 (d, 1H), 7.00 (d, 1H), 7.33 (d, 2H), 7.62 (t, 1H), 7.64 (d, 2H), 12.79 (s, 1H).

Example 126

N-(4-methoxyphenyl)-1,2-dihydro-4-hydroxy-5-methoxy-1-methyl-2-oxo-quinoline-5-carboxamide

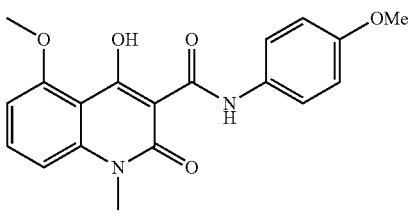 [SMILES: COc1ccc(NC(=O)c2c(O)c3c(OC)cccc3n(C)c2=O)cc1]

¹H NMR: 3.71 (s, 3H), 3.82 (s, 3H), 4.02 (s, 3H), 6.79 (d, 1H), 6.92 (d, 2H), 6.99 (d, 1H), 7.59 (d, 2H), 7.60 (t, 1H), 12.54 (s, 1H).

Examples 127-163

A library of di-acylated compounds was prepared by reacting starting materials (1,2-dihydro-4-hydroxy-1-methyl-2-oxo-quinoline-3-carboxanilides and 6,7-dihydro-4-hydroxy-7-methyl-6-oxo-thieno[2,3-b]pyridine-5-carboxanilides) with acylchlorides (acetylchloride, iso-butyrylchloride, and benzoylchloride according to the following general procedure:

The acyl chloride (0.80 mmol) was added in portions during 1-4 h to a solution of the starting material (0.20 mmol) and EtNiPr₂ (1.00 mmol) in CH₂Cl₂ (1-2 mL). The reaction mixture was shaken in a sealed vial at 50° C. for 4-48 h. The reaction mixture was analyzed by TLC (silica, heptane-EtOAc, 1:1) and the product was purified by silica column chromatography (heptane-EtOAc 2:1, 1:1, 0:1) followed by crystallization from heptane-EtOAc to give the diacylated compound.

Example 127

N-acetyl-N-phenyl-4-acetoxy-1,2-dihydro-5-methoxy-1-methyl-2-oxo-quinoline-3-carboxamide ¹H NMR: 2.23 (s, 3H), 2.33 (s, 3H), 3.65 (s, 3H), 3.90 (s, 3H), 6.71 (d, 1H), 6.98 (d, 1H), 7.31-7.48 (m, 5H), 7.51 (t, 1H).

Example 128

N-iso-butyryl-N-phenyl-4-iso-butyryloxy-1,2-dihydro-5-methoxy-1-methyl-2-oxo-quinoline-3-carboxamide ¹H NMR: 1.14 (d, 6H), 1.33 (d, 6H), 2.85 (m, 1H), 2.93 (broad m, 1H), 3.64 (s, 3H), 3.85 (s, 3H), 6.68 (d, 1H), 6.97 (d, 1H), 7.33-7.46 (m, 5H), 7.48 (t, 1H).

Example 129

N-benzoyl-N-phenyl-4-benzoyloxy-1,2-dihydro-5-methoxy-1-methyl-2-oxo-quinoline-3-carboxamide ¹H NMR: 3.50 (s, 3H), 3.65 (s, 3H), 6.64 (d, 1H), 6.96 (d, 1H), 7.17-7.40 (m, 8H), 7.46-7.58 (m, 3H), 7.66 (tt, 1H), 7.82 (broad d, 2H), 8.22 (d, 2H).

Example 130

N-iso-butyryl-N-(4-trifluoromethylphenyl)-4-iso-butyryloxy-1,2-dihydro-5-methoxy-1-methyl-2-oxo-quinoline-3-carboxamide ¹H NMR: 1.17 (d, 6H), 1.33 (d, 6H), 2.86 (m, 1H), 2.98 (broad m, 1H), 3.64 (s, 3H), 3.87 (s, 3H), 6.70 (d, 1H), 6.97 (d, 1H), 7.46-7.54 (m, 3H), 7.68 (d, 2H).

Example 131

N-benzoyl-N-(4-trifluoromethylphenyl)-4-benzoyloxy-1,2-dihydro-5-methoxy-1-methyl-2-oxo-quinoline-3-carboxamide ¹H NMR: 3.50 (s, 3H), 3.64 (s, 3H), 6.65 (d, 1H), 6.97 (d, 1H), 7.29 (t, 2H), 7.39 (tt, 1H), 7.42 (d, 2H), 7.49-7.59 (m, 5H), 7.67 (tt, 1H), 7.80 (broad d, 2H), 8.21 (d, 2H).

Example 132

N-benzoyl-N-(4-fluorophenyl)-4-benzoyloxy-1,2-dihydro-5-methoxy-1-methyl-2-oxo-quinoline-3-carboxamide ¹H NMR: 3.50 (s, 3H), 3.65 (s, 3H), 6.64 (d, 1H), 6.97 (d, 1H), 6.97 (t, 2H), 7.24-7.34 (m, 4H), 7.39 (tt, 1H), 7.51 (t, 2H), 7.51-7.59 (m, 2H), 7.67 (tt, 1H), 7.83 (broad d, 2H), 8.21 (d, 2H).

Example 133

N-iso-butyryl-N-phenyl-4-iso-butyryloxy-5-ethyl-1,2-dihydro-1-methyl-2-oxo-quinoline-3-carboxamide ¹H NMR: 1.13 (d, 6H), 1.26 (t, 3H), 1.32 (d, 6H), 2.84 (m, 1H), 2.85 (broad m, 1H), 2.97 (q, 2H), 3.69 (s, 3H), 7.08 (d, 1H), 7.27 (d, 1H), 7.34-7.44 (m, 5H), 7.49 (dd, 1H).

Example 134

N-benzoyl-N-phenyl-4-benzoyloxy-5-ethyl-1,2-dihydro-1-methyl-2-oxo-quinoline-3-carboxamide ¹H NMR: 1.21 (t, 3H), 2.92 (q, 2H), 3.70 (s, 3H), 7.08 (d, 1H), 7.15-7.39 (m, 9H), 7.48-7.58 (m, 3H), 7.68 (tt, 1H), 7.80 (broad d, 2H), 8.21 (d, 2H).

Example 135

N-iso-butyryl-N-(4-chlorophenyl)-4-iso-butyryloxy-5-ethyl-1,2-dihydro-1-methyl-2-oxo-quinoline-3-carboxamide ¹H NMR: 1.14 (d, 6H), 1.26 (t, 3H), 1.32 (d, 6H), 2.84 (m, 1H), 2.88 (broad m, 1H), 2.98 (q, 2H), 3.69 (s, 3H), 7.09 (d, 1H), 7.28 (d, 1H), 7.32 (d, 2H), 7.40 (d, 2H), 7.51 (dd, 1H).

Example 136

N-benzoyl-N-(4-chlorophenyl)-4-benzoyloxy-5-ethyl-1,2-dihydro-1-methyl-2-oxo-quinoline-3-carboxamide ¹H NMR: 1.21 (t, 3H), 2.92 (q, 2H), 3.69 (s, 3H), 7.09 (d, 1H), 7.20-7.33 (m, 7H), 7.38 (tt, 1H), 7.49-7.58 (m, 3H), 7.68 (tt, 1H), 7.79 (broad d, 2H), 8.20 (d, 2H).

Example 137

N-acetyl-N-(4-methoxyphenyl)-4-acetoxy-6,7-dihydro-3,7-dimethyl-6-oxo-thieno[2,3-b]pyridine-5-carboxamide $^1$H NMR: 2.15 (s, 3H), 2.33 (s, 3H), 2.36 (d, 3H), 3.62 (s, 3H), 3.83 (s, 3H), 6.59 (d, 1H), 6.95 (d, 2H), 7.28 (d, 2H).

Example 138

N-iso-butyryl-N-(4-trifluoromethylphenyl)-4-iso-butyryloxy-1,2-dihydro-1-methyl-2-oxo-quinoline-3-carboxamide $^1$H NMR: 1.13 (d, 6H), 1.38 (d, 6H), 2.71 (m, 1H), 2.93 (m, 1H), 3.69 (s, 3H), 7.28 (ddd, 1H), 7.39 (d, 1H), 7.53 (d, 2H), 7.59-7.67 (m, 2H), 7.73 (d, 2H).

Example 139

N-iso-butyryl-N-(4-chlorophenyl)-4-iso-butyryloxy-5-chloro-1,2-dihydro-1-methyl-2-oxo-quinoline-3-carboxamide $^1$H NMR: 1.13 (d, 6H), 1.31 (d, 6H), 2.85 (broad m, 1H), 2.88 (m, 1H), 3.69 (s, 3H), 7.26-7.36 (m, 4H), 7.43 (d, 2H), 7.48 (dd, 1H).

Example 140

N-benzoyl-N-(4-chlorophenyl)-4-benzoyloxy-5-chloro-1,2-dihydro-1-methyl-2-oxo-quinoline-3-carboxamide $^1$H NMR: 3.71 (s, 3H), 7.15-7.40 (m, 9H), 7.48-7.57 (m, 3H), 7.67 (tt, 1H), 7.71 (broad d, 2H), 8.21 (d, 1H).

Example 141

N-benzoyl-N-(4-methoxyphenyl)-4-benzoyloxy-5-chloro-1,2-dihydro-1-methyl-2-oxo-quinoline-3-carboxamide $^1$H NMR: 3.68 (s, 3H), 3.71 (s, 3H), 6.77 (d, 2H), 7.17 (broad d, 2H), 7.21-7.41 (m, 5H), 7.44-7.56 (m, 3H), 7.66 (tt, 1H), 7.74 (broad d, 2H), 8.21 (d, 1H).

Example 142

N-acetyl-N-(4-chlorophenyl)-4-acetoxy-1,2-dihydro-6-methoxy-1-methyl-2-oxo-quinoline-3-carboxamide $^1$H NMR: 2.18 (s, 3H), 2.41 (s, 3H), 3.67 (s, 3H), 3.87 (s, 3H), 7.03 (d, 1H), 7.26 (dd, 1H), 7.31-7.36 (m, 3H), 7.42 (d, 2H).

Example 143

N-acetyl-N-(4-chlorophenyl)-4-acetoxy-1,2-dihydro-5-methoxy-1-methyl-2-oxo-quinoline-3-carboxamide $^1$H NMR: 2.32 (s, 3H), 2.33 (s, 3H), 3.63 (s, 3H), 3.89 (s, 3H), 6.71 (d, 1H), 6.97 (d, 1H), 7.30 (d, 2H), 7.37 (d, 2H), 7.52 (t, 1H).

Example 144

N-iso-butyryl-N-(4-chlorophenyl)-4-iso-butyryloxy-1,2-dihydro-5-methoxy-1-methyl-2-oxo-quinoline-3-carboxamide $^1$H NMR: 1.17 (d, 6H), 1.33 (d, 6H), 2.85 (m, 1H), 3.05 (broad m, 1H), 3.63 (s, 3H), 3.86 (s, 3H), 6.69 (d, 1H), 6.97 (d, 1H), 7.29 (d, 2H), 7.37 (d, 2H), 7.50 (t, 1H).

Example 145

N-benzoyl-N-(4-chlorophenyl)-4-benzoyloxy-1,2-dihydro-5-methoxy-1-methyl-2-oxo-quinoline-3-carboxamide $^1$H NMR: 3.50 (s, 3H), 3.65 (s, 3H), 6.64 (d, 1H), 6.97 (d, 1H), 7.20-7.34 (m, 6H), 7.40 (tt, 1H), 7.48-7.59 (m, 3H), 7.67 (tt, 1H), 7.82 (broad d, 2H), 8.20 (d, 2H).

Example 146

N-acetyl-N-(4-methoxyphenyl)-4-acetoxy-1,2-dihydro-5-methoxy-1-methyl-2-oxo-quinoline-5-carboxamide $^1$H NMR: 2.28 (s, 3H), 2.33 (s, 3H), 3.64 (s, 3H), 3.80 (s, 3H), 3.89 (s, 3H), 6.70 (d, 1H), 6.91 (d, 2H), 6.97 (d, 1H), 7.27 (broad d, 2H), 7.51 (t, 1H).

Example 147

N-iso-butyryl-N-(4-methoxyphenyl)-4-iso-butyryloxy-1,2-dihydro-5-methoxy-1-methyl-2-oxo-quinoline-3-carboxamide $^1$H NMR: 1.14 (d, 6H), 1.33 (d, 6H), 2.85 (m, 1H), 3.01 (broad m, 1H), 3.64 (s, 3H), 3.81 (s, 3H), 3.85 (s, 3H), 6.68 (d, 1H), 6.91 (d, 2H), 6.97 (d, 1H), 7.27 (d, 2H), 7.48 (t, 1H).

Example 148

N-benzoyl-N-(4-methoxyphenyl)-4-benzoyloxy-1,2-dihydro-5-methoxy-1-methyl-2-oxo-quinoline-3-carboxamide $^1$H NMR: 3.49 (s, 3H), 3.64 (s, 3H), 3.72 (s, 3H), 6.63 (d, 1H), 6.79 (d, 2H), 6.95 (d, 1H), 7.19-7.32 (m, 4H), 7.37 (t, 1H), 7.48 (t, 1H), 7.54 (t, 2H), 7.66 (tt, 1H), 7.83 (broad d, 2H), 8.21 (d, 2H).

Example 149

N-acetyl-N-(4-fluorophenyl)-4-acetoxy-5-ethyl-1,2-dihydro-1-methyl-2-oxo-quinoline-3-carboxamide $^1$H NMR: 1.29 (t, 3H), 2.21 (s, 3H), 2.35 (s, 3H), 2.99 (q, 2H), 3.70 (s, 3H), 7.07-7.15 (m, 3H), 7.29 (d, 1H), 7.37 (m, 2H), 7.53 (dd, 1H).

Example 150

N-iso-butyryl-N-(4-fluorophenyl)-4-iso-butyryloxy-5-ethyl-1,2-dihydro-1-methyl-2-oxo-quinoline-3-carboxamide $^1$H NMR: 1.14 (d, 6H), 1.26 (t, 3H), 1.33 (d, 6H), 2.84 (m, 1H), 2.94 (broad m, 1H), 2.97 (q, 2H), 3.68 (s, 3H), 7.06-7.14 (m, 3H), 7.28 (d, 1H), 7.36 (m, 2H), 7.50 (dd, 1H).

Example 151

N-benzoyl-N-(4-fluorophenyl)-4-benzoyloxy-5-ethyl-1,2-dihydro-1-methyl-2-oxo-quinoline-3-carboxamide $^1$H NMR: 1.21 (t, 3H), 2.92 (q, 2H), 3.70 (s, 3H), 6.95 (t, 2H), 7.09 (d, 1H), 7.24-7.33 (m, 5H), 7.37 (tt, 1H), 7.50-7.58 (m, 3H), 7.69 (tt, 1H), 7.80 (broad d, 2H), 8.20 (d, 2H).

Example 152

N-acetyl-N-(4-trifluoromethylphenyl)-4-acetoxy-5-ethyl-1,2-dihydro-1-methyl-2-oxo-quinoline-3-carboxamide $^1$H NMR: 1.29 (t, 3H), 2.17 (s, 3H), 2.35 (s, 3H), 3.00 (q, 2H), 3.69 (s, 3H), 7.12 (d, 1H), 7.29 (d, 1H), 7.49-7.57 (m, 3H), 7.72 (d, 2H).

Example 153

N-iso-butyryl-N-(4-trifluoromethylphenyl)-4-iso-butyryloxy-5-ethyl-1,2-dihydro-1-methyl-2-oxo-quinoline-3-carboxamide $^1$H NMR: 1.14 (d, 6H), 1.27 (t, 3H), 1.32 (d, 6H), 2.79 (broad m, 1H), 2.84 (m, 1H), 2.99 (q, 2H), 3.69 (s, 3H), 7.10 (d, 1H), 7.29 (d, 1H), 7.47-7.56 (m, 3H), 7.71 (d, 2H).

Example 154

N-benzoyl-N-(4-trifluoromethylphenyl)-4-benzoyloxy-5-ethyl-1,2-dihydro-1-methyl-2-oxo-quinoline-3-carboxamide $^1$H NMR: 1.22 (t, 3H), 2.93 (broad q, 2H), 3.69 (s, 3H), 7.11 (d, 1H), 7.25-7.43 (m, 6H), 7.50-7.58 (m, 5H), 7.68 (t, 1H), 7.77 (broad d, 2H), 8.21 (d, 2H).

Example 155

N-acetyl-N-(4-methoxyphenyl)-4-acetoxy-5-ethyl-1,2-dihydro-1-methyl-2-oxo-quinoline-3-carboxamide $^1$H NMR: 1.28 (t, 3H), 2.20 (s, 3H), 2.35 (s, 3H), 2.99 (q, 2H), 3.70 (s, 3H), 3.81 (s, 3H), 6.93 (d, 2H), 7.10 (d, 1H), 7.26-7.35 (m, 3H), 7.51 (dd, 2H).

Example 156

N-iso-butyryl-N-(4-methoxyphenyl)-4-iso-butyryloxy-5-ethyl-1,2-dihydro-1-methyl-2-oxo-quinoline-3-carboxamide $^1$H NMR: 1.13 (d, 6H), 1.26 (t, 3H), 1.33 (d, 6H), 2.84 (m, 1H), 2.89-3.03 (m, 3H), 3.69 (s, 3H), 3.81 (s, 3H), 6.92 (d, 2H), 7.08 (d, 1H), 7.25-7.32 (m, 3H), 7.49 (dd, 1H).

Example 157

N-benzoyl-N-(4-methoxyphenyl)-4-benzoyloxy-5-ethyl-1,2-dihydro-1-methyl-2-oxo-quinoline-3-carboxamide $^1$H NMR: 1.20 (t, 3H), 2.91 (broad q, 2H), 3.69 (s, 3H), 3.71 (s, 3H), 6.77 (d, 2H), 7.07 (d, 1H), 7.18-7.32 (m, 5H), 7.47-7.58 (m, 3H), 7.68 (tt, 1H), 7.83 (broad d, 2H), 8.21 (d, 2H).

Example 158

N-acetyl-N-(4-fluorophenyl)-4-acetoxy-5-chloro-1,2-dihydro-1-methyl-2-oxo-quinoline-3-carboxamide $^1$H NMR: 2.20 (s, 3H), 2.36 (s, 3H), 3.69 (s, 3H), 7.14 (t, 2H), 7.30 (dd, 1H), 7.32-7.40 (m, 3H), 7.50 (dd, 1H).

Example 159

N-iso-butyryl-N-(4-fluorophenyl)-4-iso-butyryloxy-5-chloro-1,2-dihydro-1-methyl-2-oxo-quinoline-3-carboxamide $^1$H NMR: 1.13 (d, 6H), 1.31 (d, 6H), 2.87 (broad m, 1H), 2.88 (m, 1H), 3.68 (s, 3H), 7.13 (t, 2H), 7.27 (dd, 1H), 7.30-7.39 (m, 3H), 7.44 (dd, 2H).

Example 160

N-benzoyl-N-(4-fluorophenyl)-4-benzoyloxy-5-chloro-1,2-dihydro-1-methyl-2-oxo-quinoline-3-carboxamide $^1$H NMR: 3.70 (s, 3H), 6.96 (t, 2H), 7.19-7.42 (m, 7H), 7.46-7.57 (m, 3H), 7.67 (tt, 1H), 7.72 (broad d, 2H), 8.21 (d, 1H).

Example 161

N-acetyl-N-(4-trifluoromethylphenyl)-4-acetoxy-5-chloro-1,2-dihydro-1-methyl-2-oxo-quinoline-3-carboxamide $^1$H NMR: 2.17 (s, 3H), 2.36 (s, 3H), 3.69 (s, 3H), 7.31 (dd, 1H), 7.35 (dd, 1H), 7.47-7.55 (m, 3H), 7.74 (d, 2H).

Example 162

N-iso-butyryl-N-(4-trifluoromethylphenyl)-4-iso-butyryloxy-5-chloro-1,2-dihydro-1-methyl-2-oxo-quinoline-3-carboxamide $^1$H NMR: 1.13 (d, 6H), 1.31 (d, 6H), 2.75 (broad m, 1H), 2.88 (m, 1H), 3.70 (s, 3H), 7.29 (dd, 1H), 7.34 (dd, 1H), 7.49 (dd, 1H), 7.51 (d, 2H), 7.74 (d, 2H).

Example 163

N-benzoyl-N-(4-trifluoromethylphenyl)-4-benzoyloxy-5-chloro-1,2-dihydro-1-methyl-2-oxo-quinoline-3-carboxamide $^1$H NMR: 3.70 (s, 3H), 7.24-7.42 (m, 7H), 7.48-7.57 (m, 5H), 7.67 (tt, 1H), 7.70 (broad d, 2H), 8.21 (d, 1H).

Examples 164-208

A library of 4-O-mono-acylated compounds (4-acyloxy-1,2-dihydro-1-methyl-2-oxo-quinoline-3-carboxanilides and 4-acyloxy-6,7-dihydro-7-methyl-6-oxo-thieno[2,3-b]pyridine-5-carboxanilides) was prepared by basic cleavage of the corresponding di-acylated starting materials according to the following general procedure:

A solution of NaOH in MeOH (0.10 mL, 0.020 mmol, 0.20 M) was added to a solution of the di-acylated starting material (0.020 mmol) in THF (0.2 mL) and MeOH (0.2 mL). The

Example 164

N-phenyl-4-acetoxy-1,2-dihydro-5-methoxy-1-methyl-2-oxo-quinoline-3-carboxamide $^1$H NMR: 2.46 (s, 3H), 3.80 (s, 3H), 3.95 (s, 3H), 6.79 (d, 1H), 7.07 (d, 1H), 7.11 (tt, 1H), 7.35 (t, 2H), 7.62 (t, 1H), 7.69 (d, 2H), 11.20 (s, 1H).

Example 165

N-phenyl-4-benzoyloxy-1,2-dihydro-5-methoxy-1-methyl-2-oxo-quinoline-3-carboxamide $^1$H NMR: 3.58 (s, 3H), 3.83 (s, 3H), 6.73 (d, 1H), 7.06 (tt, 1H), 7.08 (d, 1H), 7.28 (t, 2H), 7.54 (t, 2H), 7.58-7.70 (m, 4H), 8.27 (d, 2H), 10.87 (s, 1H).

Example 166

N-(4-trifluoromethylphenyl)-4-acetoxy-1,2-dihydro-5-methoxy-1-methyl-2-oxo-quinoline-3-carboxamide $^1$H NMR: 2.47 (s, 3H), 3.80 (s, 3H), 3.97 (s, 3H), 6.80 (d, 1H), 7.08 (d, 1H), 7.59 (d, 2H), 7.65 (t, 1H), 7.82 (d, 2H), 11.74 (s, 1H).

Example 167

N-(4-trifluoromethylphenyl)-4-iso-butyryloxy-1,2-dihydro-5-methoxy-1-methyl-2-oxo-quinoline-3-carboxamide $^1$H NMR: 1.41 (d, 6H), 3.03 (m, 1H), 3.75 (s, 3H), 3.93 (s, 3H), 6.80 (d, 1H), 7.05 (d, 1H), 7.56 (d, 2H), 7.63 (t, 1H), 7.79 (d, 2H), 11.31 (s, 1H).

Example 168

N-(4-trifluoromethylphenyl)-4-benzoyloxy-1,2-dihydro-5-methoxy-1-methyl-2-oxo-quinoline-3-carboxamide $^1$H NMR: 3.59 (s, 3H), 3.82 (s, 3H), 6.75 (d, 1H), 7.09 (d, 1H), 7.51 (d, 2H), 7.56 (t, 2H), 7.64 (t, 1H), 7.68 (tt, 1H), 7.75 (d, 2H), 8.27 (d, 2H), 11.49 (s, 1H).

Example 169

N-(4-fluorophenyl)-4-acetoxy-1,2-dihydro-5-methoxy-1-methyl-2-oxo-quinoline-3-carboxamide $^1$H NMR: 2.45 (s, 3H), 3.79 (s, 3H), 3.95 (s, 3H), 6.79 (d, 1H), 7.03 (t, 2H), 7.07 (d, 1H), 7.62 (t, 1H), 7.65 (m, 2H), 11.33 (s, 1H).

Example 170

N-(4-fluorophenyl)-4-iso-butyryloxy-1,2-dihydro-5-methoxy-1-methyl-2-oxo-quinoline-3-carboxamide $^1$H NMR: 1.40 (d, 6H), 3.02 (m, 1H), 3.77 (s, 3H), 3.92 (s, 3H), 6.78 (d, 1H), 7.02 (t, 2H), 7.05 (d, 1H), 7.61 (t, 1H), 7.64 (m, 2H), 10.85 (s, 1H).

Example 171

N-phenyl-4-acetoxy-5-ethyl-1,2-dihydro-1-methyl-2-oxo-quinoline-3-carboxamide $^1$H NMR: 1.35 (t, 3H), 2.54 (s, 3H), 3.16 (q, 2H), 3.85 (s, 3H), 7.12 (tt, 1H), 7.19 (d, 1H), 7.36 (t, 2H), 7.38 (d, 1H), 7.62 (dd, 1H), 7.69 (d, 2H), 11.75 (s, 1H).

Example 172

N-phenyl-4-iso-butyryloxy-5-ethyl-1,2-dihydro-1-methyl-2-oxo-quinoline-3-carboxamide $^1$H NMR: 1.32 (t, 3H), 1.44 (d, 6H), 3.08 (m, 1H), 3.16 (q, 2H), 3.84 (s, 3H), 7.11 (tt, 1H), 7.19 (d, 1H), 7.35 (t, 2H), 7.38 (d, 1H), 7.61 (dd, 1H), 7.68 (d, 2H), 11.26 (s, 1H).

Example 173

N-phenyl-4-benzoyloxy-5-ethyl-1,2-dihydro-1-methyl-2-oxo-quinoline-3-carboxamide $^1$H NMR: 1.20 (t, 3H), 3.08 (broad m, 2H), 3.88 (s, 3H), 7.05 (tt, 1H), 7.18 (d, 1H), 7.27 (t, 2H), 7.42 (d, 1H), 7.53-7.67 (m, 5H), 7.71 (tt, 1H), 8.30 (d, 2H), 11.51 (s, 1H).

Example 174

N-(4-chlorophenyl)-4-acetoxy-5-ethyl-1,2-dihydro-1-methyl-2-oxo-quinoline-3-carboxamide $^1$H NMR: 1.34 (t, 3H), 2.53 (s, 3H), 3.16 (q, 2H), 3.84 (s, 3H), 7.21 (d, 1H), 7.31 (d, 2H), 7.39 (d, 1H), 7.63 (dd, 1H), 7.65 (d, 2H), 11.94 (s, 1H).

Example 175

N-(4-chlorophenyl)-4-iso-butyryloxy-5-ethyl-1,2-dihydro-1-methyl-2-oxo-quinoline-3-carboxamide $^1$H NMR: 1.32 (t, 3H), 1.44 (d, 6H), 3.07 (m, 1H), 3.17 (q, 2H), 3.84 (s, 3H), 7.20 (d, 1H), 7.30 (d, 2H), 7.38 (d, 1H), 7.59-7.67 (m, 3H), 11.50 (s, 1H).

Example 176

N-phenyl-4-acetoxy-6,7-dihydro-3,7-dimethyl-6-oxo-thieno[2,3-b]pyridine-5-carboxamide $^1$H NMR: 2.46 (d, 3H), 2.51 (s, 3H), 3.77 (s, 3H), 6.77 (q, 1H), 7.10 (tt, 1H), 7.34 (t, 2H), 7.69 (d, 2H), 11.87 (s, 1H).

Example 177

N-phenyl-4-iso-butyryloxy-6,7-dihydro-3,7-dimethyl-6-oxo-thieno[2,3-b]pyridine-5-carboxamide $^1$H NMR: 1.43 (d, 6H), 2.45 (d, 3H), 3.12 (m, 1H), 3.77 (s, 3H), 6.65 (q, 1H), 7.09 (tt, 1H), 7.33 (t, 2H), 7.69 (d, 2H), 11.73 (s, 1H).

Example 178

N-(4-fluorophenyl)-4-benzoyloxy-6,7-dihydro-3,7-dimethyl-6-oxo-thieno[2,3-b]pyridine-5-carboxamide $^1$H NMR: 2.37 (d, 3H), 3.81 (s, 3H), 6.67 (q, 1H), 6.95 (t, 2H), 7.52-7.60 (m, 4H), 7.70 (tt, 1H), 8.28 (d, 2H), 11.84 (s, 1H).

Example 179

N-phenyl-4-iso-butyryloxy-1,2-dihydro-1-methyl-2-oxo-quinoline-3-carboxamide $^1$H NMR: 1.49 (d, 6H), 3.18 (m, 1H), 3.84 (s, 3H), 7.11 (tt, 1H), 7.31-7.41 (m, 3H), 7.48 (d, 1H), 7.70 (d, 2H), 7.75 (ddd, 1H), 7.90 (dd, 1H), 11.67 (s, 1H).

Example 180

N-phenyl-4-benzoyloxy-1,2-dihydro-1-methyl-2-oxo-quinoline-3-carboxamide $^1$H NMR: 3.88 (s, 3H), 7.07 (tt, 1H), 7.29 (t, 2H), 7.35 (t, 1H), 7.52 (d, 1H), 7.59 (t, 2H), 7.64 (d, 2H), 7.72 (tt, 1H), 7.76 (tt, 1H), 7.97 (dd, 1H), 8.34 (d, 2H), 11.73 (s, 1H).

Example 181

N-(4-methoxyphenyl)-4-acetoxy-1,2-dihydro-1-methyl-2-oxo-quinoline-3-carboxamide $^1$H NMR: 2.57 (s, 3H), 3.82 (s, 3H), 3.84 (s, 3H), 6.90 (d, 2H), 7.38 (t, 1H), 7.48 (d, 1H), 7.61 (d, 2H), 7.75 (ddd, 1H), 7.95 (dd, 1H), 11.72 (s, 1H).

Example 182

N-(4-trifluoromethylphenyl)-4-acetoxy-1,2-dihydro-1-methyl-2-oxo-quinoline-3-carboxamide $^1$H NMR: 2.59 (s, 3H), 3.85 (s, 3H), 7.41 (t, 1H), 7.50 (d, 1H), 7.60 (d, 2H), 7.78 (ddd, 1H), 7.83 (d, 2H), 7.97 (dd, 1H), 12.23 (s, 1H).

Example 183

N-(4-trifluoromethylphenyl)-4-iso-butyryloxy-1,2-dihydro-1-methyl-2-oxo-quinoline-3-carboxamide $^1$H NMR: 1.50 (d, 6H), 3.18 (m, 1H), 3.85 (s, 3H), 7.39 (tt, 1H), 7.50 (d, 1H), 7.60 (d, 2H), 7.77 (ddd, 1H), 7.82 (d, 2H), 7.91 (dd, 1H), 12.08 (s, 1H).

Example 184

N-phenyl-4-acetoxy-5-chloro-1,2-dihydro-1-methyl-2-oxo-quinoline-3-carboxamide $^1$H NMR: 2.52 (s, 3H), 3.84 (s, 3H), 7.13 (tt, 1H), 7.32-7.45 (m, 4H), 7.59 (dd, 1H), 7.68 (d, 2H), 11.16 (s, 1H).

Example 185

N-phenyl-4-iso-butyryloxy-5-chloro-1,2-dihydro-1-methyl-2-oxo-quinoline-3-carboxamide $^1$H NMR: 1.40 (d, 6H), 3.06 (m, 1H), 3.82 (s, 3H), 7.12 (tt, 1H), 7.35 (t, 2H), 7.38 (dd, 1H), 7.41 (dd, 1H), 7.57 (dd, 1H), 7.66 (d, 2H), 10.43 (s, 1H).

Example 186

N-phenyl-4-benzoyloxy-5-chloro-1,2-dihydro-1-methyl-2-oxo-quinoline-3-carboxamide $^1$H NMR: 3.87 (s, 3H), 7.07 (tt, 1H), 7.27 (t, 2H), 7.38 (dd, 1H), 7.45 (dd, 1H), 7.52-7.62 (m, 5H), 7.68 (tt, 1H), 8.29 (d, 2H), 10.80 (s, 1H).

Example 187

N-(4-chlorophenyl)-4-acetoxy-5-chloro-1,2-dihydro-1-methyl-2-oxo-quinoline-3-carboxamide $^1$H NMR: 2.52 (s, 3H), 3.83 (s, 3H), 7.31 (d, 2H), 7.41 (dd, 1H), 7.44 (dd, 1H), 7.60 (dd, 1H), 7.64 (d, 2H), 11.41 (s, 1H).

Example 188

N-(4-methoxyphenyl)-4-acetoxy-5-chloro-1,2-dihydro-1-methyl-2-oxo-quinoline-3-carboxamide $^1$H NMR: 2.51 (s, 3H), 3.82 (s, 3H), 3.83 (s, 3H), 6.90 (d, 2H), 7.38-7.45 (m, 2H), 7.55-7.62 (m, 3H), 11.03 (s, 1H).

Example 189

N-(4-methoxyphenyl)-4-iso-butyryloxy-5-chloro-1,2-dihydro-1-methyl-2-oxo-quinoline-3-carboxamide $^1$H NMR: 1.39 (d, 6H), 3.05 (m, 1H), 3.81 (s, 3H), 3.81 (s, 3H), 6.88 (d, 2H), 7.37 (dd, 1H), 7.40 (dd, 1H), 7.53-7.61 (m, 3H), 10.27 (s, 1H).

Example 190

N-phenyl-4-acetoxy-1,2-dihydro-6-methoxy-1-methyl-2-oxo-quinoline-3-carboxamide $^1$H NMR: 2.59 (s, 3H), 3.83 (s, 3H), 3.91 (s, 3H), 7.12 (tt, 1H), 7.30 (d, 1H), 7.32-7.39 (m, 3H), 7.43 (d, 1H), 7.71 (d, 2H), 12.00 (s, 1H).

Example 191

N-phenyl-4-iso-butyryloxy-1,2-dihydro-6-methoxy-1-methyl-2-oxo-quinoline-3-carboxamide $^1$H NMR: 1.49 (d, 6H), 3.19 (m, 1H), 3.83 (s, 3H), 3.89 (s, 3H), 7.11 (tt, 1H), 7.26 (d, 1H), 7.35 (t, 2H), 7.35 (dd, 1H), 7.42 (d, 1H), 7.70 (d, 2H), 11.83 (s, 1H).

Example 192

N-(4-fluorophenyl)-4-acetoxy-1,2-dihydro-6-methoxy-1-methyl-2-oxo-quinoline-3-carboxamide $^1$H NMR: 2.58 (s, 3H), 3.83 (s, 3H), 3.92 (s, 3H), 7.04 (t, 2H), 7.30 (d, 1H), 7.38 (dd, 1H), 7.44 (dd, 1H), 7.67 (m, 2H), 12.05 (s, 1H).

Example 193

N-(4-chlorophenyl)-4-acetoxy-1,2-dihydro-6-methoxy-1-methyl-2-oxo-quinoline-3-carboxamide $^1$H NMR: 2.58 (s, 3H), 3.83 (s, 3H), 3.92 (s, 3H), 7.30 (d, 1H), 7.31 (d, 2H), 7.38 (dd, 1H), 7.44 (d, 1H), 7.66 (d, 2H), 12.15 (s, 1H).

Example 194

N-(4-chlorophenyl)-4-benzoyloxy-1,2-dihydro-6-methoxy-1-methyl-2-oxo-quinoline-3-carboxamide $^1$H NMR: 3.82 (s, 3H), 3.86 (s, 3H), 7.23 (d, 2H), 7.32 (d, 1H), 7.38 (dd, 1H), 7.47 (d, 1H), 7.59 (d, 2H), 7.60 (t, 2H), 7.73 (tt, 1H), 8.33 (d, 2H), 12.04 (s, 1H).

Example 195

N-phenyl-4-acetoxy-6-chloro-1,2-dihydro-1-methyl-2-oxo-quinoline-3-carboxamide $^1$H NMR: 2.59 (s, 3H), 3.82 (s, 3H), 7.13 (tt, 1H), 7.36 (t, 2H), 7.43 (d, 1H), 7.66-7.72 (m, 3H), 7.89 (d, 1H), 11.73 (s, 1H).

Example 196

N-(4-fluorophenyl)-4-iso-butyryloxy-6-chloro-1,2-dihydro-1-methyl-2-oxo-quinoline-3-carboxamide $^1$H NMR: 1.49 (d, 6H), 3.16 (m, 1H), 3.82 (s, 3H), 7.04 (t, 2H), 7.43 (d, 1H), 7.65 (m, 2H), 7.69 (dd, 1H), 7.83 (d, 1H), 11.60 (s, 1H).

Example 197

N-(4-chlorophenyl)-4-benzoyloxy-6-chloro-1,2-dihydro-1-methyl-2-oxo-quinoline-3-carboxamide $^1$H NMR: 3.85 (s, 3H), 7.24 (d, 2H), 7.46 (d, 1H), 7.57 (d, 2H), 7.61 (t, 2H), 7.70 (dd, 1H), 7.74 (tt, 1H), 7.91 (d, 1H), 8.32 (d, 2H), 11.78 (s, 1H).

Example 198

N-(4-chlorophenyl)-4-acetoxy-1,2-dihydro-5-methoxy-1-methyl-2-oxo-quinoline-3-carboxamide $^1$H NMR: 2.46 (s, 3H), 3.80 (s, 3H), 3.96 (s, 3H), 6.80 (d, 1H), 7.08 (d, 1H), 7.30 (d, 2H), 7.62 (t, 1H), 7.66 (d, 2H), 11.48 (s, 1H).

Example 199

N-(4-methoxyphenyl)-4-benzoyloxy-1,2-dihydro-5-methoxy-1-methyl-2-oxo-quinoline-3-carboxamide $^1$H NMR: 3.57 (s, 3H), 3.77 (s, 3H), 3.82 (s, 3H), 6.72 (d, 1H), 6.82 (d, 2H), 7.08 (d, 1H), 7.50-7.69 (m, 6H), 8.26 (d, 2H), 10.69 (s, 1H).

Example 200

N-(4-fluorophenyl)-4-benzoyloxy-5-ethyl-1,2-dihydro-1-methyl-2-oxo-quinoline-3-carboxamide $^1$H NMR: 1.20 (t, 3H), 3.08 (broad m, 2H), 3.88 (s, 3H), 6.95 (t, 2H), 7.19 (d, 1H), 7.42 (d, 1H), 7.54 (m, 2H), 7.58 (t, 2H), 7.63 (dd, 1H), 7.71 (tt, 1H), 8.29 (d, 2H), 11.62 (s, 1H).

Example 201

N-(4-trifluoromethylphenyl)-4-acetoxy-5-ethyl-1,2-dihydro-1-methyl-2-oxo-quinoline-3-carboxamide $^1$H NMR: 1.35 (t, 3H), 2.55 (s, 3H), 3.17 (q, 2H), 3.86 (s, 3H), 7.22 (d, 1H), 7.40 (d, 1H), 7.60 (d, 2H), 7.65 (dd, 1H), 7.82 (d, 2H), 12.18 (s, 1H).

Example 202

N-(4-trifluoromethylphenyl)-4-iso-butyryloxy-5-ethyl-1,2-dihydro-1-methyl-2-oxo-quinoline-3-carboxamide $^1$H NMR: 1.33 (t, 3H), 1.45 (d, 6H), 3.08 (m, 1H), 3.17 (q, 2H), 3.83 (s, 3H), 7.21 (d, 1H), 7.38 (d, 1H), 7.59 (d, 2H), 7.63 (dd, 1H), 7.80 (d, 2H), 11.77 (s, 1H).

Example 203

N-(4-methoxyphenyl)-4-iso-butyryloxy-5-ethyl-1,2-dihydro-1-methyl-2-oxo-quinoline-3-carboxamide $^1$H NMR: 1.32 (t, 3H), 1.43 (d, 6H), 3.07 (m, 1H), 3.16 (q, 2H), 3.81 (s, 3H), 3.83 (s, 3H), 6.89 (d, 2H), 7.18 (d, 1H), 7.37 (d, 1H), 7.60 (d, 2H), 7.60 (t, 1H), 11.11 (s, 1H).

Example 204

N-(4-fluorophenyl)-4-acetoxy-5-chloro-1,2-dihydro-1-methyl-2-oxo-quinoline-3-carboxamide $^1$H NMR: 2.51 (s, 3H), 3.83 (s, 3H), 7.05 (t, 2H), 7.41 (dd, 1H), 7.43 (dd, 1H), 7.59 (dd, 1H), 7.64 (m, 2H), 11.29 (s, 1H).

Example 205

N-(4-fluorophenyl)-4-iso-butyryloxy-5-chloro-1,2-dihydro-1-methyl-2-oxo-quinoline-3-carboxamide $^1$H NMR: 1.40 (d, 6H), 3.05 (m, 1H), 3.80 (s, 3H), 7.03 (t, 2H), 7.38 (dd, 1H), 7.41 (dd, 1H), 7.58 (dd, 1H), 7.63 (m, 2H), 11.61 (s, 1H).

Example 206

N-(4-fluorophenyl)-4-benzoyloxy-5-chloro-1,2-dihydro-1-methyl-2-oxo-quinoline-3-carboxamide $^1$H NMR: 3.86 (s, 3H), 6.96 (t, 2H), 7.38 (dd, 1H), 7.46 (dd, 1H), 7.50-7.59 (m, 4H), 7.60 (dd, 1H), 7.68 (tt, 1H), 8.29 (d, 2H), 10.97 (s, 1H).

Example 207

N-(4-trifluoromethylphenyl)-4-acetoxy-5-chloro-1,2-dihydro-1-methyl-2-oxo-quinoline-3-carboxamide $^1$H NMR: 2.53 (s, 3H), 3.84 (s, 3H), 7.42 (dd, 1H), 7.45 (dd, 1H), 7.60 (d, 2H), 7.61 (dd, 1H), 7.81 (d, 2H), 11.67 (s, 1H).

Example 208

N-(4-trifluoromethylphenyl)-4-benzoyloxy-5-chloro-1,2-dihydro-1-methyl-2-oxo-quinoline-3-carboxamide $^1$H NMR: 3.87 (s, 3H), 7.40 (dd, 1H), 7.46 (dd, 1H), 7.52 (d, 2H), 7.57 (t, 2H), 7.62 (dd, 1H), 7.66-7.74 (m, 3H), 8.29 (d, 2H), 11.41 (s, 1H).

Example 209

Solubility Measurements

Solubilities of a di- and a mono-acylated compound were measured in 0.2 M phosphate buffer pH 7.4 and compared with the solubility of the corresponding non-acylated compound.

Saturated compound solutions were prepared by mixing the compounds and the buffer solution at ambient temperature for 24 h followed by separation of the aqueous solution by centrifugation. Standard solutions of compounds (1.00 mg/mL) were prepared in DMSO.

The compound concentrations were measured by HPLC-MS/UV (Waters Alliance 2790 Separations Module/996 PDA detector/Micromass Quattro Micro) after appropriate dilutions of the aqueous saturated solutions (1/10 and 1/100) and the standard solutions (1/100, 1/200, and 1/1000), respectively, with mobile phase solvent.

The following compounds were tested:
Compound 1
N-acetyl-N-phenyl-4-acetoxy-1,2-dihydro-1-methyl-2-oxo-quinoline-3-carboxamide (Example 30)
Compound 2
N-phenyl-4-acetoxy-1,2-dihydro-1-methyl-2-oxo-quinoline-3-carboxamide (Example 31)
Compound 3
N-phenyl-1,2-dihydro-4-hydroxy-1-methyl-2-oxo-quinoline-3-carboxamide (N-hydrogen amide derivative of Roquinimex)

Results (from two dilutions):
Compound 1: 21 and 38 mg/L
Compound 2: 186 and 221 mg/L
Compound 3: <1 mg/L The results show that acylation of N-hydrogen-4-hydroxycarboxanilides to give acylated prodrugs can enhance the aqueous solubility considerably.

Example 210

Activation of the Aryl-Hydrocarbon Receptor

Activation of the aryl hydrocarbon receptor can be measured in cell-based reporter-gene assays, which consist of cell lines containing the aryl hydrocarbon recptor and transfected with a reporter gene regulated by activated Ahr via an XRE (xenobiotic response element). AhR activation will thus result in an enhanced expression of the reporter protein (e.g. luciferase) which functional activity can be measured.

Commercial reporter-gene assays for this purpose are e.g. the GeneBLAzer® CYP1A1-bla LS-180 cell line (Invitrogen) which involves an XRE of a CYP1A1 promotor and a beta-lactamase reporter gene, the XDS-CALUXR® assay (Xenobiotic Detection Systems) developed in a mouse hepatoma cell-line using the luciferase reporter gene, and the Cignal XRE Reporter (SABiosciences) also with a luciferase reporter gene. Such reporter-gene assays can also be constructed by a person skilled in the art.

Activation of human AhR was measured in the Gene-BLAzer® CYP1A1-bla LS-180 cell line (Invitrogen Corporation, Madison, www.invitrogen.com/drugdiscovery) using a beta-lactamase reporter gene (bla) combined with a FRET-enabled substrate sensitive to bla expression.

CYP1A1-bla LS-180 cells are harvested and suspended in Assay Media (OPTI-MEM, 0.5% dialyzed FBS, 0.1 mM NEAA, 1 mM Sodium Pyruvate, 100 U/mL/100 µg/mL Pen/Strep) to a concentration of 625,000 cells/mL. 32 µL of cell suspension (20,000 cells) is added to each well of a 384-well Poly-D-Lysine assay plate. Cells in assay media are incubated for 16-24 hours in the plate at 37° C./5% $CO_2$ in a humidified incubator. 4 µL of a 10× serial dilution of beta-naphthoflavone (control activator starting concentration, 100,000 nM) or compounds are added to appropriate wells. 4 µL of Assay Media is added to all wells to bring the final assay volume to 40 µL. The plate is incubated for 16 hours at 37° C./5% $CO_2$ in a humidified incubator. 8 µL of 1 µM Substrate solution is added to each well and the plate is incubated for 1.5 hours at room temperature. The plate is read on a fluorescence plate reader.

Test Compounds

The compounds tested in duplicates are serially diluted in 100% DMSO to 1000× test concentrations. An aliquot of the serial dilution is diluted 1:100 in assay media and then added to the assay plate where the addition of other assay reagents dilute the compounds to the final test concentration in the assay with a DMSO concentration of 0.1%.

The following compounds were tested:
Compound 4
N-ethyl-N-phenyl-5-chloro-1,2-dihydro-4-hydroxy-1-methyl-2-oxo-quinoline-3-carboxamide (Laquinimod, an N-alkyl amide reference compound)
Compound 5
N-phenyl-5-chloro-1,2-dihydro-4-hydroxy-1-methyl-2-oxo-quinoline-3-carboxamide (N-hydrogen amide derivative of Laquinimod)

Compound 6
N-(4-trifluoromethylphenyl)-1,2-dihydro-4-hydroxy-5-methoxy-1-methyl-2-oxo-quinoline-3-carboxamide (Example 11)
Compound 7
N-phenyl-5-ethyl-1,2-dihydro-4-hydroxy-1-methyl-2-oxo-quinoline-3-carboxamide (Example 13)
Compound 8
N-(4-fluorophenyl)-6-chloro-1,2-dihydro-4-hydroxy-1-methyl-2-oxo-quinoline-3-carboxamide (Example 27)

The results shown in the table below are presented as % activation at different compound concentrations (nM) where 100% activation represents the maximum activation by the assay reference compound beta-naphthoflavone ($EC_{50}$ 2090 nM).

| % act. | 1 nM | 10 nM | 100 nM | 1000 nM | 10000 nM | 100000 nM |
|---|---|---|---|---|---|---|
| Cmpd 4 | | | | 6 | 17 | 52 |
| Cmpd 5 | 22 | 25 | 60 | | | |
| Cmpd 6 | 19 | 68 | 142 | | | |
| Cmpd 7 | 9 | 27 | 84 | | | |
| Cmpd 8 | 7 | 13 | 57 | | | |

The results show that the N-hydrogen-carboxanilide derivatives, contrary to the N-alkyl-carboxanilides, are potent activators of the aryl hydrocarbon receptor.

Example 211

In Vivo Activity in the MS Model Experimental Autoimmune Encephalomyelitis (EAE) in Rats EAE was induced day 0 in female Dark Agouti (DA) rats with subcutaneous injection of spinal cord homogenate (SCH, approximately 2 mg, from naive rats) emulsified in incomplete Freunds adjuvant (IFA, total volume 100 ul per rat) at the base of the tail. Disease was evaluated daily from day 5 until the end of the experiment (day 22) according to following criteria: 0=healthy, 1=tail weakness, 2=tail paralysis, 3=tail paralysis and mild waddle, 4=tail paralysis and severe waddle, 5=tail paralysis and paralysis of one limb, 6=tail paralysis and paralysis of both hind limbs, 7=tetraparesis or paralysis of three limbs, and 8=premorbid or dead. Statistical analysis was performed using Prism 5 for Mac OS X (GraphPad Software, San Diego, Calif., USA).
Experimental Groups and Treatment
Treatment was initiated day 0 after EAE induction with following treatment injections administered day 3, 6, and 9. The dose was administered as a 500 uL corn oil solution subcutaneously at the lower back. Treatment groups were mixed in all cages to avoid cage effects.
Groups:
Control (vehicle, corn oil, Sigma Aldrich), 11 animals
Cyclosporin A (positive control, Sigma Aldrich), 10 mg/kg, first dissolved in 70% EtOH to 50 mg/mL, 11 animals
Compound 9 (N-acetyl-N-phenyl-4-acetoxy-5-chloro-1,2-dihydro-1-methyl-2-oxo-quinoline-3-carboxamide, Example 74), 1 mg/kg, 10 animals Results in FIG. 1 show that administration of Compound 9 (1 mg/kg day 0, 3, 6, and 9) efficiently prevented EAE development. After discontinuation of treatment the severity of the first disease period was lower than for vehicle control treated animals.

REFERENCES

1. Derivatives of 6, 7 or 8 cycloalkyl 4-oxo quinoline 3 carboxylic acid. Ferrini, P. G. et al., U.S. Pat. No. 3,960,868A (Jun. 1, 1976, Ciba-Geigy Corporation).
2. Quinoline-3-carboxamides. Allais, A. et al., U.S. Pat. No. 4,107,310A (Aug. 15, 1978, Roussel Uclaf).
3. Anti-inflammatory agents. Part II. Synthesis and anti-inflammatory activity of 3,4-disubstituted 2-oxo-1,2-dihydroquinolines. Shridhar, D. R. et al., Indian Journal of Chemistry, Section B: Organic Chemistry Including Medicinal Chemistry (1979), 17B(5), 488-90.
4. Heterocyclic carboxamides, compositions containing these compounds and methods of treatment with these compositions. Eriksoo, E. et al., EP59698A1 (Sep. 8, 1982, A B Leo).
5a. Modified Synthesis and Antiangiogenetic Activity of Linomide. Khan, S. R. et al., Bioorganic & Medicinal Chemistry Letters (2001), 11, 451.
5b. Linomide Inhibits Angiogenesis, Growth, Metastasis, and Macrophage Infiltration within Rat Prostatic Cancers. Vukanovic, J. and Isaacs, J. T., Cancer Research (1995), 1499-1504.
6a. New use of substituted quinoline carboxamide. Abramsky, O. et al., WO9306829 (Apr. 15, 1993, Kabi Pharmacia AB).
6b. The use of quinoline-3-carboxamide compounds for treatment of diabetes. Slavin, S. et al., WO9319756 (Oct. 14, 1993, Kabi Pharmacia AB).
6c. New use of quinoline-3-carboxamide compounds. Nilsson, B. et al., WO9524195 (Sep. 14, 1995, Pharmacia AB).
6d. New use of quinoline-3-carboxamide compounds. Nilsson, B. et al., WO9524196 (Sep. 14, 1995, Pharmacia AB).
7a. Quinoline derivatives. Björk, A. et al., WO0003991 (Jan. 27, 2000, Active Biotech AB).
7b. Synthesis and Biological Evaluation of New 1,2-Dihydro-4-hydroxy-2-oxo-3-quinolinecarboxamides for Treatment of Autoimmune Disorders: Structure-Activity Relationship. Jonsson, S. et al., J. Med. Chem. (2004) 47, 2075-2088.
8. Identification of human S100A9 as a novel target for treatment of autoimmune disease via binding to quinoline-3-carboxamides. Björk, P. et al., PLoS Biol (2009), 7(4), 800-812.
9a. Quinoline derivatives. Matsuo, M. et al., WO9218483 (Oct. 29, 1992, Fujisawa Pharmaceutical Co. Ltd.).
9b. Heterocyclic derivatives with immunomodulating activity. Matsuo, M. et al., WO9429295 (Dec. 22, 1994, Fujisawa Pharmaceutical Co. Ltd.).
9c. Heterotricyclic derivatives, process for their preparation and pharmaceutical compositions containing them. Matsuo, M. et al., U.S. Pat. No. 5,739,130 (Apr. 14, 1998, Fujisawa Pharmaceutical Co. Ltd.).
9d. Synthesis and Antinephritic Activities of Quinoline-3-carboxamides and Related Compounds. Kiyoshi Tsuji, et al., Bioorganic & Medicinal Chemistry Letters 12 (2002) 85-88.
10. Thienopyridone carboxamides and their medical use. Björk, A. and Jansson, K., WO2005123744 (Dec. 29, 2005, Active Biotech AB).
11. Pyridylamides of 1-R-2-oxo-4-hydroxyquinoline-3-carboxylic acids. Synthesis, physical, chemical and antituberculous properties. Ukrainets, I. V. et al., Visnik Farmatsii (2004), (1), 12-19.
12. Synthesis and Reactivity of Laquinimod, a Quinoline-3-carboxamide: Intramolecular Transfer of the Enol Proton to a Nitrogen Atom as a Plausible Mechanism for Ketene Formation. Jansson, K. et al., J. Org. Chem. 2006, 71, 1658-1667.
13. New compositions containing quinoline compounds. Jansson, K. et al., US2005/0192315A1 (Sep. 1, 2005, Active Biotech AB).
14a. Identification of cytochrome P4503A as the major subfamily responsible for the metabolism of roquinimex in man. Tuvesson, H. et al., Xenobiotica (2000), 30(9), 905-914.
14b. Cytochrome P450 3A4 is the major enzyme responsible for the metabolism of laquinimod, a novel immunomodulator. Tuvesson, H. et al., Drug Metabolism and Disposition (2005), 33(6), 866-872.
15a. The mammalian basic helix-loop-helix/PAS family of transcriptional regulators. Kewley, R. J. et al., The International Journal of Biochemistry & Cell Biology 36 (2004) 189-204.
15b. CDNAs and proteins involved in hypoxia, circadian and orphan signal transduction pathways, and methods of use. Bradfield, C. A. et al., U.S. Pat. No. 7,105,647B1 (Sep. 12, 2006, Wisconsin Alumni Research Foundation).
16a. Control of Treg and TH17 cell differentiation by the aryl hydrocarbon receptor. Quintana, F. J. et al., Nature (2008), 453, 65.
16b. The AhR links Th17-cell-mediated autoimmunity to environmental toxins. Veldhoen, M. et al., Nature (2008) 453, 106.
16c. The aryl hydrocarbon receptor: a regulator of Th17 and Treg cell development in disease. Ho, P. P. and Steinman, L., Cell Research (2008), 18, 605-608.
16d. Type 1 regulatory T cells (Tr1) in autoimmunity. Pot, C. et al., Seminars in Immunology (2011), 23, 202-208.
16e. Activation of aryl hydrocarbon receptor by TCDD prevents diabetes in NOD mice with increased frequency of $CD4^+CD25^+Foxp3^+$ cells in pancreatic lymphnodes. Kerkyliet, N. I. et al., Immunotherapy (2009), 1, 539-547.
16f. Aryl Hydrocarbon Receptor Activation by TCDD Reduces Inflammation Associated with Crohn's Disease. Benson, J. M. and Shepherd, D. M., Toxicol. Sci. (2011) 120, 68-78.
16g. Activation of Aryl Hydrocarbon Receptor (AhR) Leads to Reciprocal Epigenetic Regulation of FoxP3 and IL-17 Expression and Amelioration of Experimental Colitis. Singh, N. P. et al., PLoS ONE (2011), 6, 1-13.
16h. Suppression of Experimental Autoimmune Uveoretinitis by Inducing Differentiation of Regulatory T Cells via Activation of Aryl Hydrocarbon Receptor. Zhang, L. et al., IOVS, (2010), 51, 2109-2117.
17a. Activation of the aryl hydrocarbon receptor is essential for mediating the anti-inflammatory effects of a novel low-molecular-weight compound. Lawrence, B. P. et al., BLOOD (2008), 112, 1158-1165.
17b. Activation of the Aryl Hydrocarbon Receptor Suppresses Sensitization in a Mouse Peanut Allergy Model. Schultz, V. J. et al., Toxicol. Sci. (2011), 123, 491-500.
17c. Activation of the aryl hydrocarbon receptor promotes allograft-specific tolerance through direct and dendritic cell-mediated effects on regulatory T cells. Hauben, E. et al., BLOOD (2008), 112, 1214-1222.
17d. F.-L. Yuan et al., Regulatory T cells as a potent target for controlling bone loss. Biochem. Biophys. Res. Commun. (2010), 402, 173-176.
17e. Dousing diabetes' flames. Osherovich, L., Science-Business eXchange (2009)$_2$, (31), and refs therein.
18. Dioxin receptor is a ligand-dependent E3 ubiquitin ligase. Ohtake, F. et al., Nature (2007), 446, 562.
19. Aryl hydrocarbon receptor suppresses intestinal carcinogenesis in $Apc^{Min/+}$ mice with natural ligands. Kawajiria, K. et al., PNAS (2009) 106, (32), 13481-13486.
20. AHR signaling in prostate growth, morphogenesis, and disease. Vezina, C. M., Tien-Min Lin, T.-M., Peterson, R. E., Biochemical Pharmacology (2009), 77, 566-576.
21. The role of hypoxia-inducible factors in tumorigenesis. Rankin, E. B. and Giaccia, A. J., Cell Death and Differentiation (2008) 15, 678-685.
22. Aryl Hydrocarbon Receptor (AhR) is Activated by Glucose and Regulates the Thrombospondin-1 Gene Promoter in Endothelial Cells. Dabir, P. et al., Circ Res. (2008), 102(12), 1558-1565.
23a. Symposium Report Regulation of Drug-Metabolizing Enzymes and Transporters in Infection, Inflammation, and Cancer. Morgan, E. T. et al., DMD (2008), 36, 205-216
23b. Down-regulation of human CYP3A4 by the inflammatory signal interleukin-6: molecular mechanism and transcription factors involved. Jover, R. et al., FASEB J. (2002), 16, 1799-1801.

The invention claimed is:

1. A compound of the general formula I or a pharmaceutically acceptable salt thereof:

wherein

A, B and C are independently selected from the group consisting of H, Me, Et, iso-Pr, tert-Bu, OMe, OEt, O-iso-Pr, SMe, S(O)Me, S(O)$_2$Me, CF$_3$, OCF$_3$, F, Cl, Br, I, and CN, or A and B represents OCH$_2$O and C is H;

RN is selected from the group consisting of H, C(O)Me, C(O)Et, C(O)Pr, C(O)CH(Me)$_2$, C(O)C(Me)$_3$, C(O)Ph, C(O)CH$_2$Ph, CO$_2$Me, CO$_2$Et, CO$_2$CH$_2$Ph;

R4 is RN, or when RN is H, then R4 is selected from the group consisting of H, P(O)(OH)$_2$, P(O)(OMe)$_2$, P(O)(OEt)$_2$, P(O)(OPh)$_2$, P(O)(OCH$_2$Ph)$_2$, C(O)Me, C(O)Et, C(O)Pr, C(O)CH(Me)$_2$, C(O)C(Me)$_3$, C(O)Ph, C(O)CH$_2$Ph, CO$_2$H, CO$_2$Me, CO$_2$Et, CO$_2$CH$_2$Ph;

R5 and R6 are independently selected from the group consisting of H, Me, Et, iso-Pr, tert-Bu, OMe, OEt, O-iso-Pr, SMe, S(O)Me, S(O)$_2$Me, CF$_3$, OCF$_3$, F, Cl, Br, I, and CN, or R5 and R6 represents OCH$_2$O; and X is —CH=CH—, or S, with the proviso that compound I is not selected from the group consisting of N-phenyl-1,2-dihydro-4-hydroxy-1-methyl-2-oxo-quinoline-3-carboxamide, N-(4-methylphenyl)-1,2-dihydro-4-hydroxy-1-methyl-2-oxo-quinoline-3-carboxamide, N-(4-methoxyphenyl)-1,2-dihydro-4-hydroxy-1-methyl-2-oxo-quinoline-3-carboxamide, N-(4-ethoxyphenyl)-1,2-dihydro-4-hydroxy-1-methyl-2-oxo-quinoline-3-carboxamide, N-(4-trifluoromethoxyphenyl)-1,2-dihydro-4-hydroxy-1-methyl-2-oxo-quinoline-3-carboxamide, N-(4-chlorophenyl)-1,2-dihydro-4-hydroxy-1-methyl-2-oxo-quinoline-3-carboxamide,
N-(4-bromophenyl)-1,2-dihydro-4-hydroxy-1-methyl-2-oxo-quinoline-3-carboxamide,
N-(3,4-dichlorophenyl)-1,2-dihydro-4-hydroxy-1-methyl-2-oxo-3-quinoline-3-carboxamide,
N-(3,5-dimethylphenyl)-1,2-dihydro-4-hydroxy-1-methyl-2-oxo-quinoline-3-carboxamide,
N-(3-methylphenyl)-1,2-dihydro-4-hydroxy-1-methyl-2-oxo-quinoline-3-carboxamide,
N-(3-chlorophenyl)-1,2-dihydro-4-hydroxy-1-methyl-2-oxo-quinoline-3-carboxamide,
N-(3-methoxyphenyl)-1,2-dihydro-4-hydroxy-1-methyl-2-oxo-quinoline-3-carboxamide,
N-(3-methylthiophenyl)-1,2-dihydro-4-hydroxy-1-methyl-2-oxo-quinoline-3-carboxamide,
N-(3-trifluoromethylphenyl)-1,2-dihydro-4-hydroxy-1-methyl-2-oxo-quinoline-3-carboxamide,
N-(3-bromophenyl)-1,2-dihydro-4-hydroxy-1-methyl-2-oxo-quinoline-3-carboxamide,
N-(3,4-methylenedioxo)-1,2-dihydro-4-hydroxy-1-methyl-2-oxo-quinoline-3-carboxamide,
N-phenyl-5-chloro-1,2-dihydro-4-hydroxy-1-methyl-2-oxo-quinoline-3-carboxamide,
N-phenyl-5-fluoro-1,2-dihydro-4-hydroxy-1-methyl-2-oxo-quinoline-3-carboxamide,
N-phenyl-1,2-dihydro-4-hydroxy-1,6-dimethyl-2-oxo-quinoline-3-carboxamide,
N-phenyl-1,2-dihydro-4-hydroxy-6-methoxy-1-methyl-2-oxo-quinoline-3-carboxamide,
N-phenyl-1,2-dihydro-4-hydroxy-1-methyl-6-methylthio-2-oxo-quinoline-3-carboxamide, and
N-phenyl-6-chloro-1,2-dihydro-4-hydroxy-1-methyl-2-oxo-quinoline-3-carboxamide.

2. The compound or a pharmaceutically acceptable salt thereof according to claim 1, wherein
A, B and C are independently selected from the group consisting of H, Me, OMe, $CF_3$, $OCF_3$, F, Cl, and Br, or A and B represents $OCH_2O$ and C is H; and
R5 and R6 are independently selected from the group consisting of H, Me, Et, OMe, SMe, S(O)Me, $CF_3$, $OCF_3$, F, Cl, and Br, or R5 and R6 represents $OCH_2O$.

3. The compound or a pharmaceutically acceptable salt thereof according to claim 1, wherein
A, B and C are independently selected from the group consisting of Me, OMe, $CF_3$, $OCF_3$, F, and Cl, or A and B represents $OCH_2O$ and C is H; and
R5 and R6 are independently selected from the group consisting of Me, Et, OMe, SMe, S(O)Me, $CF_3$, F, and Cl, or R5 and R6 represents $OCH_2O$.

4. The compound or a pharmaceutically acceptable salt thereof according to claim 1, wherein
RN is selected from the group consisting of H, C(O)Me, C(O)Et, C(O)Pr, C(O)CH(Me)$_2$, C(O)C(Me)$_3$, C(O)Ph, C(O)CH$_2$Ph, CO$_2$Me, CO$_2$Et, and,
R4 is RN, or when RN is H, then R4 is selected from the group consisting of P(O)(OH)$_2$, P(O)(OMe)$_2$, P(O)(OEt)$_2$, P(O)(OPh)$_2$, P(O)(OCH$_2$Ph)$_2$, C(O)Me, C(O)Et, C(O)Pr, C(O)CH(Me)$_2$, C(O)C(Me)$_3$, C(O)Ph, C(O)CH$_2$Ph, CO$_2$Me and CO$_2$Et;
with the proviso that R4 is not H.

5. The compound or a pharmaceutically acceptable salt thereof according to claim 1, wherein
RN is selected from the group consisting of C(O)Me, C(O)Et, C(O)Pr, C(O)CH(Me)$_2$, C(O)C(Me)$_3$, C(O)Ph, CO$_2$Me, and CO$_2$Et; and
R4 is RN.

6. The compound or a pharmaceutically acceptable salt thereof according to claim 1, wherein
RN is H; and
R4 is selected from the group consisting of P(O)(OH)$_2$, P(O)(OMe)$_2$, P(O)(OEt)$_2$, P(O)(OPh)$_2$, P(O)(OCH$_2$Ph)$_2$, C(O)Me, C(O)Et, C(O)Pr, C(O)CH(Me)$_2$, C(O)C(Me)$_3$, C(O)Ph, C(O)CH$_2$Ph, CO$_2$Me and CO$_2$Et.

7. The compound or a pharmaceutically acceptable salt thereof according to claim 1, wherein
RN is H; and
R4 is H.

8. The compound according to claim 1 or a pharmaceutically acceptable salt thereof, wherein
X is S.

9. The compound or a pharmaceutically acceptable salt thereof according to claim 1, wherein
A, B and C are independently selected from the group consisting of H, Me, OMe, $CF_3$, $OCF_3$, F, Cl, and Br, or A and B represents $OCH_2O$ and C is H;
R5 is selected from the group consisting of H, Me, Et, $CF_3$, Cl, and Br;
R6 is H; and
X is S.

10. The compound or a pharmaceutically acceptable salt thereof according to claim 1, which is selected from the group consisting of
N-acetyl-N-phenyl-4-acetoxy-1,2-dihydro-1-methyl-2-oxo-quinoline-3-carboxamide,
N-phenyl-4-acetoxy-1,2-dihydro-1-methyl-2-oxo-quinoline-3-carboxamide,
N-iso-butyryl-N-phenyl-4-iso-butyryloxy-1,2-dihydro-1-methyl-2-oxo-quinoline-3-carboxamide,
N-phenyl-4-iso-butyryloxy-1,2-dihydro-1-methyl-2-oxo-quinoline-3-carboxamide,
N-benzoyl-N-phenyl-4-benzoyloxy-1,2-dihydro-1-methyl-2-oxo-quinoline-3-carboxamide,
N-phenyl-4-benzoyloxy-1,2-dihydro-1-methyl-2-oxo-quinoline-3-carboxamide,
N-ethoxycarbonyl-N-phenyl-4-ethoxycarbonyloxy-1,2-dihydro-1-methyl-2-oxo-quinoline-3-carboxamide,
N-phenyl-4-diethylphosphoryloxy-1,2-dihydro-1-methyl-2-oxo-quinoline-3-carboxamide,
N-acetyl-N-(4-methylphenyl)-4-acetoxy-1,2-dihydro-1-methyl-2-oxo-quinoline-3-carboxamide,
N-(4-methylphenyl)-4-acetoxy-1,2-dihydro-1-methyl-2-oxo-quinoline-3-carboxamide,
N-iso-butyryl-N-(4-methylphenyl)-4-iso-butyryloxy-1,2-dihydro-1-methyl-2-oxo-quinoline-3-carboxamide,
N-(4-methylphenyl)-4-iso-butyryloxy-1,2-dihydro-1-methyl-2-oxo-quinoline-3-carboxamide,
N-benzoyl-N-(4-methylphenyl)-4-benzoyloxy-1,2-dihydro-1-methyl-2-oxo-quinoline-3-carboxamide,
N-ethoxycarbonyl-N-(4-methylphenyl)-4-ethoxycarbonyloxy-1,2-dihydro-1-methyl-2-oxo-quinoline-3-carboxamide,
N-(4-fluorophenyl)-1,2-dihydro-4-hydroxy-1-methyl-2-oxo-quinoline-3-carboxamide,
N-acetyl-N-(4-fluorophenyl)-4-acetoxy-1,2-dihydro-1-methyl-2-oxo-quinoline-3-carboxamide,
N-(4-fluorophenyl)-4-acetoxy-1,2-dihydro-1-methyl-2-oxo-quinoline-3-carboxamide,
N-iso-butyryl-N-(4-fluorophenyl)-4-iso-butyryloxy-1,2-dihydro-1-methyl-2-oxo-quinoline-3-carboxamide,
N-(4-fluorophenyl)-4-iso-butyryloxy-1,2-dihydro-1-methyl-2-oxo-quinoline-3-carboxamide,
N-benzoyl-N-(4-fluorophenyl)-4-benzoyloxy-1,2-dihydro-1-methyl-2-oxo-quinoline-3-carboxamide, N-ethoxycarbonyl-N-(4-fluorophenyl)-4-ethoxycarbonyloxy-1,2-dihydro-1-methyl-2-oxo-quinoline-3-carboxamide,
N-acetyl-N-(4-chlorophenyl)-4-acetoxy-1,2-dihydro-1-methyl-2-oxo-quinoline-3-carboxamide,
N-(4-chlorophenyl)-4-acetoxy-1,2-dihydro-1-methyl-2-oxo-quinoline-3-carboxamide,
N-iso-butyryl-N-(4-chlorophenyl)-4-iso-butyryloxy-1,2-dihydro-1-methyl-2-oxo-quinoline-3-carboxamide,
N-(4-chlorophenyl)-4-iso-butyryloxy-1,2-dihydro-1-methyl-2-oxo-quinoline-3-carboxamide,
N-benzoyl-N-(4-chlorophenyl)-4-benzoyloxy-1,2-dihydro-1-methyl-2-oxo-quinoline-3-carboxamide,
N-(4-chlorophenyl)-N-ethoxycarbonyl-4-ethoxycarbonyloxy-1,2-dihydro-1-methyl-2-oxo-quinoline-3-carboxamide,
N-acetyl-N-(4-methoxyphenyl)-4-acetoxy-1,2-dihydro-1-methyl-2-oxo-quinoline-3-carboxamide,
N-(4-methoxyphenyl)-4-acetoxy-1,2-dihydro-1-methyl-2-oxo-quinoline-3-carboxamide,
N-iso-butyryl-N-(4-methoxyphenyl)-4-iso-butyryloxy-1,2-dihydro-1-methyl-2-oxo-quinoline-3-carboxamide,
N-(4-methoxyphenyl)-4-iso-butyryloxy-1,2-dihydro-1-methyl-2-oxo-quinoline-3-carboxamide,
N-benzoyl-N-(4-methoxyphenyl)-4-benzoyloxy-1,2-dihydro-1-methyl-2-oxo-quinoline-3-carboxamide,
N-ethoxycarbonyl-N-(4-methoxyphenyl)-4-ethoxycarbonyloxy-1,2-dihydro-1-methyl-2-oxo-quinoline-3-carboxamide,
N-(4-trifluoromethylphenyl)-1,2-dihydro-4-hydroxy-1-methyl-2-oxo-quinoline-3-carboxamide,
N-acetyl-N-(4-trifluoromethylphenyl)-4-acetoxy-1,2-dihydro-1-methyl-2-oxo-quinoline-3-carboxamide,
N-(4-trifluoromethylphenyl)-4-acetoxy-1,2-dihydro-1-methyl-2-oxo-quinoline-3-carboxamide,
N-iso-butyryl-N-(4-trifluoromethylphenyl)-4-iso-butyryloxy-1,2-dihydro-1-methyl-2-oxo-quinoline-3-carboxamide,
N-benzoyl-N-(4-trifluoromethylphenyl)-4-benzoyloxy-1,2-dihydro-1-methyl-2-oxo-quinoline-3-carboxamide,
N-ethoxycarbonyl-N-(4-trifluoromethylphenyl)-4-ethoxycarbonyloxy-1,2-dihydro-1-methyl-2-oxo-quinoline-3-carboxamide,
N-acetyl-N-(4-trifluoromethoxyphenyl)-4-acetoxy-1,2-dihydro-1-methyl-2-oxo-quinoline-3-carboxamide,
N-(4-trifluoromethoxyphenyl)-4-acetoxy-1,2-dihydro-1-methyl-2-oxo-quinoline-3-carboxamide,
N-(3,4-difluorophenyl)-1,2-dihydro-4-hydroxy-1-methyl-2-oxo-quinoline-3-carboxamide,
N-acetyl-N-(3,4-difluorophenyl)-4-acetoxy-1,2-dihydro-1-methyl-2-oxo-quinoline-3-carboxamide,
N-(3,4-difluorophenyl)-4-acetoxy-1,2-dihydro-1-methyl-2-oxo-quinoline-3-carboxamide,
N-(3,5-di-(trifluoromethyl)phenyl)-1,2-dihydro-4-hydroxy-1-methyl-2-oxo-quinoline-3-carboxamide,
N-(4-methylthiophenyl)-1,2-dihydro-4-hydroxy-1-methyl-2-oxo-quinoline-3-carboxamide,
N-acetyl-N-(3,4-methylenedioxyphenyl)-4-acetoxy-1,2-dihydro-1-methyl-2-oxo-quinoline-3-carboxamide,
N-(4-methylenedioxyphenyl)-4-acetoxy-1,2-dihydro-1-methyl-2-oxo-quinoline-3-carboxamide,
N-phenyl-1,2-dihydro-4-hydroxy-1,5-dimethyl-2-oxo-quinoline-3-carboxamide,
N-acetyl-N-phenyl-4-acetoxy-1,2-dihydro-1,5-dimethyl-2-oxo-quinoline-3-carboxamide,
N-phenyl-4-acetoxy-1,2-dihydro-1,5-dimethyl-2-oxo-quinoline-3-carboxamide,
N-(4-chlorophenyl)-1,2-dihydro-4-hydroxy-1,5-dimethyl-2-oxo-quinoline-3-carboxamide,
N-acetyl-N-(4-chlorophenyl)-4-acetoxy-1,2-dihydro-1,5-dimethyl-2-oxo-quinoline-3-carboxamide,
N-(4-chlorophenyl)-4-acetoxy-1,2-dihydro-1,5-dimethyl-2-oxo-quinoline-3-carboxamide,
N-(4-methoxyphenyl)-1,2-dihydro-4-hydroxy-1,5-dimethyl-2-oxo-quinoline-3-carboxamide,
N-acetyl-N-(4-methoxyphenyl)-4-acetoxy-1,2-dihydro-1,5-dimethyl-2-oxo-quinoline-3-carboxamide,
N-(4-methoxyphenyl)-4-acetoxy-1,2-dihydro-1,5-dimethyl-2-oxo-quinoline-3-carboxamide,
N-phenyl-5-ethyl-1,2-dihydro-4-hydroxy-1-methyl-2-oxo-quinoline-3-carboxamide,
N-acetyl-N-phenyl-4-acetoxy-5-ethyl-1,2-dihydro-1-methyl-2-oxo-quinoline-3-carboxamide,
N-phenyl-4-acetoxy-5-ethyl-1,2-dihydro-1-methyl-2-oxo-quinoline-3-carboxamide,
N-iso-butyryl-N-phenyl-4-iso-butyryloxy-5-ethyl-1,2-dihydro-1-methyl-2-oxo-quinoline-3-carboxamide,
N-phenyl-4-iso-butyryloxy-5-ethyl-1,2-dihydro-1-methyl-2-oxo-quinoline-3-carboxamide,
N-benzoyl-N-phenyl-4-benzoyloxy-5-ethyl-1,2-dihydro-1-methyl-2-oxo-quinoline-3-carboxamide,
N-phenyl-4-benzoyloxy-5-ethyl-1,2-dihydro-1-methyl-2-oxo-quinoline-3-carboxamide,
N-ethoxycarbonyl-N-phenyl-4-ethoxycarbonyloxy-5-ethyl-1,2-dihydro-1-methyl-2-oxo-quinoline-3-carboxamide,
N-phenyl-4-diethylphosphoryloxy-5-ethyl-1,2-dihydro-1-methyl-2-oxo-quinoline-3-carboxamide,
N-(4-chlorophenyl)-5-ethyl-1,2-dihydro-4-hydroxy-1-methyl-2-oxo-quinoline-3-carboxamide,
N-acetyl-N-(4-chlorophenyl)-4-acetoxy-5-ethyl-1,2-dihydro-1-methyl-2-oxo-quinoline-3-carboxamide,
N-(4-chlorophenyl)-4-acetoxy-5-ethyl-1,2-dihydro-1-methyl-2-oxo-quinoline-3-carboxamide,
N-(4-chlorophenyl)-4-iso-butyryloxy-5-ethyl-1,2-dihydro-1-methyl-2-oxo-quinoline-3-carboxamide,
N-benzoyl-N-(4-chlorophenyl)-4-benzoyloxy-5-ethyl-1,2-dihydro-1-methyl-2-oxo-quinoline-3-carboxamide,
N-(4-methoxyphenyl)-5-ethyl-1,2-dihydro-4-hydroxy-1-methyl-2-oxo-quinoline-3-carboxamide,
N-acetyl-N-(4-methoxyphenyl)-4-acetoxy-5-ethyl-1,2-dihydro-1-methyl-2-oxo-quinoline-3-carboxamide,
N-(4-methoxyphenyl)-4-acetoxy-5-ethyl-1,2-dihydro-1-methyl-2-oxo-quinoline-3-carboxamide,
N-phenyl-1,2-dihydro-4-hydroxy-1-methyl-2-oxo-5-trifluoromethyl-quinoline-3-carboxamide,
N-acetyl-N-phenyl-4-acetoxy-1,2-dihydro-1-methyl-2-oxo-5-trifluoromethyl-quinoline-3-carboxamide,
N-phenyl-4-acetoxy-1,2-dihydro-1-methyl-2-oxo-5-trifluoromethyl-quinoline-3-carboxamide,
N-phenyl-1,2-dihydro-4-hydroxy-5-methoxy-1-methyl-2-oxo-quinoline-3-carboxamide,
N-acetyl-N-phenyl-4-acetoxy-1,2-dihydro-5-methoxy-1-methyl-2-oxo-quinoline-3-carboxamide,
N-phenyl-4-acetoxy-1,2-dihydro-5-methoxy-1-methyl-2-oxo-quinoline-3-carboxamide,
N-iso-butyryl-N-phenyl-4-iso-butyryloxy-1,2-dihydro-5-methoxy-1-methyl-2-oxo-quinoline-3-carboxamide,
N-phenyl-4-iso-butyryloxy-1,2-dihydro-5-methoxy-1-methyl-2-oxo-quinoline-3-carboxamide,
N-benzoyl-N-phenyl-4-benzoyloxy-1,2-dihydro-5-methoxy-1-methyl-2-oxo-quinoline-3-carboxamide,
N-phenyl-4-benzoyloxy-1,2-dihydro-5-methoxy-1-methyl-2-oxo-quinoline-3-carboxamide, N-(4-fluorophenyl)-1,2-dihydro-4-hydroxy-5-methoxy-1-methyl-2-oxo-quinoline-3-carboxamide,
N-acetyl-N-(4-fluorophenyl)-4-acetoxy-1,2-dihydro-5-methoxy-1-methyl-2-oxo-quinoline-3-carboxamide,
N-(4-fluorophenyl)-4-acetoxy-1,2-dihydro-5-methoxy-1-methyl-2-oxo-quinoline-3-carboxamide,
N-iso-butyryl-N-(4-fluorophenyl)-4-iso-butyryloxy-1,2-dihydro-5-methoxy-1-methyl-2-oxo-quinoline-3-carboxamide,
N-(4-fluorophenyl)-4-iso-butyryloxy-1,2-dihydro-5-methoxy-1-methyl-2-oxo-quinoline-3-carboxamide,
N-benzoyl-N-(4-fluorophenyl)-4-benzoyloxy-1,2-dihydro-5-methoxy-1-methyl-2-oxo-quinoline-3-carboxamide,
N-(4-fluorophenyl)-4-benzoyloxy-1,2-dihydro-5-methoxy-1-methyl-2-oxo-quinoline-3-carboxamide,
N-(4-trifluoromethylphenyl)-1,2-dihydro-4-hydroxy-5-methoxy-1-methyl-2-oxo-quinoline-3-carboxamide,
N-acetyl-N-(4-trifluoromethylphenyl)-4-acetoxy-1,2-dihydro-5-methoxy-1-methyl-2-oxo-quinoline-3-carboxamide,
N-(4-trifluoromethylphenyl)-4-acetoxy-1,2-dihydro-5-methoxy-1-methyl-2-oxo-quinoline-3-carboxamide,
N-iso-butyryl-N-(4-trifluoromethylphenyl)-4-iso-butyryloxy-1,2-dihydro-5-methoxy-1-methyl-2-oxo-quinoline-3-carboxamide,
N-(4-trifluoromethylphenyl)-4-iso-butyryloxy-1,2-dihydro-5-methoxy-1-methyl-2-oxo-quinoline-3-carboxamide,
N-benzoyl-N-(4-trifluoromethylphenyl)-4-benzoyloxy-1,2-dihydro-5-methoxy-1-methyl-2-oxo-quinoline-3-carboxamide,
N-(4-trifluoromethylphenyl)-4-benzoyloxy-1,2-dihydro-5-methoxy-1-methyl-2-oxo-quinoline-3-carboxamide,
N-ethoxycarbonyl-N-(4-trifluoromethylphenyl)-4-ethoxycarbonyloxy-1,2-dihydro-5-methoxy-1-methyl-2-oxo-quinoline-3-carboxamide,
N-(4-trifluoromethylphenyl)-4-diethylphosphoryloxy-1,2-dihydro-5-methoxy-1-methyl-2-oxo-quinoline-3-carboxamide,
N-acetyl-N-phenyl-4-acetoxy-5-fluoro-1,2-dihydro-1-methyl-2-oxo-quinoline-3-carboxamide,
N-phenyl-4-acetoxy-5-fluoro-1,2-dihydro-1-methyl-2-oxo-quinoline-3-carboxamide,
N-acetyl-N-phenyl-4-acetoxy-5-chloro-1,2-dihydro-1-methyl-2-oxo-quinoline-3-carboxamide,
N-phenyl-4-acetoxy-5-chloro-1,2-dihydro-1-methyl-2-oxo-quinoline-3-carboxamide,
N-iso-butyryl-N-phenyl-4-iso-butyryloxy-5-chloro-1,2-dihydro-1-methyl-2-oxo-quinoline-3-carboxamide,
N-phenyl-4-iso-butyryloxy-5-chloro-1,2-dihydro-1-methyl-2-oxo-quinoline-3-carboxamide,
N-benzoyl-N-phenyl-4-benzoyloxy-5-chloro-1,2-dihydro-1-methyl-2-oxo-quinoline-3-carboxamide,
N-phenyl-4-benzoyloxy-5-chloro-1,2-dihydro-1-methyl-2-oxo-quinoline-3-carboxamide,
N-ethoxycarbonyl-N-phenyl-4-ethoxycarbonyloxy-5-chloro-1,2-dihydro-1-methyl-2-oxo-quinoline-3-carboxamide,
N-phenyl-4-diethylphosphoryloxy-5-chloro-1,2-dihydro-1-methyl-2-oxo-quinoline-3-carboxamide,
N-(4-methylphenyl)-5-chloro-1,2-dihydro-4-hydroxy-1-methyl-2-oxo-quinoline-3-carboxamide,
N-acetyl-N-(4-methylphenyl)-4-acetoxy-5-chloro-1,2-dihydro-1-methyl-2-oxo-quinoline-3-carboxamide,
N-(4-methylphenyl)-4-acetoxy-5-chloro-1,2-dihydro-1-methyl-2-oxo-quinoline-3-carboxamide,
N-ethoxycarbonyl-N-(4-methylphenyl)-5-chloro-4-ethoxycarbonyloxy-1,2-dihydro-1-methyl-2-oxo-quinoline-3-carboxamide,
N-(4-methoxyphenyl)-5-chloro-1,2-dihydro-4-hydroxy-1-methyl-2-oxo-quinoline-3-carboxamide,
N-acetyl-N-(4-methoxyphenyl)-4-acetoxy-5-chloro-1,2-dihydro-1-methyl-2-oxo-quinoline-3-carboxamide,
N-iso-butyryl-N-(4-methoxyphenyl)-4-iso-butyryloxy-5-chloro-1,2-dihydro-1-methyl-2-oxo-quinoline-3-carboxamide,
N-(4-methoxyphenyl)-4-acetoxy-5-chloro-1,2-dihydro-1-methyl-2-oxo-quinoline-3-carboxamide,
N-(4-chlorophenyl)-5-chloro-1,2-dihydro-4-hydroxy-1-methyl-2-oxo-quinoline-3-carboxamide,
N-acetyl-N-(4-chlorophenyl)-4-acetoxy-5-chloro-1,2-dihydro-1-methyl-2-oxo-quinoline-3-carboxamide,
N-(4-chlorophenyl)-4-acetoxy-5-chloro-1,2-dihydro-1-methyl-2-oxo-quinoline-3-carboxamide,
N-phenyl-5-bromo-1,2-dihydro-4-hydroxy-1-methyl-2-oxo-quinoline-3-carboxamide,
N-acetyl-N-phenyl-4-acetoxy-5-bromo-1,2-dihydro-1-methyl-2-oxo-quinoline-3-carboxamide,
N-phenyl-4-acetoxy-5-bromo-1,2-dihydro-1-methyl-2-oxo-quinoline-3-carboxamide,
N-phenyl-1,2-dihydro-4-hydroxy-1-methyl-5-methylthio-2-oxo-quinoline-3-carboxamide,
N-acetyl-N-phenyl-4-acetoxy-1,2-dihydro-1-methyl-5-methylthio-2-oxo-quinoline-3-carboxamide,
N-phenyl-4-acetoxy-1,2-dihydro-1-methyl-5-methylthio-2-oxo-quinoline-3-carboxamide,
N-phenyl-1,2-dihydro-4-hydroxy-5,6-methylenedioxy-1-methyl-2-oxo-quinoline-3-carboxamide,
N-acetyl-N-phenyl-4-acetoxy-1,2-dihydro-5,6-methylenedioxy-1-methyl-2-oxo-quinoline-3-carboxamide,
N-phenyl-4-acetoxy-1,2-dihydro-5,6-methylenedioxy-1-methyl-2-oxo-quinoline-3-carboxamide,
N-(4-methoxyphenyl)-1,2-dihydro-4-hydroxy-5,6-methylenedioxy-1-methyl-2-oxo-quinoline-3-carboxamide,
N-(4-methoxyphenyl)-N-phenyl-4-acetoxy-1,2-dihydro-5,6-methylenedioxy-1-methyl-2-oxo-quinoline-3-carboxamide,
N-(4-methoxyphenyl)-4-acetoxy-1,2-dihydro-5,6-methylenedioxy-1-methyl-2-oxo-quinoline-3-carboxamide,
N-(4-chlorophenyl)-1,2-dihydro-4-hydroxy-5,6-methylenedioxy-1-methyl-2-oxo-quinoline-3-carboxamide,
N-(4-chlorophenyl)-N-phenyl-4-acetoxy-1,2-dihydro-5,6-methylenedioxy-1-methyl-2-oxo-quinoline-3-carboxamide,
N-(4-chlorophenyl)-4-acetoxy-1,2-dihydro-5,6-methylenedioxy-1-methyl-2-oxo-quinoline-3-carboxamide,
N-acetyl-N-phenyl-4-acetoxy-1,2-dihydro-1,6-dimethyl-2-oxo-quinoline-3-carboxamide,
N-phenyl-4-acetoxy-1,2-dihydro-1,6-dimethyl-2-oxo-quinoline-3-carboxamide,
N-phenyl-1,2-dihydro-4-hydroxy-1-methyl-2-oxo-6-trifluoromethyl-quinoline-3-carboxamide,
N-acetyl-N-phenyl-4-acetoxy-1,2-dihydro-1-methyl-2-oxo-6-trifluoromethyl-quinoline-3-carboxamide,
N-phenyl-4-acetoxy-1,2-dihydro-1-methyl-2-oxo-6-trifluoromethyl-quinoline-3-carboxamide,
N-acetyl-N-phenyl-4-acetoxy-1,2-dihydro-6-methoxy-1-methyl-2-oxo-quinoline-3-carboxamide,
N-phenyl-4-acetoxy-1,2-dihydro-6-methoxy-1-methyl-2-oxo-quinoline-3-carboxamide,
N-iso-butyryl-N-phenyl-4-iso-butyryloxy-1,2-dihydro-6-methoxy-1-methyl-2-oxo-quinoline-3-carboxamide, N-phenyl-4-iso-butyryloxy-1,2-dihydro-6-methoxy-1-methyl-2-oxo-quinoline-3-carboxamide,
N-benzoyl-N-phenyl-4-benzoyloxy-1,2-dihydro-6-methoxy-1-methyl-2-oxo-quinoline-3-carboxamide,
N-phenyl-4-benzoyloxy-1,2-dihydro-6-methoxy-1-methyl-2-oxo-quinoline-3-carboxamide,
N-ethoxycarbonyl-N-phenyl-4-ethoxycarbonyloxy-1,2-dihydro-6-methoxy-1-methyl-2-oxo-quinoline-3-carboxamide,
N-phenyl-4-diethylphosphoryloxy-1,2-dihydro-6-methoxy-1-methyl-2-oxo-quinoline-3-carboxamide,
N-(4-fluorophenyl)-1,2-dihydro-4-hydroxy-6-methoxy-1-methyl-2-oxo-quinoline-3-carboxamide,
N-acetyl-N-(4-fluorophenyl)-4-acetoxy-1,2-dihydro-6-methoxy-1-methyl-2-oxo-quinoline-3-carboxamide,
N-(4-fluorophenyl)-4-acetoxy-1,2-dihydro-6-methoxy-1-methyl-2-oxo-quinoline-3-carboxamide,
N-iso-butyryl-N-(4-fluorophenyl)-4-iso-butyryloxy-1,2-dihydro-6-methoxy-1-methyl-2-oxo-quinoline-3-carboxamide,
N-benzoyl-N-(4-fluorophenyl)-4-benzoyloxy-1,2-dihydro-6-methoxy-1-methyl-2-oxo-quinoline-3-carboxamide,
N-ethoxycarbonyl-N-(4-fluorophenyl)-4-ethoxycarbonyloxy-1,2-dihydro-6-methoxy-1-methyl-2-oxo-quinoline-3-carboxamide,
N-(4-chlorophenyl)-1,2-dihydro-4-hydroxy-6-methoxy-1-methyl-2-oxo-quinoline-3-carboxamide,
N-acetyl-N-(4-chlorophenyl)-4-acetoxy-1,2-dihydro-6-methoxy-1-methyl-2-oxo-quinoline-3-carboxamide,
N-(4-chlorophenyl)-4-acetoxy-1,2-dihydro-6-methoxy-1-methyl-2-oxo-quinoline-3-carboxamide,
N-iso-butyryl-N-(4-chlorophenyl)-4-iso-butyryloxy-1,2-dihydro-6-methoxy-1-methyl-2-oxo-quinoline-3-carboxamide,
N-benzoyl-N-(4-chlorophenyl)-4-benzoyloxy-1,2-dihydro-6-methoxy-1-methyl-2-oxo-quinoline-3-carboxamide,
N-(4-chlorophenyl)-N-ethoxycarbonyl-4-ethoxycarbonyloxy-1,2-dihydro-6-methoxy-1-methyl-2-oxo-quinoline-3-carboxamide,
N-phenyl-1,2-dihydro-4-hydroxy-1-methyl-2-oxo-6-trifluoromethoxy-quinoline-3-carboxamide,
N-acetyl-N-phenyl-4-acetoxy-1,2-dihydro-1-methyl-2-oxo-6-trifluoromethoxy-quinoline-3-carboxamide,
N-phenyl-4-acetoxy-1,2-dihydro-1-methyl-2-oxo-6-trifluoromethoxy-quinoline-3-carboxamide,
N-phenyl-6-fluoro-1,2-dihydro-4-hydroxy-1-methyl-2-oxo-quinoline-3-carboxamide,
N-acetyl-N-phenyl-4-acetoxy-6-fluoro-1,2-dihydro-1-methyl-2-oxo-quinoline-3-carboxamide,
N-phenyl-4-acetoxy-6-fluoro-1,2-dihydro-1-methyl-2-oxo-quinoline-3-carboxamide,
N-acetyl-N-phenyl-4-acetoxy-6-chloro-1,2-dihydro-1-methyl-2-oxo-quinoline-3-carboxamide,
N-phenyl-4-acetoxy-6-chloro-1,2-dihydro-1-methyl-2-oxo-quinoline-3-carboxamide,
N-iso-butyryl-N-phenyl-4-iso-butyryloxy-6-chloro-1,2-dihydro-1-methyl-2-oxo-quinoline-3-carboxamide,
N-phenyl-4-iso-butyryloxy-6-chloro-1,2-dihydro-1-methyl-2-oxo-quinoline-3-carboxamide,
N-benzoyl-N-phenyl-4-benzoyloxy-6-chloro-1,2-dihydro-1-methyl-2-oxo-quinoline-3-carboxamide,
N-phenyl-4-benzoyloxy-6-chloro-1,2-dihydro-1-methyl-2-oxo-quinoline-3-carboxamide,
N-ethoxycarbonyl-N-phenyl-4-ethoxycarbonyloxy-6-chloro-1,2-dihydro-1-methyl-2-oxo-quinoline-3-carboxamide,
N-phenyl-4-diethylphosphoryloxy-6-chloro-1,2-dihydro-1-methyl-2-oxo-quinoline-3-carboxamide,
N-(4-fluorophenyl)-6-chloro-1,2-dihydro-4-hydroxy-1-methyl-2-oxo-quinoline-3-carboxamide,
N-acetyl-N-(4-fluorophenyl)-4-acetoxy-6-chloro-1,2-dihydro-1-methyl-2-oxo-quinoline-3-carboxamide,
N-(4-fluorophenyl)-4-acetoxy-6-chloro-1,2-dihydro-1-methyl-2-oxo-quinoline-3-carboxamide,
N-n-butyryl-N-(4-fluorophenyl)-4-n-butyryloxy-6-chloro-1,2-dihydro-1-methyl-2-oxo-quinoline-3-carboxamide,
N-iso-butyryl-N-(4-fluorophenyl)-4-iso-butyryloxy-6-chloro-1,2-dihydro-1-methyl-2-oxo-quinoline-3-carboxamide,
N-benzoyl-N-(4-fluorophenyl)-4-benzoyloxy-6-chloro-1,2-dihydro1-methyl-2-oxo-quinoline-3-carboxamide,
N-ethoxycarbonyl-N-(4-fluorophenyl)-6-chloro-4-ethoxycarbonyloxy-1,2-dihydro-1-methyl-2-oxo-quinoline-3-carboxamide,
N-(4-chlorophenyl)-6-chloro-1,2-dihydro-4-hydroxy-1-methyl-2-oxo-quinoline-3-carboxamide,
N-acetyl-N-(4-chlorophenyl)-4-acetoxy-6-chloro-1,2-dihydro-1-methyl-2-oxo-quinoline-3-carboxamide,
N-(4-chlorophenyl)-4-acetoxy-6-chloro-1,2-dihydro-1-methyl-2-oxo-quinoline-3-carboxamide,
N-n-butyryl-N-(4-chlorophenyl)-4-n-butyryloxy-6-chloro-1,2-dihydro-1-methyl-2-oxo-quinoline-3-carboxamide,
N-iso-butyryl-N-(4-chlorophenyl)-4-iso-butyryloxy-6-chloro-1,2-dihydro-1-methyl-2-oxo-quinoline-3-carboxamide,
N-benzoyl-N-(4-chlorophenyl)-4-benzoyloxy-6-chloro-1,2-dihydro1-methyl-2-oxo-quinoline-3-carboxamide,
N-(4-chlorophenyl)-N-ethoxycarbonyl-6-chloro-4-ethoxycarbonyloxy-1,2-dihydro-1-methyl-2-oxo-quinoline-3-carboxamide,
N-(4-methoxyphenyl)-6-chloro-1,2-dihydro-4-hydroxy-1-methyl-2-oxo-quinoline-3-carboxamide,
N-acetyl-N-(4-methoxyphenyl)-4-acetoxy-6-chloro-1,2-dihydro-1-methyl-2-oxo-quinoline-3-carboxamide,
N-(4-methoxyphenyl)-4-acetoxy-6-chloro-1,2-dihydro-1-methyl-2-oxo-quinoline-3-carboxamide,
N-n-butyryl-N-(4-methoxyphenyl)-4-n-butyryloxy-6-chloro-1,2-dihydro-1-methyl-2-oxo-quinoline-3-carboxamide,
N-iso-butyryl-N-(4-methoxyphenyl)-4-iso-butyryloxy-6-chloro-1,2-dihydro-1-methyl-2-oxo-quinoline-3-carboxamide,
N-benzoyl-N-(4-methoxyphenyl)-4-benzoyloxy-6-chloro-1,2-dihydro1-methyl-2-oxo-quinoline-3-carboxamide,
N-ethoxycarbonyl-N-(4-methoxyphenyl)-6-chloro-4-ethoxycarbonyloxy-1,2-dihydro-1-methyl-2-oxo-quinoline-3-carboxamide,
N-phenyl-6-bromo-1,2-dihydro-4-hydroxy-1-methyl-2-oxo-quinoline-3-carboxamide,
N-acetyl-N-phenyl-4-acetoxy-6-bromo-1,2-dihydro-1-methyl-2-oxo-quinoline-3-carboxamide,
N-phenyl-4-acetoxy-6-bromo-1,2-dihydro-1-methyl-2-oxo-quinoline-3-carboxamide,
N-acetyl-N-phenyl-4-acetoxy-1,2-dihydro-1-methyl-6-methylthio-2-oxo-quinoline-3-carboxamide,
N-phenyl-4-acetoxy-1,2-dihydro-1-methyl-6-methylthio-2-oxo-quinoline-3-carboxamide, N-iso-butyryl-N-phenyl-4-iso-butyryloxy-1,2-dihydro-1-methyl-6-methylthio-2-oxo-quinoline-3-carboxamide,
N-phenyl-4-iso-butyryloxy-1,2-dihydro-1-methyl-6-methylthio-2-oxo-quinoline-3-carboxamide,
N-benzoyl-N-phenyl-4-benzoyloxy-1,2-dihydro-1-methyl-6-methylthio-2-oxo-quinoline-3-carboxamide,
N-phenyl-4-benzoyloxy-1,2-dihydro-1-methyl-6-methylthio-2-oxo-quinoline-3-carboxamide,
N-ethoxycarbonyl-N-phenyl-4-ethoxycarbonyloxy-1,2-dihydro-1-methyl-6-methylthio-2-oxo-quinoline-3-carboxamide,
N-phenyl-4-diethylphosphoryloxy-1,2-dihydro-1-methyl-6-methylthio-2-oxo-quinoline-3-carboxamide,
N-(4-fluorophenyl)-1,2-dihydro-4-hydroxy-1-methyl-6-methylthio-2-oxo-quinoline-3-carboxamide,
N-acetyl-N-(4-fluorophenyl)-4-acetoxy-1,2-dihydro-1-methyl-6-methylthio-2-oxo-quinoline-3-carboxamide,
N-(4-fluorophenyl)-4-acetoxy-1,2-dihydro-1-methyl-6-methylthio-2-oxo-quinoline-3-carboxamide,
N-(4-chlorophenyl)-1,2-dihydro-4-hydroxy-1-methyl-6-methylthio-2-oxo-quinoline-3-carboxamide,
N-acetyl-N-(4-chlorophenyl)-4-acetoxy-1,2-dihydro-1-methyl-6-methylthio-2-oxo-quinoline-3-carboxamide,
N-(4-chlorophenyl)-4-acetoxy-1,2-dihydro-1-methyl-6-methylthio-2-oxo-quinoline-3-carboxamide,
N-(4-methoxyphenyl)-1,2-dihydro-4-hydroxy-1-methyl-6-methylthio-2-oxo-quinoline-3-carboxamide,
N-acetyl-N-(4-methoxyphenyl)-4-acetoxy-1,2-dihydro-1-methyl-6-methylthio-2-oxo-quinoline-3-carboxamide,
N-(4-methoxyphenyl)-4-acetoxy-1,2-dihydro-1-methyl-6-methylthio-2-oxo-quinoline-3-carboxamide,
N-acetyl-N-phenyl-1,2-dihydro-4-hydroxy-1-methyl-6-methylsulfinyl-2-oxo-quinoline-3-carboxamide,
N-acetyl-N-phenyl-4-acetoxy-1,2-dihydro-1-methyl-6-methylsulfinyl-2-oxo-quinoline-3-carboxamide,
N-phenyl-4-acetoxy-1,2-dihydro-1-methyl-6-methylsulfinyl-2-oxo-quinoline-3-carboxamide,
N-phenyl-6,7-dihydro-4-hydroxy-7-methyl-6-oxo-thieno[2,3-b]pyridine-5-carboxamide,
N-acetyl-N-phenyl-4-acetoxy-6,7-dihydro-7-methyl-6-oxo-thieno[2,3-b]pyridine-5-carboxamide,
N-phenyl-4-acetoxy-6,7-dihydro-7-methyl-6-oxo-thieno[2,3-b]pyridine-5-carboxamide,
N-phenyl-6,7-dihydro-4-hydroxy-3,7-dimethyl-6-oxo-thieno[2,3-b]pyridine-5-carboxamide,
N-acetyl-N-phenyl-4-acetoxy-6,7-dihydro-3,7-dimethyl-6-oxo-thieno[2,3-b]pyridine-5-carboxamide,
N-phenyl-4-acetoxy-6,7-dihydro-3,7-dimethyl-6-oxo-thieno[2,3-19]pyridine-5-carboxamide,
N-iso-butyryl-N-phenyl-4-iso-butyryloxy-6,7-dihydro-3,7-dimethyl-6-oxo-thieno[2,3-b]pyridine-5-carboxamide,
N-phenyl-4-iso-butyryloxy-6,7-dihydro-3,7-dimethyl-6-oxo-thieno[2,3-b]pyridine-5-carboxamide,
N-benzoyl-N-phenyl-4-benzoyloxy-6,7-dihydro-3,7-dimethyl-6-oxo-thieno[2,3-b]pyridine-5-carboxamide,
N-phenyl-4-benzoyloxy-6,7-dihydro-3,7-dimethyl-6-oxo-thieno[2,3-b]pyridine-5-carboxamide,
N-ethoxycarbonyl-N-phenyl-4-ethoxycarbonyloxy-6,7-dihydro-3,7-dimethyl-6-oxo-thieno[2,3-b]pyridine-5-carboxamide,
N-phenyl-4-diethylphosphoryloxy-6,7-dihydro-3,7-dimethyl-6-oxo-thieno[2,3-b]pyridine-5-carboxamide,
N-(4-fluorophenyl)-6,7-dihydro-4-hydroxy-3,7-dimethyl-6-oxo-thieno[2,3-b]pyridine-5-carboxamide,
N-acetyl-N-(4-fluorophenyl)-4-acetoxy-6,7-dihydro-3,7-dimethyl-6-oxo-thieno[2,3-b]pyridine-5-carboxamide,
N-(4-fluorophenyl)-4-acetoxy-6,7-dihydro-3,7-dimethyl-6-oxo-thieno[2,3-b]pyridine-5-carboxamide,
N-iso-butyryl-N-(4-fluorophenyl)-4-iso-butyryloxy-6,7-dihydro-3,7-dimethyl-6-oxo-thieno[2,3-b]pyridine-5-carboxamide,
N-benzoyl-N-(4-fluorophenyl)-4-benzoyloxy-6,7-dihydro-3,7-dimethyl-6-oxo-thieno[2,3-b]pyridine-5-carboxamide,
N-ethoxycarbonyl-N-(4-fluorophenyl)-4-ethoxycarbonyloxy-6,7-dihydro-3,7-dimethyl-6-oxo-thieno[2,3-b]pyridine-5-carboxamide,
N-(4-chlorophenyl)-6,7-dihydro-4-hydroxy-3,7-dimethyl-6-oxo-thieno[2,3-b]pyridine-5-carboxamide,
N-acetyl-N-(4-chlorophenyl)-4-acetoxy-6,7-dihydro-3,7-dimethyl-6-oxo-thieno[2,3-b]pyridine-5-carboxamide,
N-(4-chlorophenyl)-4-acetoxy-6,7-dihydro-3,7-dimethyl-6-oxo-thieno[2,3-b]pyridine-5-carboxamide,
N-(4-methoxyphenyl)-6,7-dihydro-4-hydroxy-3,7-dimethyl-6-oxo-thieno[2,3-b]pyridine-5-carboxamide,
N-acetyl-N-(4-methoxyphenyl)-4-acetoxy-6,7-dihydro-3,7-dimethyl-6-oxo-thieno[2,3-b]pyridine-5-carboxamide,
N-(4-methoxyphenyl)-4-acetoxy-6,7-dihydro-3,7-dimethyl-6-oxo-thieno[2,3-b]pyridine-5-carboxamide,
N-iso-butyryl-N-(4-methoxyphenyl)-4-iso-butyryloxy-6,7-dihydro-3,7-dimethyl-6-oxo-thieno[2,3-b]pyridine-5-carboxamide,
N-benzoyl-N-(4-methoxyphenyl)-4-benzoyloxy-6,7-dihydro-3,7-dimethyl-6-oxo-thieno[2,3-b]pyridine-5-carboxamide,
N-ethoxycarbonyl-N-(4-methoxyphenyl)-4-ethoxycarbonyloxy-6,7-dihydro-3,7-dimethyl-6-oxo-thieno[2,3-b]pyridine-5-carboxamide,
N-phenyl-3-ethyl-6,7-dihydro-4-hydroxy-7-methyl-6-oxo-thieno[2,3-b]pyridine-5-carboxamide,
N-acetyl-N-phenyl-4-acetoxy-3-ethyl-6,7-dihydro-7-methyl-6-oxo-thieno[2,3-b]pyridine-5-carboxamide,
N-phenyl-4-acetoxy-3-ethyl-6,7-dihydro-7-methyl-6-oxo-thieno[2,3-b]pyridine-5-carboxamide,
N-phenyl-6,7-dihydro-4-hydroxy-7-methyl-6-oxo-3-trifluoromethyl-thieno[2,3-b]pyridine-5-carboxamide,
N-acetyl-N-phenyl-4-acetoxy-6,7-dihydro-7-methyl-6-oxo-3-trifluoromethyl-thieno[2,3-b]pyridine-5-carboxamide, and
N-phenyl-4-acetoxy-6,7-dihydro-7-methyl-6-oxo-3-trifluoromethyl-thieno[2,3-b]pyridine-5-carboxamide.

11. A pharmaceutical composition comprising a compound or a pharmaceutically acceptable salt thereof according to claim 1, admixed with one or more pharmaceutically acceptable excipients or carriers.

12. The pharmaceutical composition according to claim 11, wherein the excipients are selected from the group consisting of filling agents, lubricants, flavours, colourings, sweetenings, buffers, acidifying agents, diluents, and preservatives.

13. The pharmaceutical composition according to claim 11, which is suitable for administration by one or more of orally, by oral inhalation, intramuscularly, intravenously, intraperitoneally, or subcutaneously, via implants, rectally, intranasally, or transdermally.

14. A method of treatment comprising
administration of a pharmaceutically effective amount of the compound or a pharmaceutically acceptable salt thereof according to claim 1 or a pharmaceutical composition comprising the compound or a pharmaceutically acceptable salt thereof according to claim 1, admixed with one or more pharmaceutically acceptable excipients or carriers to a subject suffering from cancer, autoimmune disorder, or other disorder with an immunological component, wherein the disorder with an immunological component is selected from the group consisting of asthma, allergy, infection, bone loss, atherosclerosis, diabetes type 2, graft-versus-host, and transplant rejection.

15. The method of treatment according to claim 14, wherein the method is for the treatment of cancer and the subject is suffering from a cancer selected from the group consisting of prostate cancer, intestinal cancer, and leukemia.

16. The method of treatment according to claim 14, wherein the method is for the treatment of an autoimmune disorder and the subject is suffering from an autoimmune disorder selected from the group consisting of rheumatoid arthritis, multiple sclerosis, systemic lupus erythematosus, inflammatory bowel disease, diabetes type 1, and psoriasis.

17. The method of treatment according to claim 14, wherein the method is for the treatment of a disorder with an immunological component and the subject is suffering from a disorder with an immunological component selected from the group consisting of asthma, allergy, infection, bone loss, atherosclerosis, diabetes type 2, graft-versus-host, and transplant rejection.

18. The pharmaceutical composition according to claim 13, which is suitable to be administered orally.

* * * * *